United States Patent
Blum et al.

(10) Patent No.: US 11,712,494 B2
(45) Date of Patent: Aug. 1, 2023

(54) ENHANCED EXHALED AIR COLLECTOR AND AIR PURIFICATION UNIT AND SYSTEM

(71) Applicant: Air-Clenz Systems, LLC, Atlanta, GA (US)

(72) Inventors: Ronald Blum, Atlanta, GA (US); Anita Broach, Christiansburg, VA (US); Russell French, Atlanta, GA (US); Jack Loeb, Fisher Island, FL (US)

(73) Assignee: Air-Clenz Systems, LLC, Atlanta, GA (US)

( * ) Notice: Subject to any disclaimer, the term of this patent is extended or adjusted under 35 U.S.C. 154(b) by 0 days.

(21) Appl. No.: 17/404,570

(22) Filed: Aug. 17, 2021

(65) Prior Publication Data

US 2021/0386903 A1 Dec. 16, 2021

Related U.S. Application Data

(63) Continuation of application No. 17/353,341, filed on Jun. 21, 2021, which is a continuation of application No. 17/331,239, filed on May 26, 2021, now Pat. No. 11,324,850.

(60) Provisional application No. 63/222,638, filed on Jul. 16, 2021, provisional application No. 63/216,644, filed on Jun. 30, 2021, provisional application No. 63/196,565, filed on Jun. 3, 2021, provisional application No. 63/195,608, filed on Jun. 1, 2021, provisional application No. 63/182,964, filed on May 2, 2021, provisional application No. 63/173,443, filed
(Continued)

(51) Int. Cl.
*A61L 9/20* (2006.01)
*A61L 9/22* (2006.01)

(52) U.S. Cl.
CPC .............. *A61L 9/20* (2013.01); *A61L 9/22* (2013.01); *A61L 2209/111* (2013.01); *A61L 2209/134* (2013.01); *A61L 2209/14* (2013.01); *A61L 2209/15* (2013.01)

(58) Field of Classification Search
CPC ... A61L 9/20; A61L 9/205; A61L 9/22; A61L 9/14; A61L 2209/14; A61L 2209/15; A61L 2209/16
See application file for complete search history.

(56) References Cited

U.S. PATENT DOCUMENTS

| 4,974,915 A | 12/1990 | Bussard |
| 5,267,895 A | 12/1993 | Mitchell et al. |

(Continued)

FOREIGN PATENT DOCUMENTS

| CN | 2582610 Y | 10/2003 |
| CN | 104995511 A | 10/2015 |
| CN | 107901728 A | 4/2018 |

OTHER PUBLICATIONS

Application No. PCT/US2021/034281, International Search Report and Written Opinion dated Sep. 17, 2021.
(Continued)

*Primary Examiner* — Timothy C Cleveland
(74) *Attorney, Agent, or Firm* — Woods Rogers Vandeventer Black PLC; Nathan A. Evans

(57) ABSTRACT

An exhaled air purification device comprising an exhaled air purification chamber and an air collector capable of capturing, collecting, and cleaning exhaled air of an individual sitting in front of the exhaled air purification device.

12 Claims, 32 Drawing Sheets

Related U.S. Application Data on Apr. 11, 2021, provisional application No. 63/158,983, filed on Mar. 10, 2021, provisional application No. 63/156,598, filed on Mar. 4, 2021, provisional application No. 63/149,581, filed on Feb. 15, 2021, provisional application No. 63/125,701, filed on Dec. 15, 2020, provisional application No. 63/063,727, filed on Aug. 10, 2020, provisional application No. 63/060,009, filed on Aug. 1, 2020, provisional application No. 63/051,309, filed on Jul. 13, 2020, provisional application No. 63/050,253, filed on Jul. 10, 2020, provisional application No. 63/048,877, filed on Jul. 7, 2020, provisional application No. 63/046,430, filed on Jun. 30, 2020, provisional application No. 63/031,321, filed on May 28, 2020, provisional application No. 63/029,956, filed on May 26, 2020.

(56) References Cited

U.S. PATENT DOCUMENTS

| | | |
|---|---|---|
| 6,497,275 B1 | 12/2002 | Elliot |
| 2011/0155150 A1* | 6/2011 | Al-Qassem ............ B01D 53/75 131/238 |
| 2013/0333570 A1 | 12/2013 | Kamperschroer et al. |
| 2015/0140915 A1 | 5/2015 | Rawlinson |
| 2019/0160417 A1 | 5/2019 | Matsumoto et al. |
| 2021/0145171 A1 | 5/2021 | Rozeboom et al. |

OTHER PUBLICATIONS

A. K. Melikov; Advanced air distribution: improving health and comfort while reducing energy use; Indoor Air 2016; 26: 112-124; John Wiley & Sons Ltd.; Singapore.

Arsen K. Melikov; Advanced air distribution for minimizing airborne cross-infection in aircraft cabins; HVAC&R Research (2013) 19, 926-933; Taylor & Francis.

Jianlei Niu; Experimental study on a chair-based personalized ventilation system; Science Direct; 2005; Elsevier Ltd.

Application No. PCT/US 21/46307, International Search Report and Written Opinion dated Dec. 9, 2021.

* cited by examiner

ENHANCED EXHALED AIR COLLECTOR AND AIR PURIFICATION UNIT AND SYSTEM

CROSS REFERENCE TO RELATED APPLICATIONS

The present application relies on the disclosures of and claims priority to and the benefit of the filing dates of the following U.S. patent applications:

U.S. application Ser. No. 17/353,341, Enhanced Exhaled Air Collector and Air Purification Unit and System, filed Jun. 21, 2021;

U.S. application Ser. No. 17/331,239, Exhaled Air Purification Unit and System for Indoor Multi-Person Venue or Environment, filed May 26, 2021;

U.S. Appl. No. 63/029,956, Microbe Protection Systems, filed May 26, 2020;

U.S. Appl. No. 63/031,321, Microbe Protection Modules, filed May 28, 2020;

U.S. Appl. No. 63/046,430, Air Suction Sterilization Elevator Car, filed Jun. 30, 2020;

U.S. Appl. No. 63/048,877, Vehicle Microbe Protection System, filed Jul. 7, 2020;

U.S. Appl. No. 63/050,253, Advanced Air Suction Sterilization Elevator Car, filed Jul. 10, 2020;

U.S. Appl. No. 63/051,309, Advanced Vehicle Microbe Protection System, filed Jul. 13, 2020;

U.S. Appl. No. 63/060,009, Advanced Air Suction Air Sterilization Protection System, filed Aug. 1, 2020;

U.S. Appl. No. 63/063,727, Advanced Microbe Trap and Face Mask, filed Aug. 10, 2020;

U.S. Appl. No. 63/125,701, Advanced Air Purification System for Multi-Person Environment, filed Dec. 15, 2020;

U.S. Appl. No. 63/149,581, Multi-person Venue Air Purification System, filed Feb. 15, 2021;

U.S. Appl. No. 63/156,598, Air Handling Purification System, filed Mar. 4, 2021;

U.S. Appl. No. 63/158,983, Air Handling Purification System, filed Mar. 10, 2021;

U.S. Appl. No. 63/173,443, Recessed Personal Air Purifier for Backside of Seat Back, filed Apr. 11, 2021;

U.S. Appl. No. 63/182,964, Personal Air Purification Unit and System, filed May 2, 2021;

U.S. Appl. No. 63/195,608, Exhaled Air Collector and Air Purification for Desks and/or Tables, filed Jun. 1, 2021;

U.S. Appl. No. 63/196,565, Enhanced Exhaled Air Collector and Air Purification for Desks and/or Tables, filed Jun. 3, 2021;

U.S. Appl. No. 63/216,644, Exhaled Air Guide for Exhaled Air Collector, filed Jun. 30, 2021; and U.S. Appl. No. 63/222,638, Additional Exhaled Air Purification Units, filed Jul. 16, 2021.

The disclosures of those applications are hereby incorporated by reference herein in their entireties.

BACKGROUND OF THE INVENTION

Field of the Invention

In aspects, the invention disclosed herein is directed to an exhaled air purification unit/device and/or system providing the ability to capture/collect, isolate, transport, and/or destroy airborne pathogens and contaminants faster than currently available HVAC systems, HVAC purification systems, and/or HVAC air handling systems, permit. The invention disclosed herein is directed, in aspects, to an exhaled air purification unit and/or system that is capable of capturing/collecting, isolating and cleaning the exhaled air of a plurality of individuals. In most but not all cases these individuals are seated. By way of example only, airborne pathogens can float for over 15 minutes within a building traveling great distances before they are captured by the HVAC return. This especially true for auditoriums, theaters, and schools. It is estimated that around 70% of the day spent at school is spent sitting at a desk or table. As with auditoriums, theaters, and school classrooms, many times the closest HVAC air return is far across the room from where an individual is seated. Thus, exhaled air of multiple individuals must travel in the air across multiple rows of seats, desks, and/or tables before it is captured within the HVAC air return. This is also true when considering an air purifier. An air purifier pulls air from a room through the air purifier thus cleaning the air. However, an air purifier, like that of the HVAC system cleans the room air "after" exhaled air is very dispersed throughout the air of the indoor venue. Thus, any contagious pathogens will have floated through the air of the indoor venue for some time before being captured and cleaned.

Currently, additional airflow and/or upgraded HEPA filters are being added to many schools and universities air handling systems. While this will help somewhat in reducing pathogen spread, it will not adequately or sufficiently satisfy the need. Simply upgrading the HVAC system will not significantly reduce the potential of pathogen airborne contagious spread within a building or vehicle environment. There is a pressing need to capture and isolate exhaled air of an individual or individuals much closer to the face of an individual or individuals. By doing this, a cone of exhaled air from an individual is significantly reduced in cubic area and diameter and it is possible to capture and/or isolate part of most of it.

Description of the Related Art

Aerosol spray which transports viruses, including coronavirus ("COVID"), occurs from a human exhaled breath, talking, shouting, coughing, and sneezing. Under normal circumstances it is known that exhaled air forms a cone shape as it comes from the mouth and nose of an individual. Generally, at its origination at the nose and mouth it is approximately 55 mm in diameter. From there it usually (but not always) expands outward at 22 degrees to 33 degrees and has a center trajectory of 10 degrees downward. The louder the noise the human makes with his or her voice, lungs, throat, or mouth generally the farther the viral or bacterial aerosol is moved in the air. Recent studies show that an aerosol comprising viral float can remain airborne for up to 15 minutes in a closed confined environment. Research studies have showed that singing, yelling, coughing, and sneezing can spread COVID aerosol up to 3+ meters. The velocity of exhaled air can range between 0.8 meters per second to 50 meters per second depending upon an easy breath of exhaled air to that of a sneeze, with a cough being somewhat less than a sneeze. By way of example only, COVID 19, COVID variants, coronavirus, measles, mumps, SARS, smallpox, common colds, influenza, and tuberculosis can be spread by way of being airborne. Closed confined multi-seated indoor environments are extremely vulnerable to coronaviral spread. There is a need for capturing, isolating, and cleaning the exhaled air of individuals far more quickly than what is done today.

SUMMARY OF THE INVENTION

In embodiments of the present invention, an exhaled air purification system may comprise one or a plurality of exhaled air collectors networked to one or more remote air purification chambers. An exhaled air purification unit may comprise an exhaled air collector and an exhaled air purification chamber. The exhaled air purification unit can be mobile and can be moved, by way of example only, from a tabletop to a different tabletop, from desk to a different desk, from back of a chair or seat to a different back of a seat or chair, or any combination thereof. The exhaled air purification unit can be fixed and thus not moved. The exhaled air collector can be positioned on a desktop or tabletop, attached to a seat back, integrated within a seat back, or distance separated and behind a seat back. A seat back can be formed or shaped to be an exhaled air collector. An exhaled air collector in most, but not all cases, can comprise an open front.

The exhaled air collector captures, collects exhaled air from and individual whose face is generally within 2 inches to 6 feet of the front of the exhaled air collector or an exhaled air guide connected to an exhaled air collector. In some cases, it can be within 1 foot to 6 feet and in other cases it can be 3 feet to 6 feet, by way of example only. The way the exhaled air is collected and captured by the exhaled air collector is a combination of the velocity of the individual's exhaled air being collected, plus the trajectory of the individual's exhaled air combined with the air intake suction force of the exhaled air purification unit, or, said another way, the air intake suction force of the air suction intake located, in aspects, within, connected to, or on a part of the exhaled air collector.

An exhaled air collector can comprise an internal back recessed air blocking surface. An exhaled air collector can comprise an optional exhaled air catch basin. The exhaled air collector is designed to capture an amount of the exhaled air of an individual sitting in front of the exhaled air collector and to move or permit the captured exhaled air to move into an air purification chamber for cleaning, filtering, purifying or any combination thereof. In embodiments, the exhaled air moves along with or is permitted to move along with air from the venue in which the individual is sitting or standing.

In embodiments, the exhaled air collector can comprise an internal recessed air blocking surface. However, in certain embodiments the exhaled air collector can be devoid of a recessed exhaled air blocking surface and can open in its back to an exhaled air purification chamber that can be of the entire size of the back of the exhaled air collector. The exhaled air purification chamber in this case can comprise air suction intakes on the side that are common with the exhaled air collector and air exhaust outlets on the side that are common with the venue environment. In certain other embodiments the air suction intake side of the exhaled air purification chamber can fill a portion, or all, of one or more of the top, the side, the bottom, and/or the back of the exhaled air collector. An exhaled air suction intake can be an opening within a wall, floor, top, or bottom of the exhaled air collector that allows air to flow towards an air suction mechanism that provides an air suction force to such opening within the exhaled air collector. Such an air suction mechanism can be, by way of example only, a fan. The way the exhaled air collector, the exhaled air purification chamber, and/or that of the exhaled air purification unit is designed largely depends upon the venue to which it is being utilized.

As used herein a desk and table can have the same meaning. As used herein a desk and tabletop can have the same meaning. As used herein a table and desktop can have the same meaning. As used herein a desk and table can be that of a chair, a seat, or a bench that comprises a desk like attachment. As used herein a desk and table can be that of chair, seat or bench that comprises a writing ledge attachment. As used herein a desk and table can be that of chair, seat or bench that comprises an attached or integrated horizontal work surface. While in most embodiments an individual is sitting or standing in front of an air purification unit resting on a desk or a table, the invention disclosure herein covers that of an individual standing in front of a standing desk or table that further supports a computer, by way of example only, a tablet, a laptop, or a desktop.

As used herein an airborne particulate can be that of, but is not limited to, a virus, bacteria, fungus, pathogen, or contaminant. As used herein a pathogen can include bacteria, fungi, protozoa, worms, viruses, and even infectious proteins called prions. As used herein, "seat," "chair," "bench," and "sitting apparatus," have the same meaning and can be used interchangeably. As used herein the word "clean" or variations thereof can have the same meaning as purify. Clean air can mean the same as cleaned air. Cleaned air can be that of filtered air. Cleaned air can be that of purified air. Cleaned air can be that of sterilized air. The words purify and/or clean can imply that of partially cleaned, partially purified, or fully cleaned and fully purified. As used herein an exhaled air purifier can mean the same thing as an exhaled air purification chamber. Such exhaled air cleaning/purification can occur by way of one or more of: filtration, chemical microbicidal purification, light microbicidal purification (such as, by way of example only, UVC light), mechanical microbicidal purification, thermal microbicidal purification, microbicidal agents, or microbicidal materials. It is understood and implied herein that when exhaled air is collected and cleaned or purified, air from the room and/or venue is also mixed with the collected exhaled air. Thus, when using the terms exhaled air collector, exhaled air purification chamber, or exhaled air purification unit, it is understood that the collector, chamber, and purification unit will always be handling and processing both exhaled air and some of the venue's room air. As used herein an exhaled purification system means the same as an exhaled air purification system. As used herein, an air purification unit means the same as an air purification device. As used herein an air purification device means the same as an air treatment device or air treating device, and an air treatment device or air treating device can mean the same as an air purification unit.

An electronic display screen, video display screen, or display screen can all have the same meaning. As used herein someone that is sitting or standing "in front" of an exhaled air purification unit is that of someone sitting or standing at a table as depicted in the figures included with this invention disclosure. As used herein someone sitting behind a chair, seat, or bench is sitting in the chair, seat, or bench behind that of the chair, seat, or bench that is in front thereof. As used herein the back of a chair, seat, bench is the backrest and/or headrest of the chair, seat, or bench.

As used herein the abbreviation CADR is basically a reflection of the air flow (CFM—cubic feet per minute) times the efficiency of the air filter. So if an air filter has 200 cfm and 100% efficiency the CADR would be 200. If the air filter has 200 cfm and 75% efficiency the CADR would be 150. As used herein CFM means cubic feet per minute of air flow.

BRIEF DESCRIPTION OF THE DRAWINGS

The accompanying drawings illustrate certain aspects of some of the embodiments of the present invention and should not be used to limit or define the invention. Together with the written description the drawings serve to explain certain principles of the invention.

FIG. 45B is a drawing of a possible embodiment according to the present invention showing a top-down view of a table comprising multiple exhaled air collectors and a central air suction conduit that lead downwards through the tabletop and to an air purification chamber below the table or remote to the table. In this embodiment, there may be a shared air section intake(s), or separate air suction intakes for each of several exhaled air collectors. In aspects of the current invention, one or more exhaled air collectors may share an air suction intake, an air suction conduit, and/or an air purification chamber.

DETAILED DESCRIPTION OF VARIOUS EMBODIMENTS OF THE INVENTION

Figure 1:
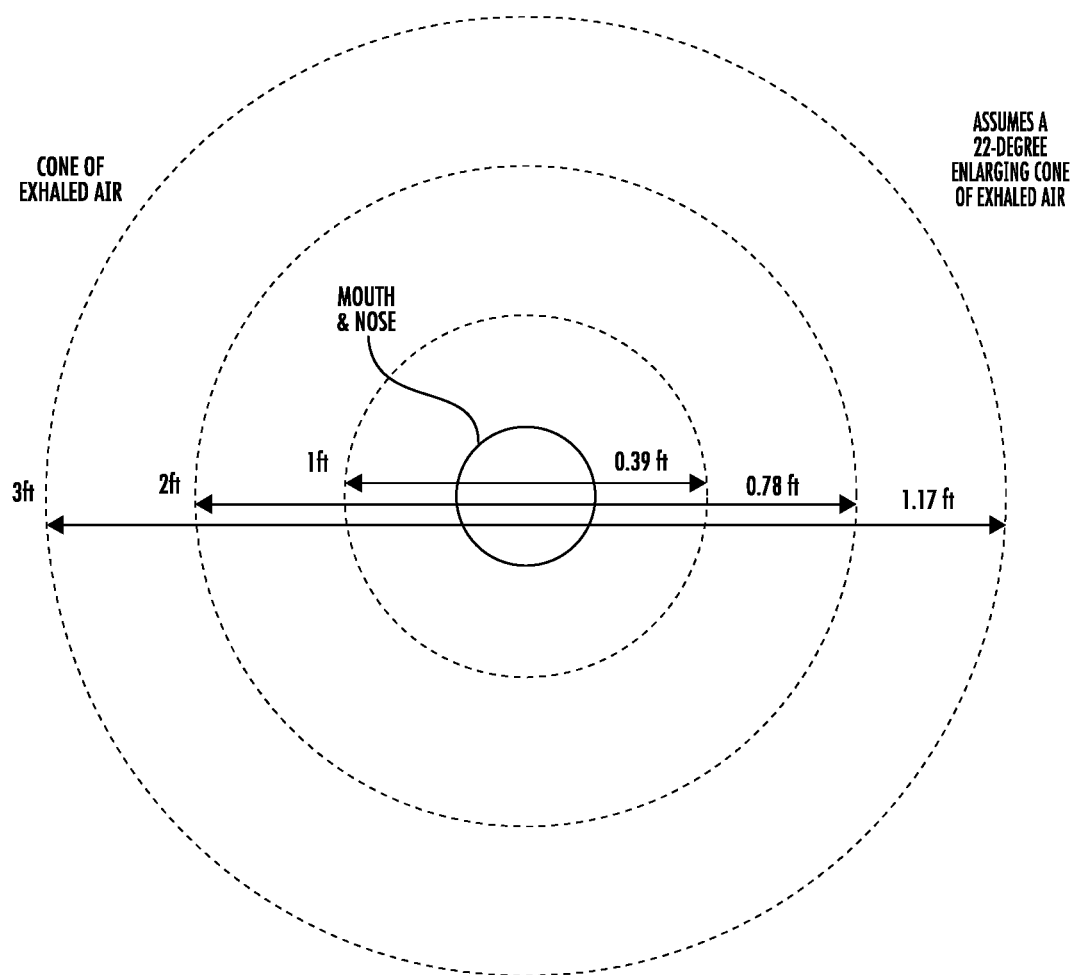
FIG. 1 is a schematic demonstrating the expanded side of a cone of exhaled air originating at one's mouth or nose having originating dimension of 55 mm in diameter and expanding out at 22 degrees for the distances of one foot, two feet, and three feet, assuming 22 degrees enlarging cone of exhaled air.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Embodiments comprising various features may also consist of or consist essentially of those various features. Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention.

All references cited in this specification are hereby incorporated by reference in their entireties.

The present invention relates to capturing and cleaning, purifying, sanitizing, or otherwise conditioning or treating exhaled air from a human, then returning that air to the same environment, or in cases not returning that air to the same environment.

In aspects, the present invention can be used in a multi-person environment or venue such as a school, classroom, teaching facility, learning environment, auditorium, music studio, or anyplace else where more than one person can be found in close enough proximity to infect, communicate, transmit, or otherwise spread with one another any airborne illness, virus, sickness, microbe, pathogen, or any other condition, element, or particulate that can be communicable from one human to another. As explained herein, the invention includes, in aspects, an exhaled air collector to collect exhaled air from a human, which in cases may also include one or more of the following: exhaled air guide, an air suction intake, an air suction conduit, or an air purification chamber. An air purification chamber can be one or more of: partially or fully within an exhaled air collector, connected to an exhaled air collector, attached to an exhaled air collector, supported by a desktop or tabletop, attached under a desktop or tabletop, attached to a desktop or tabletop, within a seat back, within a seat, under a seat, distance separate but directly behind a seat or seatback, remote to a desktop or tabletop, and/or remote to a seat back or seat. In embodiments of the present invention, an exhaled air purification system may comprise a plurality of exhaled air collectors networked to one or more remote air purification chambers. An exhaled air purification unit may comprise an exhaled air collector and an exhaled air purification chamber. The exhaled air purification unit can be mobile and can be moved, by way of example only, from a tabletop to a different tabletop, from desk to a different desk, from a back of a chair or seat to a different back of a seat or chair, or any combination thereof. The exhaled air purification unit can be fixed in position or location. The exhaled air collector can be positioned on a desktop or tabletop, attached to a seat back, integrated within a seat back, or distance separated and behind a seat back. A seat back can be formed or shaped to be an exhaled air collector. In a preferred embodiment, an exhaled air collector can comprise a partially or completely open front. An open front exhaled air collector can permit an individual to position his or her hands within the open front exhaled air collector and/or to place all or a portion of an item within the open front, such as computer, phone, book, writing instrument, paper, notebook, document, food, keyboard, instrument, microphone, or any other item within the open front and therefore, in aspects, partially or completely within the exhaled air collector or the cavity of the open front exhaled air collector. Thus, the open front air collector can allow for an individual to, by way of example only, hold and/or touch all or a portion of, within the open front exhaled air collector, food, paper, reading material, books, magazines, writing material, computer, and/or electronic display. An exhaled air collector can be used when standing, sitting, or laying. In embodiments where the exhaled air collector partially or completely surrounds a microphone, the front of the air collector can have an open front (see, e.g., FIG. 49). The exhaled air collector can comprise an open front, wherein the open front of the exhaled air collector allows for an electronic display to be viewed and touched by an individual or individuals whose air the exhaled air collector is collecting.

In embodiments, the exhaled air collector can collect the exhaled air of one or multiple individuals who are in front or substantially in front of the exhaled air collector. When multiple individuals are in front of an open front of an exhaled air collector, the exhaled air collector can comprise a left-to-right dimension (length, width, and/or height) capable of accommodating multiple individuals. In embodiments, an exhaled air collector capable of accommodating more than one individual can be divided into multiple sections, each in front of one individual or groups of individuals, in aspects. In embodiments, where more than one individual is located or positioned next to one another, multiple exhaled air collectors can be used, and they may be adjacent and/or connected to one another. An exhaled air collector for multiple individuals can have one or multiple air suction intakes; in aspects, each individual has his or her own air suction intake and in cases air suction intakes are shared between more than one individual. These one or multiple air suction intakes can connect to one or more common or shared air suction conduit(s) that connect to one or more exhaled air purification chambers, or each air suction intake can have its own air suction conduit that connects to one or more exhaled air purification chambers.

An exhaled air collector can comprise an internal back recessed air blocking surface. An exhaled air collector can comprise an optional exhaled air catch basin. The exhaled air collector can be designed to capture an amount of the exhaled air of an individual sitting in front of the exhaled air collector and to move or permit the captured exhaled air to move into an air purification chamber for cleaning, filtering, purifying, or any combination thereof. In embodiments, the exhaled air moves along with or is permitted to move along with air from the venue in which the individual is sitting or standing.

In embodiments, the exhaled air collector can comprise an internal recessed air blocking surface. In embodiments, the exhaled air collector can be devoid of a recessed exhaled air blocking surface. In embodiments the exhaled air collector can have an exhaled air guide to deflect a portion of an individual's exhaled air into the exhaled air collector. The exhaled air guide can be adjustable. The exhaled air guide can be fixed. In certain embodiments the exhaled air collector can comprise one or more fans to move exhaled air. In certain embodiments the exhaled air guide can comprise one or more fans to move exhaled air. In embodiments, a back or side of an exhaled air collector can open to an exhaled air purification chamber that can, in aspects, be of the entire size or part of the size of the back or side of the exhaled air collector. The exhaled air purification chamber can comprise one or more exhaled air suction intakes on one or more sides, front, bottom, and/or back, that are common or shared with the exhaled air collector; and, in aspects, one or more air exhaust outlets, air exhausts, or air vents on the sides, front, bottom, and/or back of the air purification chamber can be common with, shared with, or adjacent to the venue environment. In other embodiments, an air intake side of the exhaled air purification chamber can fill a portion, or all, of one or more of the top, the side, the bottom, and/or the back of the exhaled air collector. A way in which the exhaled air collector, the exhaled air purification chamber, and/or that of the exhaled air purification unit is designed can, in aspects, depend upon the venue to which it is being utilized.

As used herein a desk and table can have the same meaning. As used herein a desktop and tabletop can have the same meaning. As used herein a desk and table can be that of a chair, a seat, or a bench that comprises a desk like attachment. As used herein a desk and table can be that of chair, seat or bench that comprises a writing ledge attachment. As used herein a desk and table can be that of chair, seat or bench that comprises an attached or integrated horizontal surface, such as a work surface. While in embodiments an individual is sitting or standing in front of an air purification unit resting, positioned, or located on a desk or a table, the invention herein covers that of an individual standing in front of a standing desk or table that further supports, by way of example only, a computer, such as a tablet, a laptop, or a desktop.

As used herein, an airborne particulate can be that of, but is not limited to, a virus, bacteria, fungus, pathogen, or contaminant. As used herein, a pathogen can include, but is not limited to, bacteria, fungi, protozoa, worms, viruses, and infectious proteins called, in cases, prions. As used herein, "seat," "chair," "bench," and "sitting apparatus," have the same meaning and can be used interchangeably. As used herein, the word "clean" or variations thereof can have the same meaning as treated, purified, sterilized, sanitized, filtered, and variations thereof. Clean air can mean the same as cleaned air. Cleaned air can be that of filtered air. Cleaned air can be that of purified air. Cleaned air can be that of sterilized or sanitized air. The words purify and/or clean can mean that of partially cleaned, partially purified, fully cleaned, and/or fully purified. As used herein, an exhaled air purifier can mean the same thing as an exhaled air purification chamber. Exhaled air cleaning/purification can occur by way of one or more of, in aspects: filtration, chemical microbicidal purification, light microbicidal purification (such as, by way of example only, UVC light), mechanical microbicidal purification, thermal microbicidal purification, microbicidal agents, or microbicidal materials. It is understood and implied herein that when exhaled air is collected and cleaned or purified, air from the room and/or venue is also mixed with the collected exhaled air. Thus, when using the terms exhaled air collector, exhaled air purification chamber, or exhaled air purification unit, for example, it is understood that the exhaled air collector, air purification chamber, and air purification unit will always, sometimes, or most of the time be handling and processing both exhaled air and that of the venue's room air. As used herein, an exhaled purification system means the same as an exhaled air purification system. As used herein, an air purification unit means the same as an air purification device or air treating device.

As used herein, an electronic display screen, video display screen, or display screen can all have the same meaning. As used herein, someone that is "in front" of an exhaled air purification unit or exhaled air collector can be that of someone sitting, standing, or laying at a table or apparatus as depicted in the figures accompanying/included with the current application; and, in front can mean substantially in front. As used herein, someone sitting, standing, or laying behind a chair, seat, or bench is sitting, standing, or laying in the chair, seat, or bench behind that of the chair, seat, or bench that is in front thereof. As used herein, the back of a chair, seat, or bench can be, in examples, the backrest and/or headrest of the chair, seat, or bench.

The terms CADR and CFM would be understood by one of ordinary skill in the art. Further, as used herein, the abbreviation CADR is basically a reflection of the air flow (CFM—cubic feet per minute) times the efficiency of the air filter. So, by way of example only, if an air filter has 200 CFM and 100% efficiency, the CADR would be 200. If the air filter has 200 CFM and 75% efficiency, the CADR would be 150. As used herein CFM means cubic feet per minute of air flow.

In aspects, the invention is that of an exhaled air purification system that comprises one or more exhaled air collectors, wherein the one or more exhaled air collectors are connected to one or more air suction conduits, wherein the one or more air suction conduits connect to one or more air purification chambers, and wherein the front of one or more exhaled air collectors is a partially or completely open front. The exhaled air collector can comprise an open front, wherein the open front of the exhaled air collector allows for reading and/or writing material to be inserted, viewed, and/or handled by the individual or individuals whose air the exhaled air collector is collecting. The exhaled air collector can comprise an open front, wherein the open front of the exhaled air collector can allow for printed material to be partially or fully inserted, viewed, and/or handled by the individual or individuals whose air the exhaled air collector is collecting. The exhaled air collector can comprise an open front, wherein the open front of the exhaled air collector can allow for food to be partially or fully inserted, viewed, and/or handled by the individual or individuals whose air the exhaled air collector is collecting. The exhaled air collector can comprise an open front, wherein the open front of the exhaled air collector can allow for an electronic display to be partially or fully inserted to be viewed and/or to be touched and manually manipulated by the individual or individuals whose air the exhaled air collector is collecting. The exhaled air collector can comprise an open front, wherein the open front of the exhaled air collector can allow a computerized device to be partially or fully inserted, viewed, and/or handled by the individual or individuals whose air the exhaled air collector is collecting. The exhaled air collector can comprise an open front, wherein the open front of the exhaled air collector can allow a musical instrument to be partially or fully inserted, viewed, and/or handled by the individual or individuals whose air the exhaled air collector is collecting. The exhaled air collector can comprise an open front, wherein the open front of the exhaled air collector can allow an electronic device to be partially or fully inserted, viewed, and/or handled by the individual or individuals whose air the exhaled air collector is collecting.

A single exhaled air collector can collect the exhaled air of multiple individuals. A plurality of exhaled air collectors can be attached, connected, and/or adjacent to one another. A single exhaled air collector having an adequate or sufficient horizontal width and an open front can be subdivided to permit the collection of exhaled air from multiple individuals. One air collector having a sufficient or adequate horizontal width can comprise an open front and an open interior capable of collecting the exhaled air from multiple individuals. A plurality of exhaled air collectors can connect to one common air suction conduit. A single exhaled air collector that collects air from multiple individuals can comprise one air suction intake. A table, such as by way of example only, a circular table, can comprise multiple exhaled air collectors that connect to a shared air suction conduit, such as a central air suction conduit, and/or a shared air purification chamber. A table, such as by way of example only, a circular table, can comprise multiple individual exhaled air collectors that connect to a single exhaled air purification chamber, such as a central exhaled air purification chamber. A table, such as by way of example only, a circular table, can comprise a single circular or other shaped exhaled air collector that connects to an air suction conduit, such as a shared air suction conduit or central air suction conduit. A table, such as by way of example only, a circular table, can comprise a single circular or other shaped exhaled air collector that is subdivided into individual (or group of individuals) sections that connects to a shared exhaled air suction conduit, such as a central exhaled air suction conduit. A single exhaled air collector can be of a circular design. A single circular exhaled air collector can comprise multiple sections, each section for positioning in front of an individual or group of individuals.

An exhaled air collector that collects exhaled air from multiple individuals can comprise multiple separated air suction intakes; in cases, more than one individual can have their own dedicated air suction intake. The multiple air suction intakes can connect to one common air suction conduit. The multiple air suction intakes can connect to one common air purification chamber. An air purification chamber can be supported by the table or desktop. An air purification chamber can be attached to the top of a desktop or tabletop. An air purification chamber can be attached to the underside of a tabletop or desktop. An air purification chamber can be located beneath the table or desktop. An air purification chamber can be remote to the table or desk. A conduit can be attached to the table or desktop. A conduit can pass through the table or desktop. An air suction intake can be covered with one or more of a mesh, screen, or grate. The exhaled air collector can comprise an adjustable exhaled air guide. An exhaled air collector that collects the exhaled air of multiple individuals can comprise multiple individually adjustable exhaled air guides. An exhaled air collector that collects the exhaled air of multiple individuals can comprise one adjustable exhaled air guide. An exhaled air collector that collects the exhaled air of multiple individuals can comprise one or more fixed exhaled air guides.

A musical note stand can support an exhaled air collector. A microphone stand can support an exhaled air collector. A desk can support an exhaled air collector. A table can support an exhaled air collector. A seat, chair, or bench can support an exhaled air collector.

By way of example only, exhaled air includes, but is not limited to, breath, breathing, yawning, sighing, talking, laughing, coughing, sneezing, speaking, screaming, crying, singing, exhaling, exhaling a breath of air, exhaling air when playing a musical instrument, blowing, forcing out air, and variations thereof.

Figure 40:
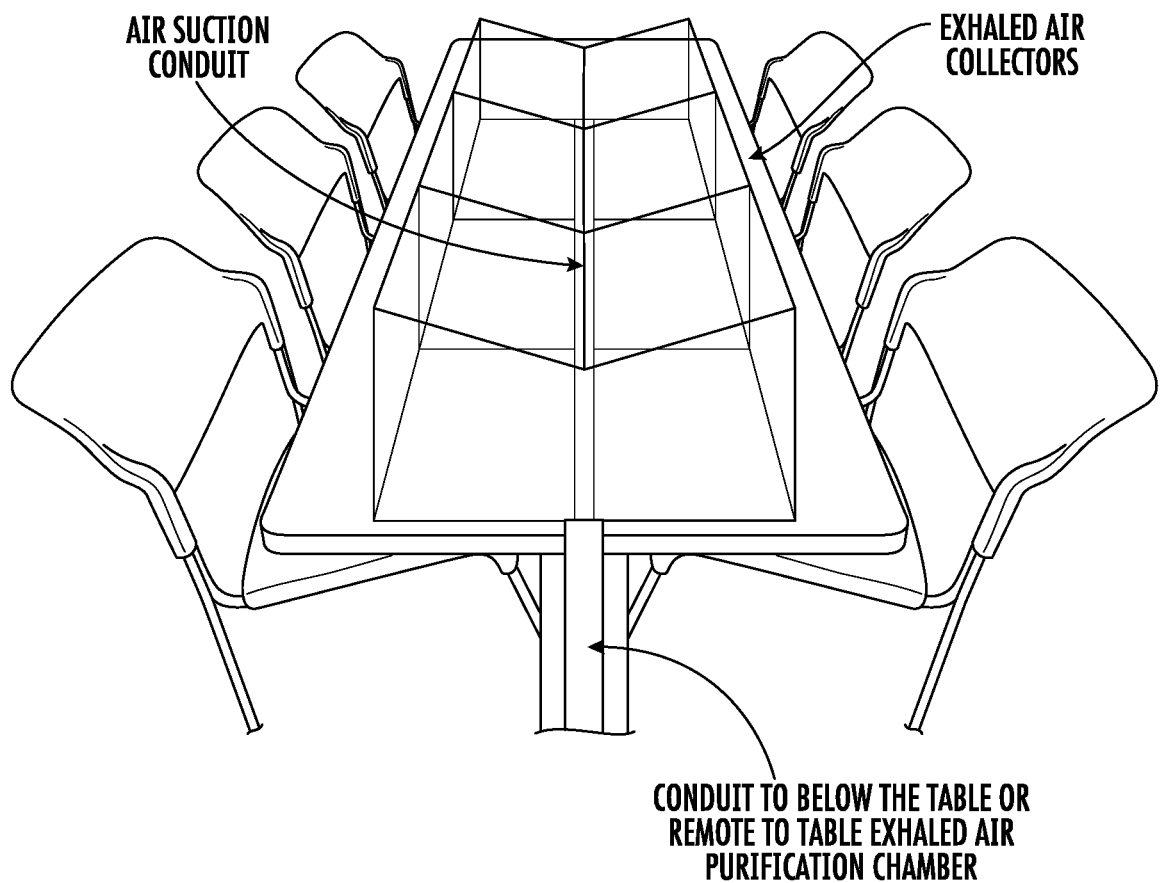
FIG. 40 is a drawing of a possible embodiment according to the present invention showing multiple exhaled air collectors connected to an air suction conduit leading to an air purification chamber. In aspects, the air suction conduit can lead to an air purification chamber on the tabletop, on the underside of the tabletop, under a table or remote from the table.
Figure 41:
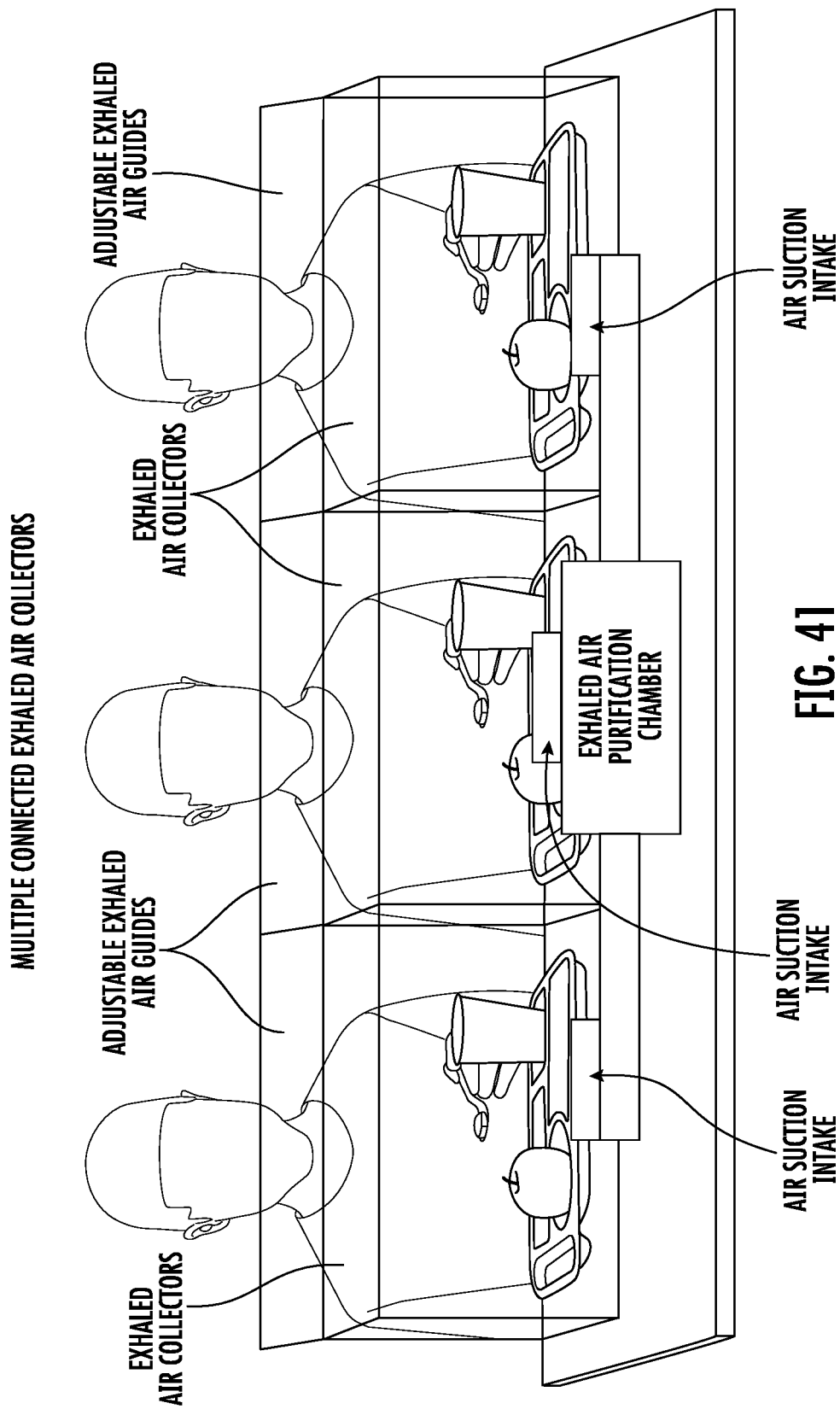
FIG. 41 is a drawing of a possible embodiment according to the present invention showing multiple exhaled air collectors, which may be connected or adjacent, and which multiple exhaled air collectors each include an air suction intake, which can lead to an exhaled air purification chamber.
Figure 42:
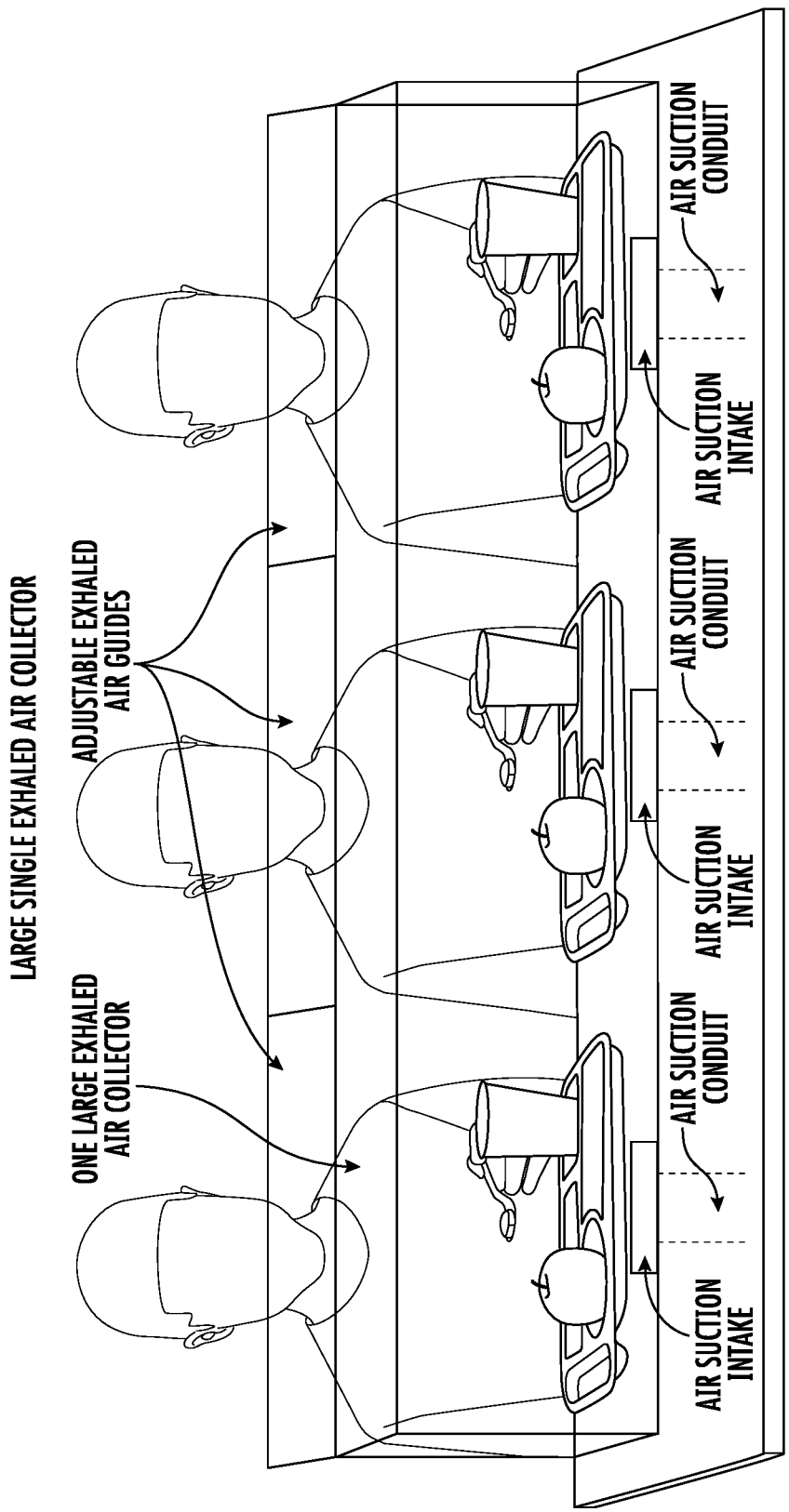
FIG. 42 is a drawing of a possible embodiment according to the present invention showing a single exhaled air collector with multiple air suction intakes leading to several air suction conduits which may lead to an air purification chamber. This figure also shows adjustable exhaled air guides. An exhaled air guide can be used to deflect a portion of exhaled air into the exhaled air collector. In aspects, a single exhaled air collector meant for use by more than one person at the same time can include one or more exhaled air guides, one or more shared air suction intake, one or more shared air suction conduit, and/or one or more shared air purification chamber.

For example, FIG. 40 shows multiple exhaled air collectors connected to an air suction conduit leading to an air purification chamber. In aspects, the air suction conduit can lead to an air purification chamber under the tabletop or remote from the table. FIG. 41 shows multiple exhaled air collectors, which may be connected or adjacent, and which multiple exhaled air collectors each include an air suction intake, which leads and an exhaled air purification chamber. FIG. 42 shows a single exhaled air collector with multiple air suction intakes leading to several air suction conduits which may lead to an air purification chamber. This figure also shows adjustable exhaled air guides. In aspects, a single exhaled air collector meant for use by more than one person at the same time can include one or more shared air suction intake, one or more shared air suction conduit, and/or one or more shared air purification chamber.

In embodiments, the exhaled air collector can be located within 2 inches to 6 feet of the individual's face exhaling air. In embodiments the exhaled air collector can be located within 1 foot to 6 feet of the individual's face exhaling air. In embodiments the exhaled air collector can be located within 2 feet to 6 feet of the individual's face exhaling air. In embodiments the exhaled air collector can be located within 3 feet to 6 feet of the individual's face exhaling air. In embodiments, the exhaled air collector comprises a top, an optional bottom, a back, and two sides. In embodiments the exhaled air collector comprises a top, an optional bottom, a back, two sides, and a partially or completely open front facing a person or persons. In embodiments the exhaled air collector comprises a top, an optional bottom, two sides, and a partially or completely open front facing a person or persons. In embodiments the exhaled air collector comprises a back, two sides, and a partially or completely open front facing a person or persons. In embodiments the exhaled air collector comprises a top, optional bottom, back, one side, and a partially or completely open front facing a person or persons. In embodiments the exhaled air collector comprises a top, back, two sides, and a partially or completely open front facing a person or persons. In embodiments, the exhaled air collector can comprise an exhaled air blocking surface. In embodiments, the exhaled air collector can be located within an arc of 45 degrees in front of a person whose exhaled air is being collected.

In another embodiment, the present invention can be a mobile wearable or carrying apparatus, by way of example only, a backpack, briefcase, valise, purse, wallet, luggage, or any other mobile wearable or carrying apparatus which can be converted into an air collector. For example, a mobile wearable or carrying apparatus can comprise a flexible and/or foldable flap or flaps that can fold or otherwise be deployed to become an exhaled air collector. The mobile wearable or carrying apparatus can also comprise one or more air suction intakes, one or more air suction conduits, and/or one or more air purification chambers. In other aspects, the mobile wearable or carrying apparatus after being removed from the wearer and set in place as an exhaled air collector can be connected to one or more air suction intakes, one or more air suction conduits, and/or one or more air purification chambers that is not contained in, within, or on the mobile wearable or carrying apparatus. For example, a hose or other connection mechanism could be deployed from the mobile wearable or carrying apparatus and connected to one or more air suction intakes, one or more air suction conduits, and/or one or more air purification chambers. The mobile wearable or carrying apparatus can be transparent. The mobile wearable or carrying apparatus can be flexible.

In embodiments, the air purification unit can comprise one or more speakers located, for example, within, on, or attached to an exhaled air collector for listening to, by way of example only, a teacher or lecturer. In embodiments, the air purification unit can comprise a transmitter located, for example, within, on or attached to an exhaled air collector for communicating with, by way of example only, a teacher or lecturer.

Figure 43:
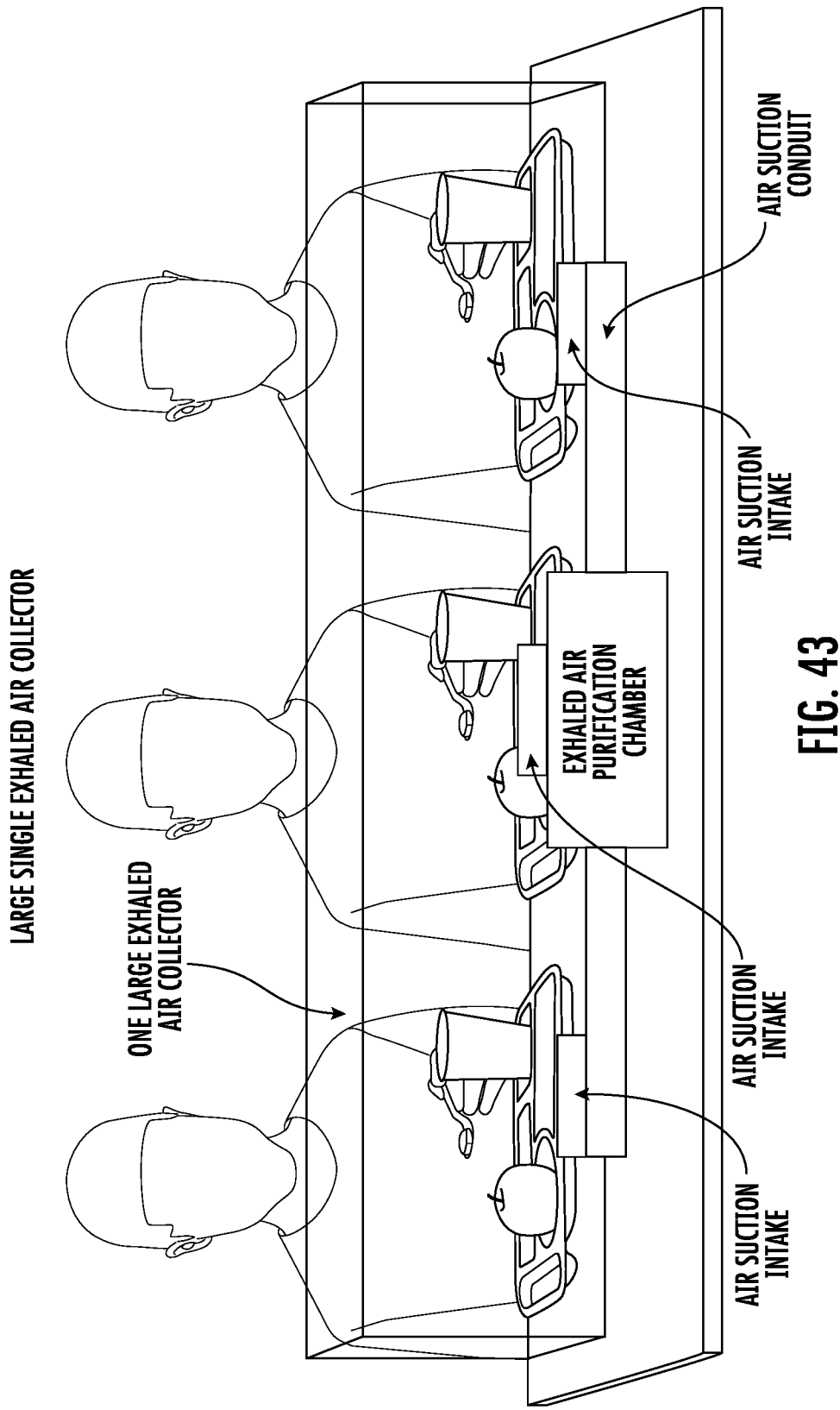
FIG. 43 is a drawing of a possible embodiment according to the present invention showing a single exhaled air collector with multiple air suction intakes leading to a shared air suction conduit that leads to an air purification chamber. In aspects, a single exhaled air collector can include one air suction intake for each person sharing the exhaled air collector.

Moving on to additional figures, FIG. 43 is a drawing of a possible embodiment according to the present invention showing a single exhaled air collector with multiple air suction intakes leading to a shared air suction conduit that leads to an air purification chamber. In aspects, a single exhaled air collector can include one air suction intake for each person sharing the exhaled air collector.

Figure 44:
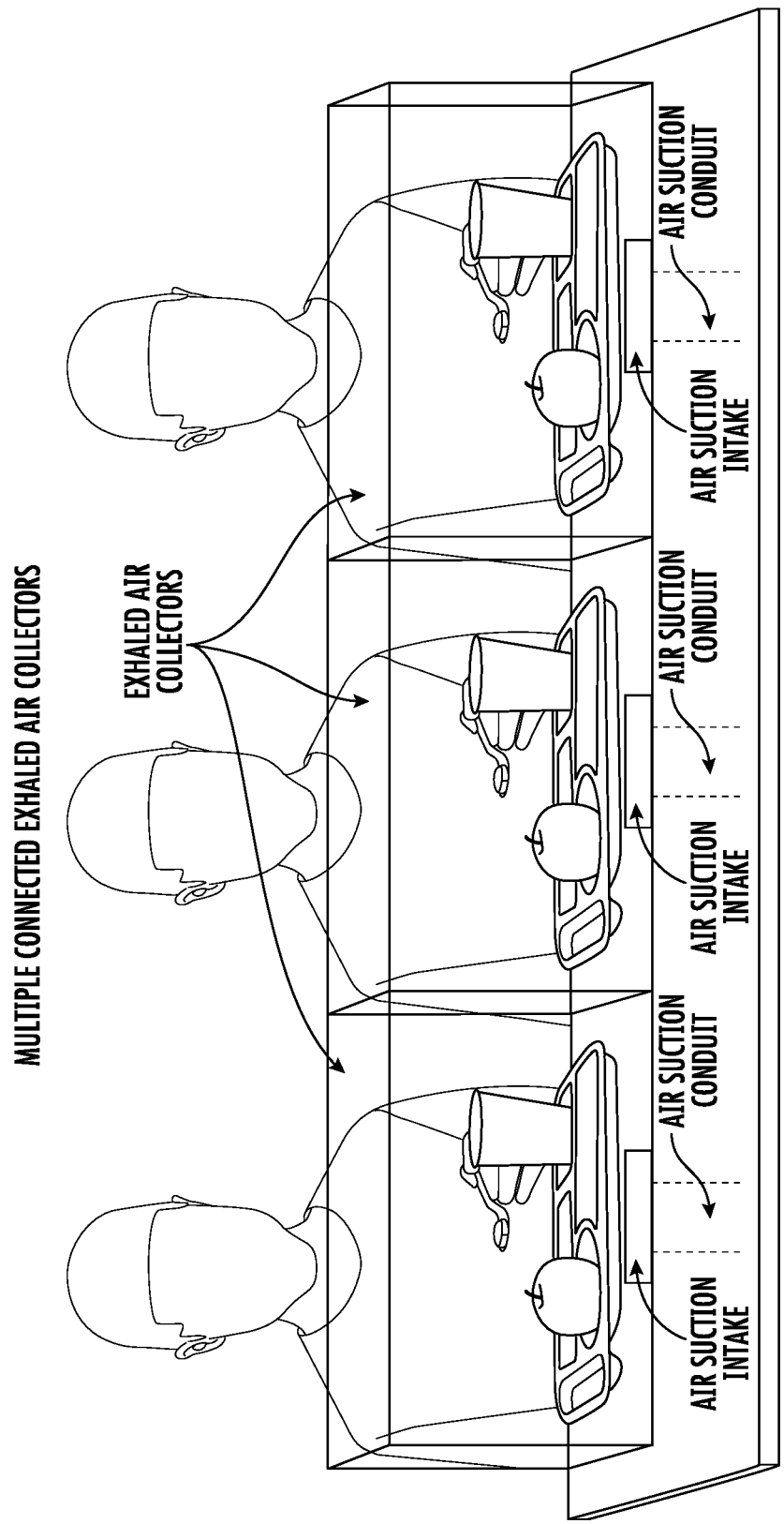
FIG. 44 is a drawing of a possible embodiment according to the present invention showing multiple connected or adjacent exhaled air collectors, each with its own air suction intake and air suction conduit, which may lead to an air purification chamber or several air purification chambers. In this Application, an "air purification chamber" and "exhaled air purification chamber" mean the same thing. In this Application, when an exhaled air collector, air suction intake, and/or air suction conduit are said to lead or otherwise connect to an air purification chamber, it is meant that they can lead to one or more air purification chambers.

FIG. 44 is a drawing of a possible embodiment according to the present invention showing multiple connected or adjacent exhaled air collectors, each with its own air suction intake and air suction conduit, which may lead to an air purification chamber or several air purification chambers. In this Application, an "air purification chamber" and "exhaled air purification chamber" mean the same thing. In this Application, when an exhaled air collector, air suction intake, and/or air suction conduit are said to lead or otherwise connect to an air purification chamber, it is meant that they can lead to one or more air purification chambers.

Figure 45A:
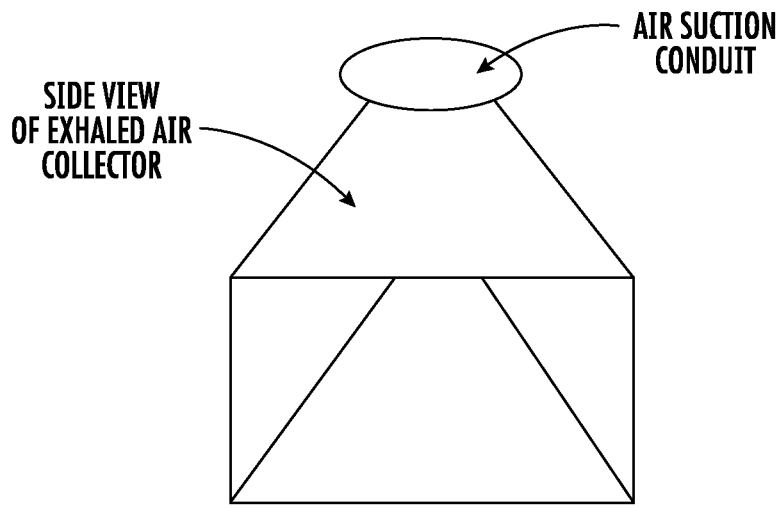
FIGS. 45A and 45B—FIG. 45A is a side view drawing of an exhaled air collector, along with an accompanying air suction conduit.
Figure 45B:
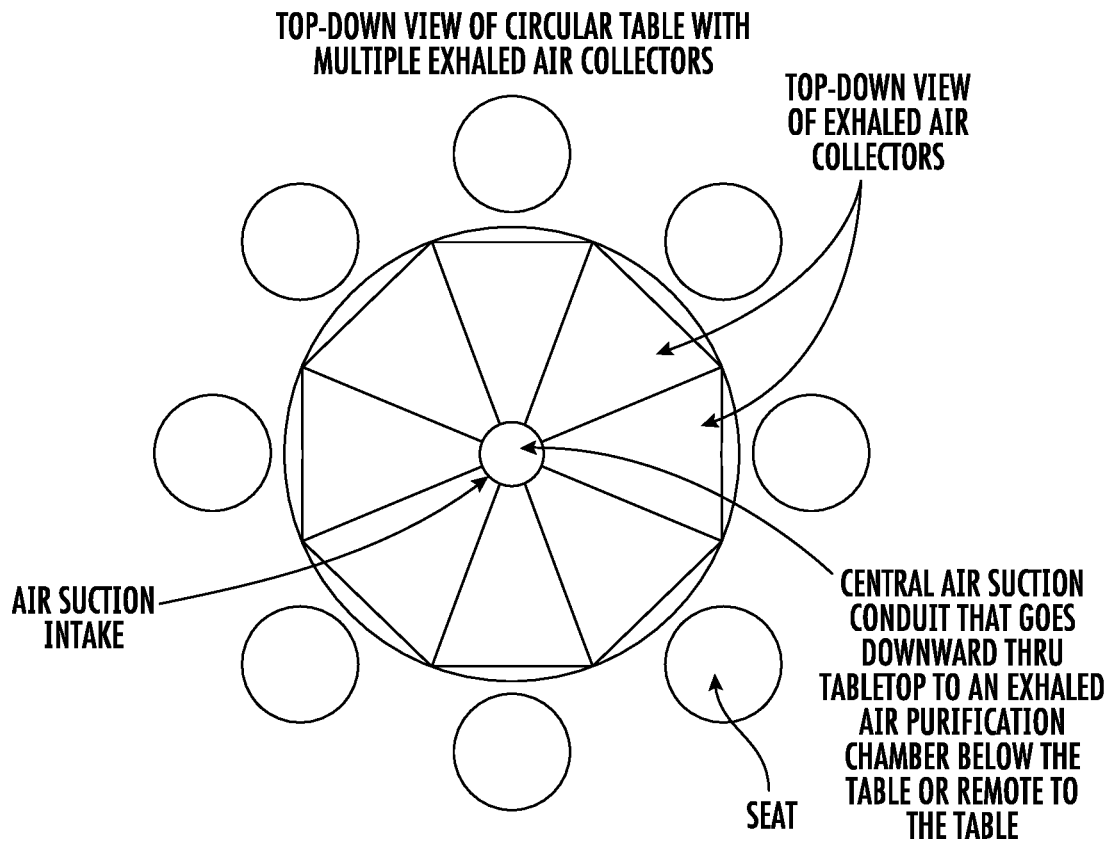

FIG. 45B is a drawing of a possible embodiment according to the present invention showing a top-down view of a table comprising multiple exhaled air collectors and a central air suction conduit that lead downwards through the tabletop and to an air purification chamber below the table or remote to the table. In this embodiment, there may be a shared air section intake(s), or separate air suction intakes for each or several exhaled air collectors. In aspects of the current invention, one or more exhaled air collectors may share an air suction intake, an air suction conduit, and/or an air purification chamber. While not illustrated a central air suction conduit can rise upward from the tabletop or desktop connecting to a remote exhaled air purification chamber. In FIG. 45A, a side view of an exhaled air collector is also shown, along with an accompanying air suction conduit.

Figure 46:
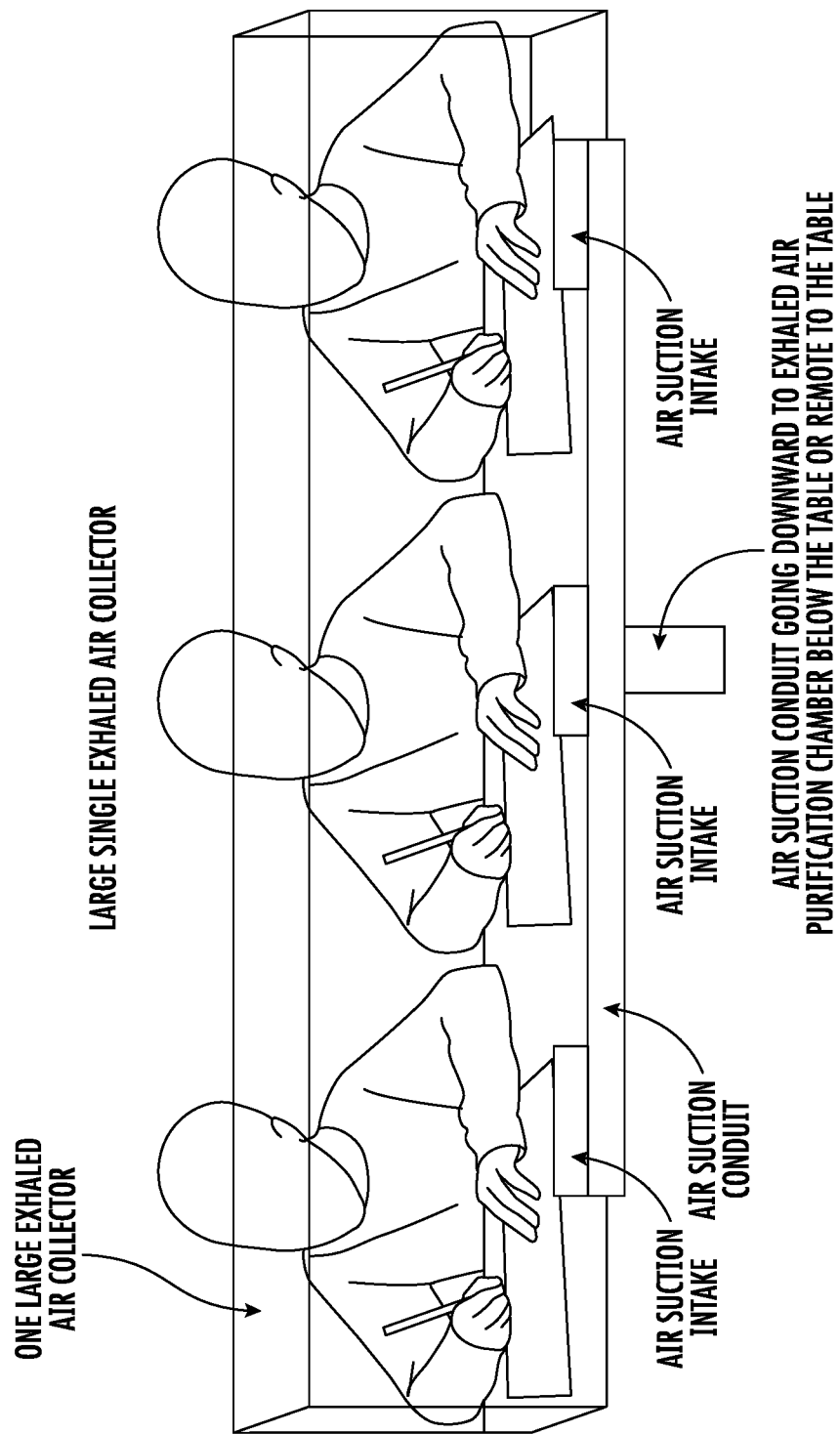
FIG. 46 is a drawing of a possible embodiment according to the present invention showing a single exhaled air collector with several air suction intakes leading to a single or shared air suction conduit which may lead downwards to an exhaled air purification chamber below the table or remote to the table.

FIG. 46 is a drawing of a possible embodiment according to the present invention showing a single exhaled air collector with several air suction intakes leading to a single or shared air suction conduit which may lead downwards to an exhaled air purification chamber below the table, under the tabletop or remote to the table.

Figure 47:
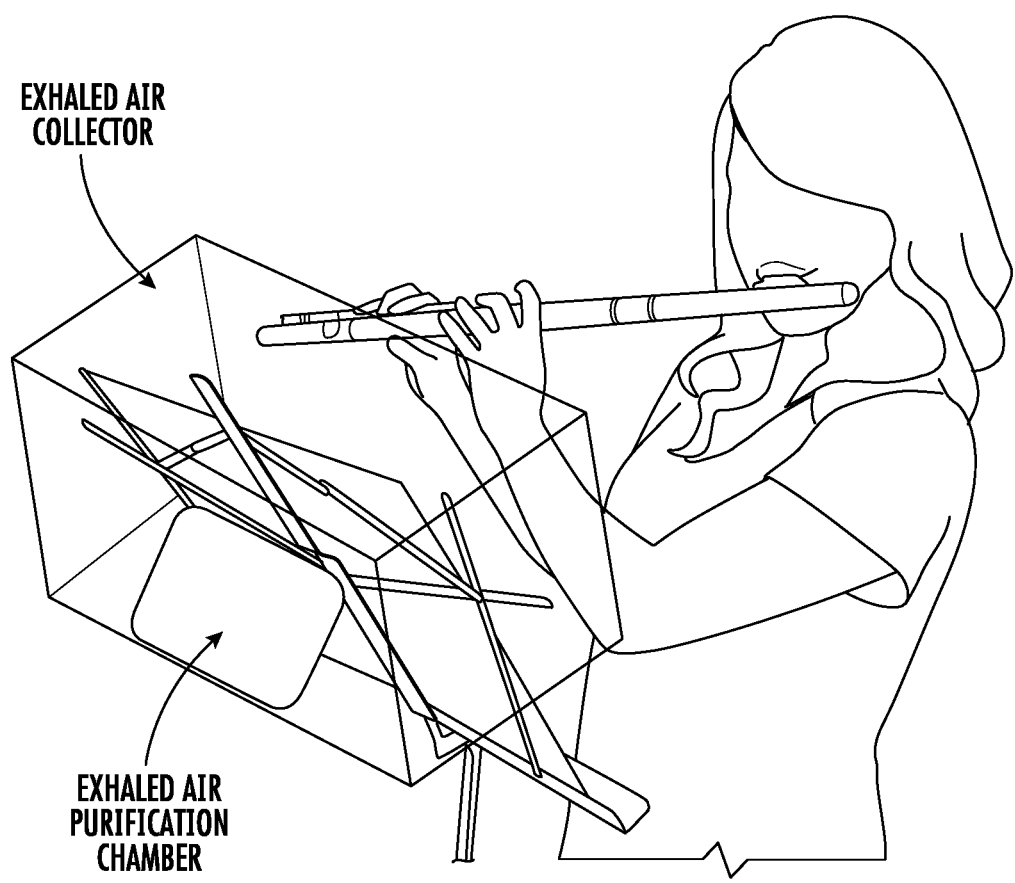
FIG. 47 is a drawing of a possible embodiment according to the present invention showing a single exhaled air collector with a connected or adjacent exhaled air purification chamber. In this embodiment, the exhaled air collector has an open front facing or substantially facing a musician or singer to capture exhaled air.

FIG. 47 is a drawing of a possible embodiment according to the present invention showing a single exhaled air collector with a connected or adjacent exhaled air purification chamber. In this embodiment, the exhaled air collector has an open front facing or substantially facing a musician or singer to capture exhaled air.

Figure 48:
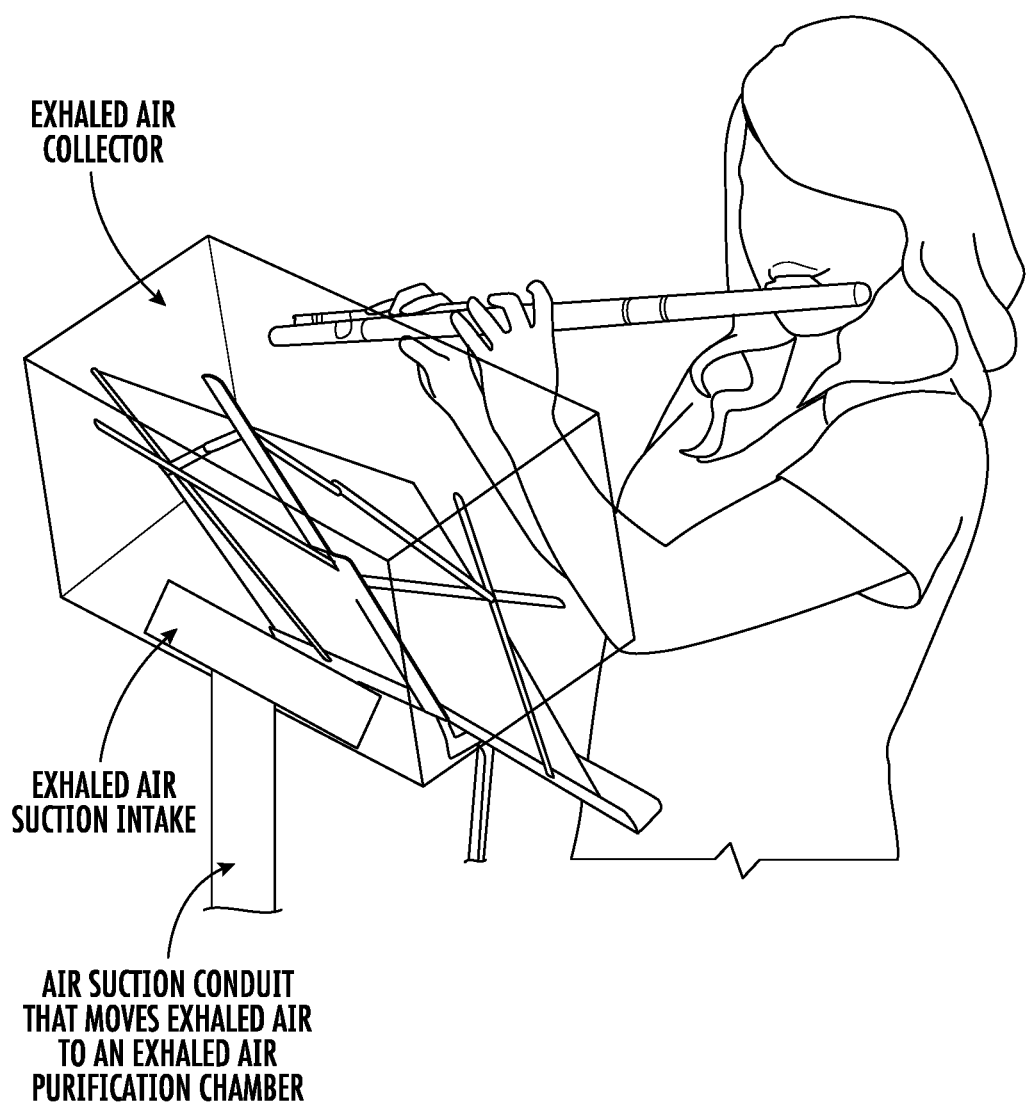
FIG. 48 is a drawing of a possible embodiment according to the present invention showing a single exhaled air collector with an exhaled air suction intake leading to an air suction conduit that moves or allows exhaled air to move to an exhaled air purification chamber. In this embodiment, the exhaled air collector has an open front facing or substantially facing a musician or singer to capture exhaled air.

FIG. 48 is a drawing of a possible embodiment according to the present invention showing a single exhaled air collector with an exhaled air suction intake leading to an air suction conduit that moves or allows exhaled air to move to an exhaled air purification chamber. In this embodiment, the exhaled air collector has an open front facing or substantially facing a musician or singer to capture exhaled air.

Figure 49:
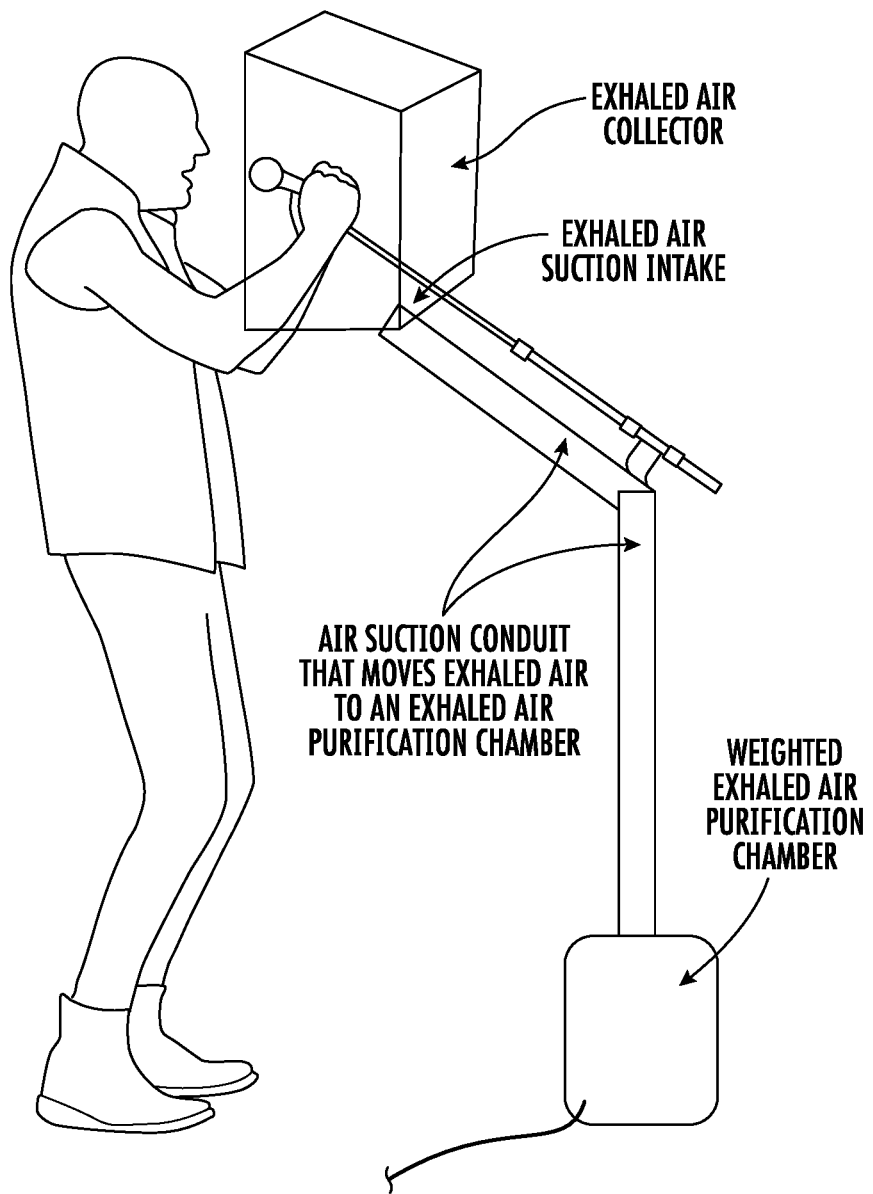
FIG. 49 is a drawing of a possible embodiment according to the present invention showing a single exhaled air collector with an exhaled air suction intake leading to an air suction conduit that moves or allows exhaled air to move to an exhaled air purification chamber, such as a downstream weighted exhaled air purification chamber. In this embodiment, the exhaled air collector has an open front facing or substantially facing a musician or singer to capture exhaled air, and in aspects the exhaled air collector is capable of including a microphone partially or completely within the exhaled air collector.

FIG. 49 is a drawing of a possible embodiment according to the present invention showing a single exhaled air collector with an exhaled air suction intake leading to an air suction conduit that moves or allows exhaled air to move to an exhaled air purification chamber, such as a downstream weighted exhaled air purification chamber. In this embodiment, the exhaled air collector has an open front facing or substantially facing a musician or singer to capture exhaled air, and in aspects the exhaled air collector is capable of including a microphone partially or completely within the exhaled air collector.

Figure 50:
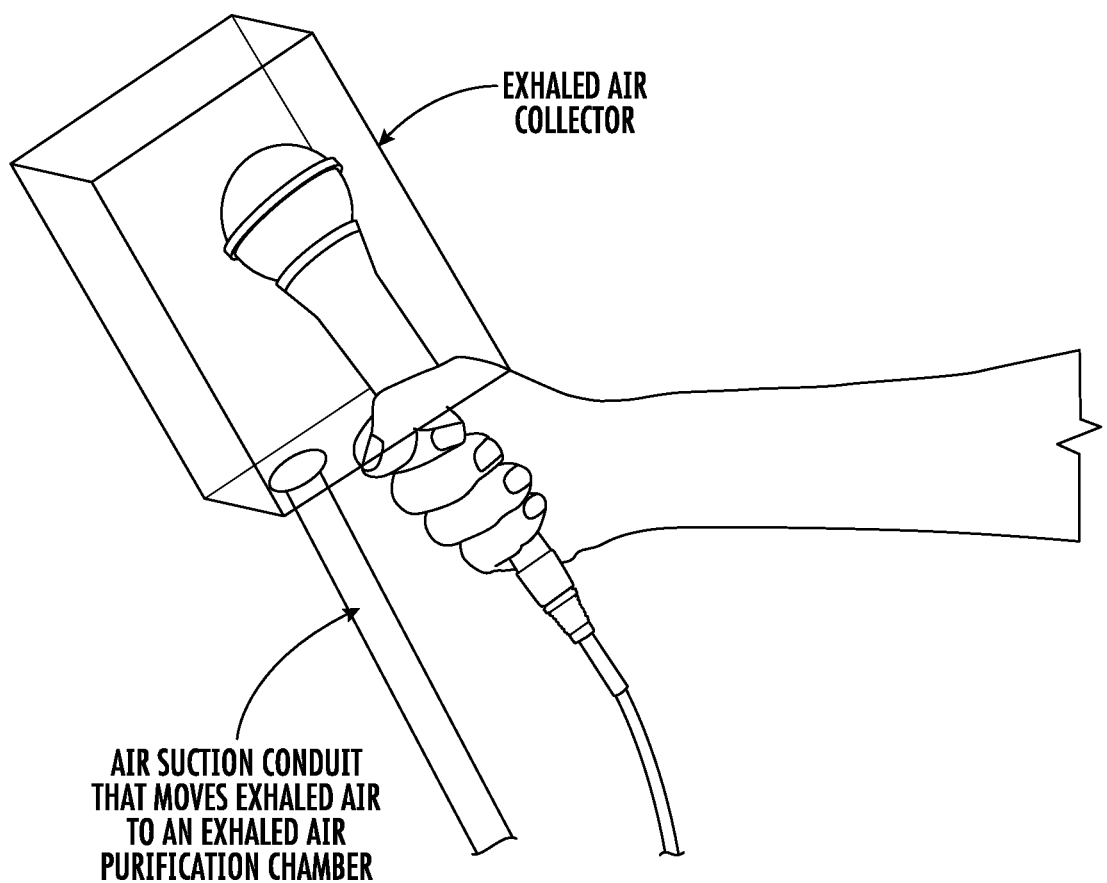
FIG. 50 is a drawing of a possible embodiment according to the present invention showing a single exhaled air collector with an exhaled air suction conduit that moves or allows exhaled air to move to an exhaled air purification chamber. In this embodiment, the exhaled air collector has an open front facing or substantially facing a musician or singer to capture exhaled air, and in aspects the exhaled air collector is capable of including a microphone partially or completely within the exhaled air collector. In aspects, the exhaled air collector can be portable and/or moved around while in use.

FIG. 50 is a drawing of a possible embodiment according to the present invention showing a single exhaled air collector with an exhaled air suction conduit that moves or allows exhaled air to move to an exhaled air purification chamber. In this embodiment, the exhaled air collector has an open front facing or substantially facing a musician or singer to capture exhaled air, and in aspects the exhaled air collector is capable of including a microphone partially or completely within the exhaled air collector. In aspects, the exhaled air collector can be portable and/or moved around while in use.

Figure 51:
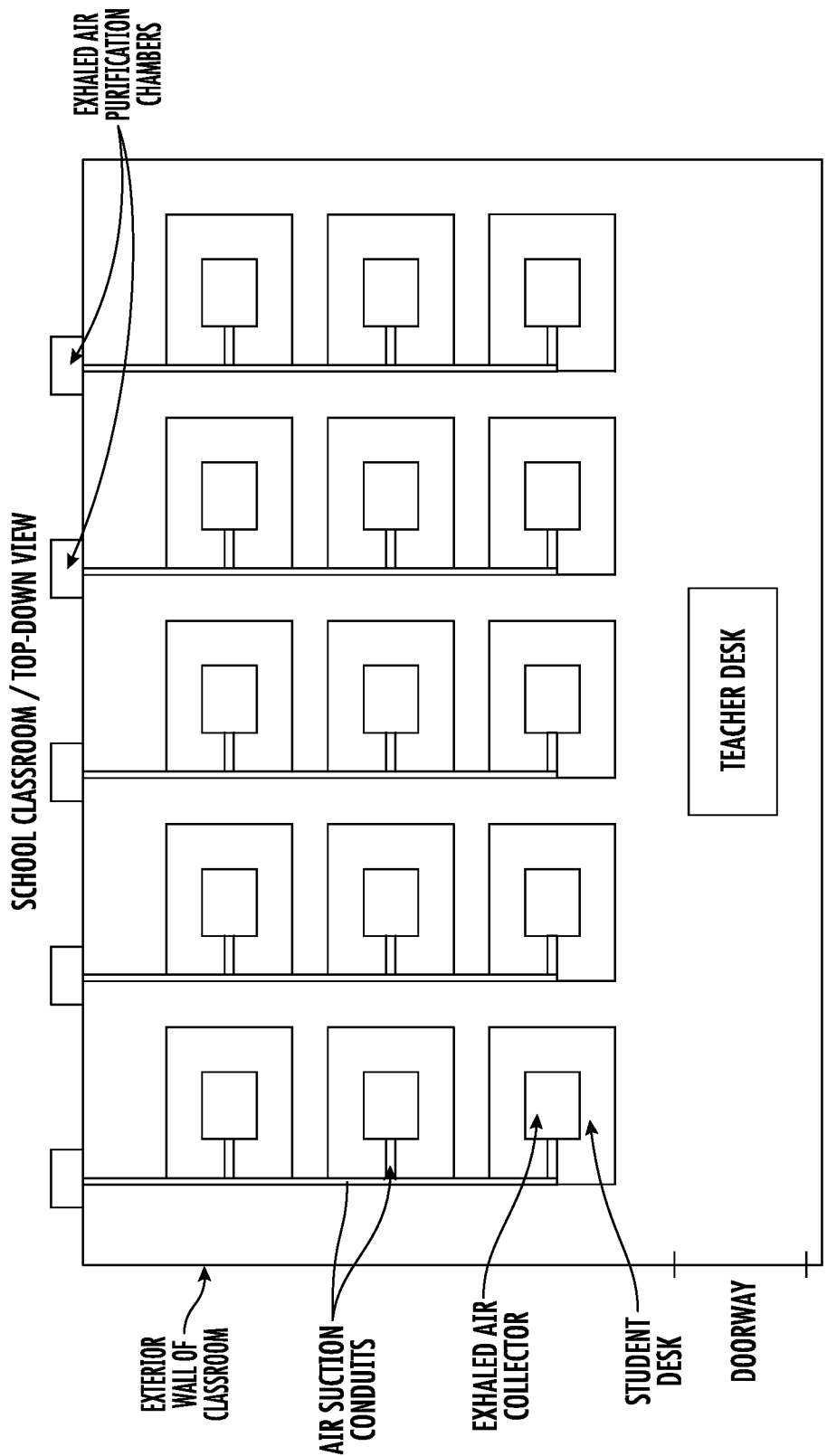
FIG. 51 is a top-down drawing of a possible embodiment according to the present invention showing multiple exhaled air collectors connected to, such as by way of a conduit, a shared exhaled air purification chamber. In aspects, several of these multiple exhaled air collectors connected to an air purification can exist in the same room, venue, or environment.

FIG. 51 is a top-down drawing of a possible embodiment according to the present invention showing multiple exhaled air collectors connected to, such as by way of a conduit, a shared exhaled air purification chamber. In aspects, several of these multiple exhaled air collectors connected to an air purification can exist in the same room, venue, or environment. For example, in a classroom setting, each desk could include its own exhaled air collector connected to an air suction conduit. Several exhaled air collectors can lead to a connected air purification chamber, and in cases the air purification chamber can be connected to the exhaled air collectors by way of an air suction conduit. As shown in the figure, the air purification chamber can be located remotely from one or more desks, such as in the back of the classroom or outside of the classroom. In aspects, an air suction conduit can leave one or more of the top, side, back, or bottom of the desk; an air suction conduit can leave the top, side, back, or bottom of the exhaled air collector and an air suction conduit could, in examples, run over, under, or through a floor or wall. Such an embodiment could be used in, by way of example, a classroom, office(s), conference room, amphitheater, cafeteria, or otherwise. The word desk or table can include a desktop or a tabletop.

The present invention relates to various multi-seated indoor environments or venues. Such venues include, by way of example only, theaters of all kinds, vehicles of all types, school and university classrooms, and workplaces. The present invention can more broadly apply in all multi-seated venues such as, by way of example only, workplaces, classrooms, conference rooms, schools, universities, vehicles (land, sea and air) (e.g., aircraft, airplanes, jets, boats, ships, cars, automobiles, trucks, trains, subways, buses, etc.), theaters (e.g., auditoriums, educational, sports, performing arts, cinema, etc.), and houses of worship (e.g., churches, synagogues, temples, etc.). The present invention especially applies in locations where multiple individuals can sit at desks or tables, and/or they can stand when utilizing desks or tables.

An embodiment of the invention is that of an exhaled air purification unit, wherein the air purification unit comprises an exhaled air collector that has an open front and an exhaled air purification chamber. The exhaled air purification chamber can be one of: directly attached to the exhaled air collector, adjacent to the exhaled air collector, indirectly connected by way of a conduit, fully housed within the exhaled air collector, or partially housed within the exhaled air collector. In certain other embodiments the front of the exhaled air collector is covered with a grill, screen, or grate.

Figure 2:
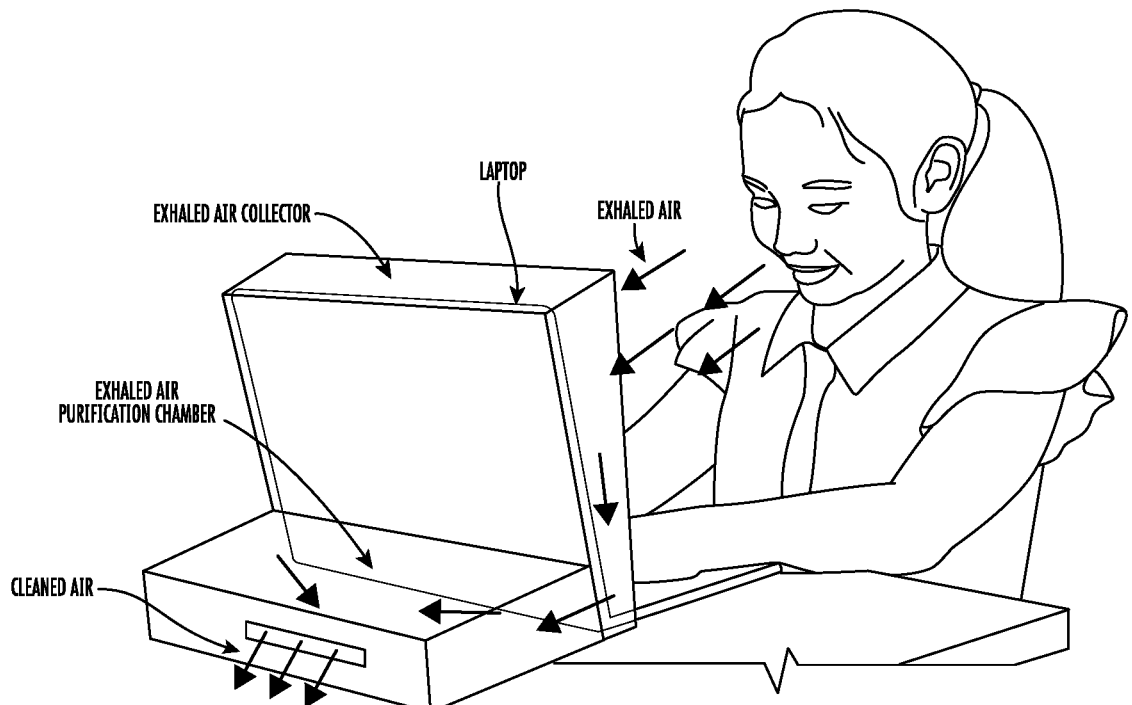
FIG. 2 is a drawing of a possible embodiment according to the present invention showing an air purification unit.
Figure 3:
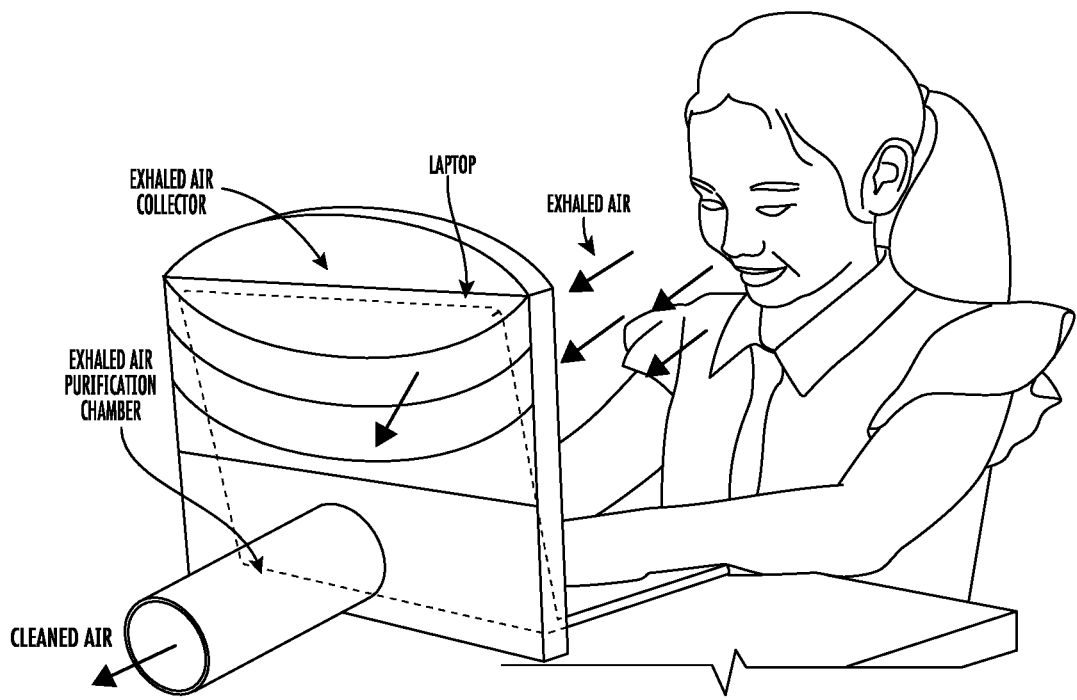
FIG. 3 is a drawing of a possible embodiment according to the present invention showing an air purification unit.

For example, in FIG. 2, exhaled air from a human in front of the exhaled air collector comprising an opening in the front (towards the human) wherein exhaled air is collected and sent to the attached exhaled air purification chamber and then cleaned and/or filtered air is exhausted passively or actively from the unit. In this case a laptop computer is partially located within the exhaled air collector. The arrows indicated exhaled air and cleaned air leaving the device. Similarly, FIG. 3 shows exhaled air from a human in front of the exhaled air collector comprising an opening in the front (towards the human) wherein exhaled air is collected and sent to the attached exhaled air purification chamber and then cleaned and/or filtered air is exhausted passively or actively from the unit. In the embodiment in FIG. 3 the air purification chamber is situated and shaped differently than in FIG. 2. In this case a laptop computer is partially located within the exhaled air collector. The arrows indicated exhaled air and cleaned air leaving the device.

Figure 4:
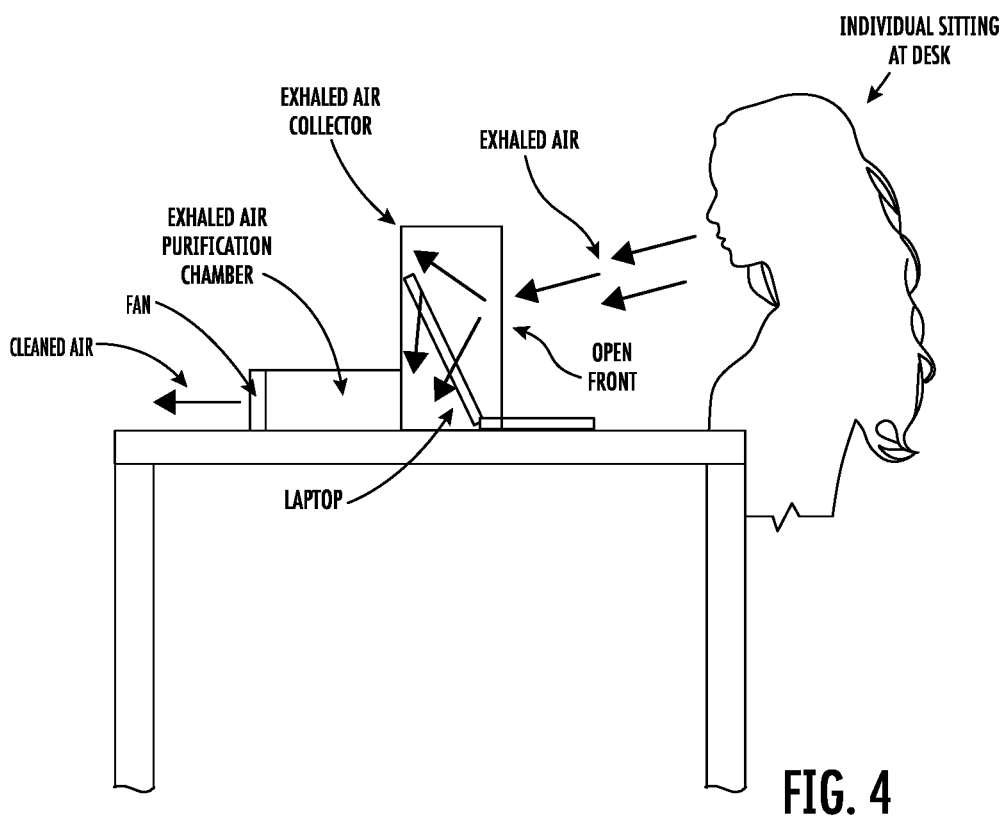
FIG. 4 is a side view drawing of a possible embodiment according to the present invention showing an air purification unit.

FIG. 4 shows an air purification unit embodiment from the side, wherein the human's exhaled air is shown by arrows going into the exhaled air collector. In this side view, it is shown where the opening on the front, user-facing side of the exhaled air collector has an opening that allows for entry of the exhaled air and in this case placement of a laptop computer. The exhaled air travels to the air purification chamber where it is cleaned and/or filtered and then the cleaned and/or filtered air leaves the air purification unit. In this embodiment a fan is used to help either or both suction air into the air purification chamber and send/exhaust cleaned and/or filtered air from the device and back into the environment from where it was collected.

Figure 5:
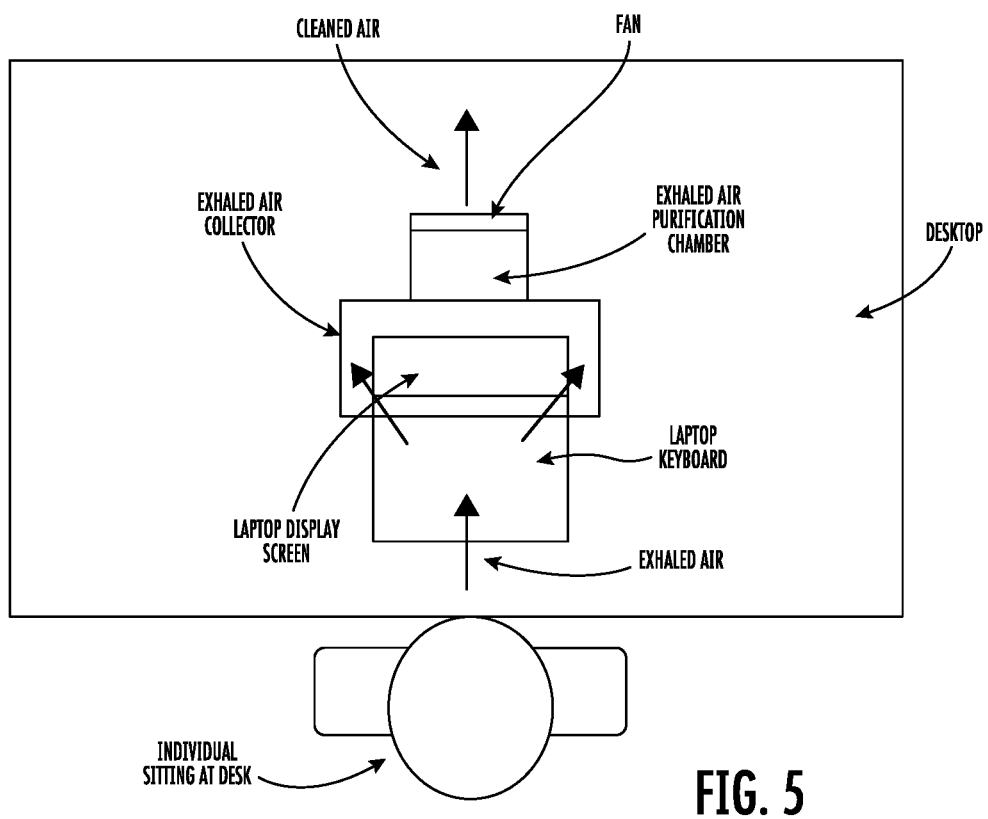
FIG. 5 is a top-looking-down view drawing of a possible embodiment according to the present invention showing an air purification unit.

FIG. 5 shows an air purification unit embodiment from a top-looking-down view over the top of a desk or table, wherein the human's exhaled air is shown by arrows going into the exhaled air collector. In this view, it is shown where the opening on the front, user-facing side of the exhaled air collector has an opening that allows for entry of the exhaled air and in this case placement of a laptop computer (see laptop screen with air collector and laptop keyboard extending outside). The exhaled air travels to the air purification chamber where it is cleaned and/or filtered and then the cleaned and/or filtered air leaves the air purification unit. In this embodiment a fan is used to help either or both suction air into the air purification chamber and send/exhaust cleaned and/or filtered air from the device and back into the environment from where it was collected.

In embodiments of the invention, when an exhaled air collector has an open front, the exhaled air collector can partially or fully house a visual display device. In certain embodiments the visual display device is partially or completely positioned within the exhaled air collector through the open front of the exhaled air collector. In certain embodiments the keyboard is located partially or completely outside of the exhaled air collector while, for example, a laptop screen is positioned (partially or fully) within the exhaled air collector. In other embodiments the visual display is attached or connected to the exhaled air collector. Such a visual display device can be, by way of example only, a display screen, a laptop computer, a desktop computer, a computer screen, a visual imaging projection device, a 3D projection screen, a 3D projection display device, a holographic display screen, a holographic display device, or a television.

Figure 26:
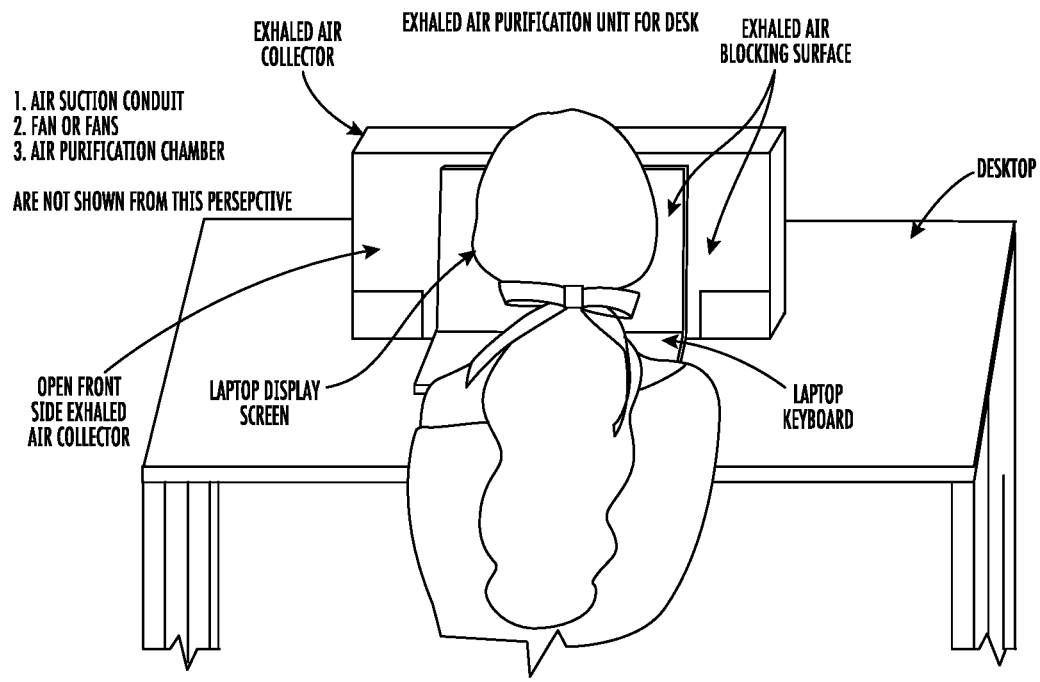
FIG. 26 is a drawing of a possible embodiment according to the present invention showing an air purification unit from the perspective behind a user of the air purification unit.
Figure 27:
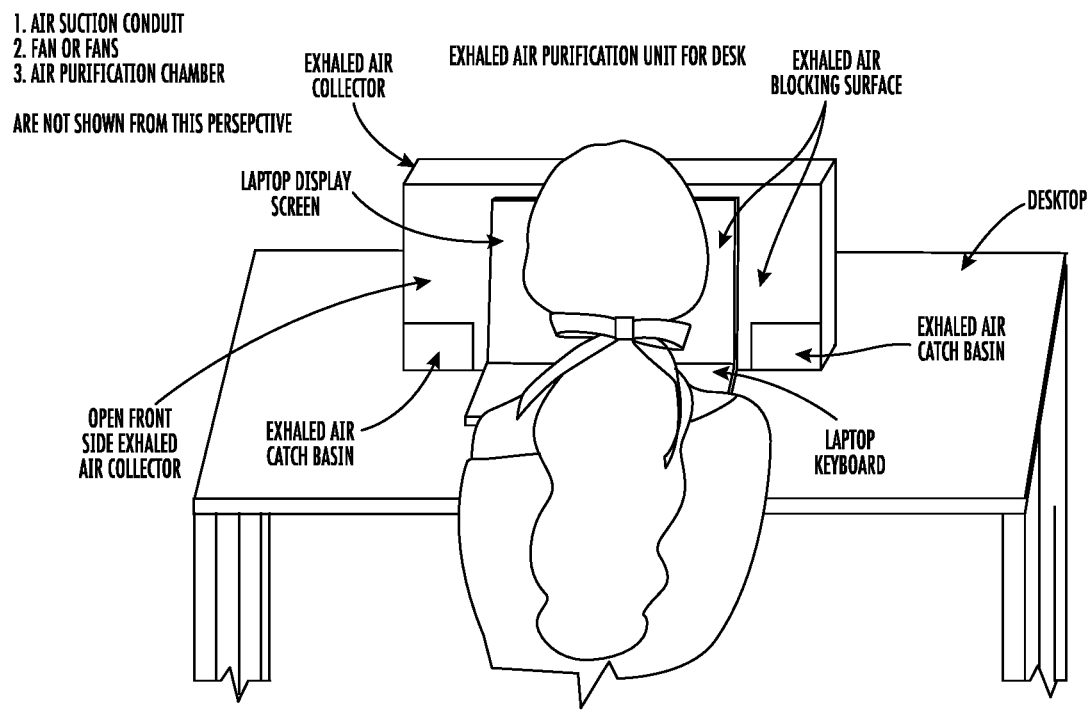
FIG. 27 is a drawing of a possible embodiment according to the present invention showing an air purification unit from the perspective behind a user of the air purification unit.
Figure 30:
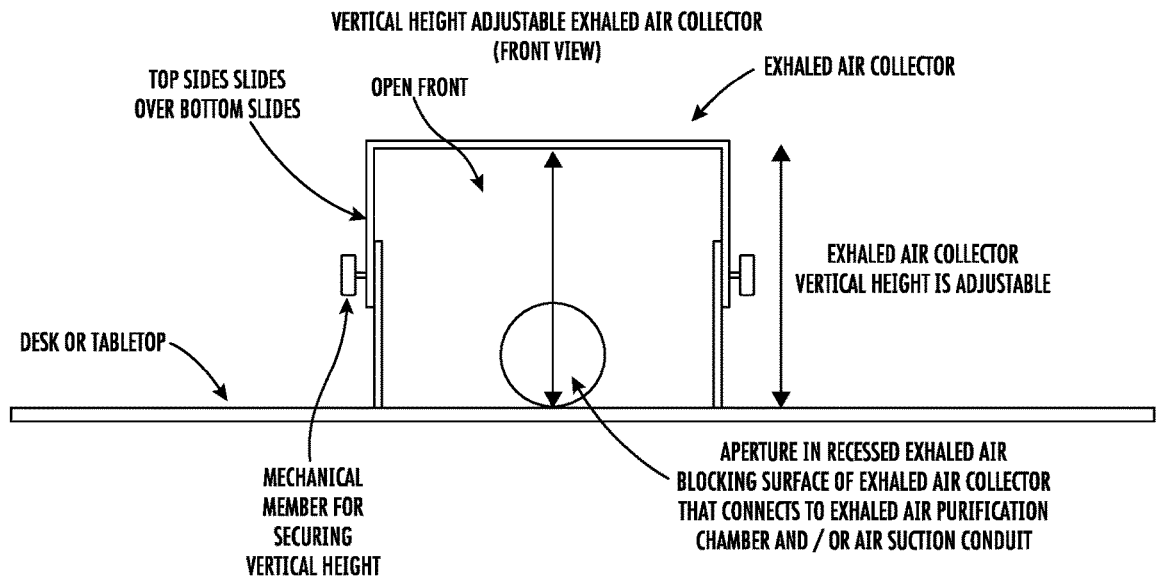
FIG. 30 is a front view drawing of a possible embodiment according to the present invention showing an air purification unit.
Figure 34:
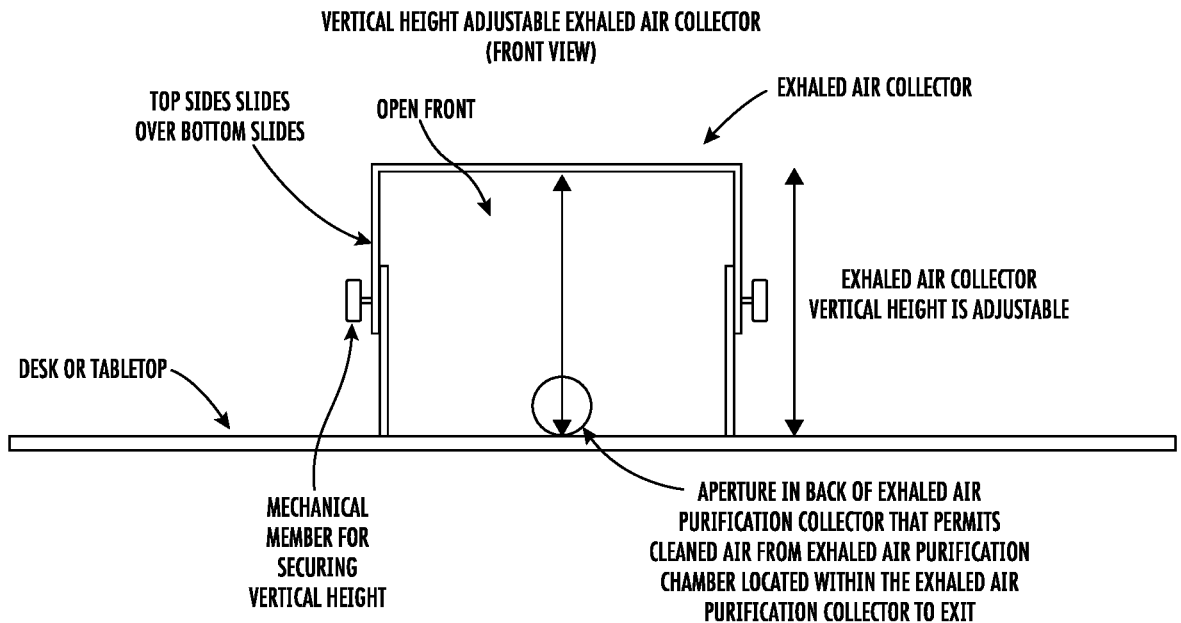
FIG. 34 is a front view drawing of a possible embodiment according to the present invention showing an air purification unit.

FIG. 26 shows an embodiment of the invention on a desktop or tabletop from a perspective behind the user, showing the open front side of the exhaled air collector and a laptop computer (laptop display screen and keyboard) partially or completely located within the opening and cavity of the exhaled air collector. The back of the air collector comprises an exhaled air blocking surface. Due to the perspective, other aspects, such as fans, an air suction conduit, and the air purification chamber are not shown. Similarly, FIG. 27 shows an embodiment of the invention on a desktop or tabletop from a perspective behind the user, showing the open front side of the exhaled air collector and a laptop computer (laptop display screen and keyboard) partially or completely located within the opening and cavity of the exhaled air collector. The back of the air collector can comprise an exhaled air blocking surface. This embodiment also shows exhaled air catch basins at, in, within, integrated into, placed, located, or near the bottom of the exhaled air collector, as described herein. Due to the perspective, other aspects, such as fans, an air suction conduit, and the air purification chamber are not shown. FIG. 30 shows an embodiment from a perspective of the user sitting or standing in front of the unit. The unit is shown on top of a desk or table and shows an open front of the exhaled air collector. An aperture in the recessed air blocking surface of the exhaled air collector connects to the exhaled air purification chamber and/or an air suction conduit. In aspects, the vertical height of the exhaled air collector is adjustable. In this embodiment a top side of the exhaled air collector slides over a bottom side and a mechanical member can be used for securing the vertical height. Similarly, FIG. 34 shows an embodiment from a perspective of the user sitting or standing in front of the unit. The unit is shown on top of a desk or table and shows an open front of the exhaled air collector. In this embodiment, an aperture in the back of the exhaled air purification chamber (and/or the back of the exhaled air collector) permits cleaned air from the exhaled air purification chamber located within the exhaled air purification collector to exit. In aspects, the vertical height of the exhaled air collector is adjustable. In this embodiment a top side of the exhaled air collector slides over a bottom side and a mechanical member can be used for securing the vertical height.

Another embodiment is that of an exhaled air purification unit, wherein the exhaled air purification unit comprises an exhaled air collector and an exhaled air purification chamber, wherein the exhaled air purification unit is supported by a desk or table, wherein the exhaled air collector comprises an opening on its front side, and wherein the exhaled air collector is connected to an exhaled air purification chamber by way of an aperture, such as an aperture within a wall, back, or bottom of the exhaled air collector. The aperture can be an air suction intake. The air suction intake can comprise a fan. The air suction intake can be covered with a grill, screen, or gate. The grill, screen, or grate can comprise a microbicidal agent or material. In certain embodiments the exhaled air collector can collect exhaled air of someone who is sitting or standing in front of the desk or table that supports the exhaled air collector. In this case the exhaled air collector can be resting upon the desk or tabletop. In certain embodiments the exhaled air collector can collect exhaled air of someone who is sitting in a seat behind that of a seat in front. In this case the exhaled air collector can be one of: attached to the back of the seat, incorporated within the back of the seat, or free standing within a support member that is distance separated and behind that of the back of the seat in front. The exhaled air collector can comprise an opening on its front side. The exhaled air collector can allow for all or a part of a laptop or desktop computer to be inserted within and removed. The exhaled air collector can be devoid of a computer. The exhaled air collector can be directly adjacent to an exhaled air purification chamber. The exhaled air collector can be connected to an exhaled air purification chamber. The exhaled air collector can house an exhaled air purification chamber. The exhaled air collector can partially house an exhaled air purification chamber. The exhaled air collector can support an exhaled air purification chamber. The exhaled air collector can be adjustable in one or more of its dimensions, including vertical, horizontal, or depth. The exhaled air purification chamber can connect by way of an air suction conduit to the exhaled air collector.

Figure 6:
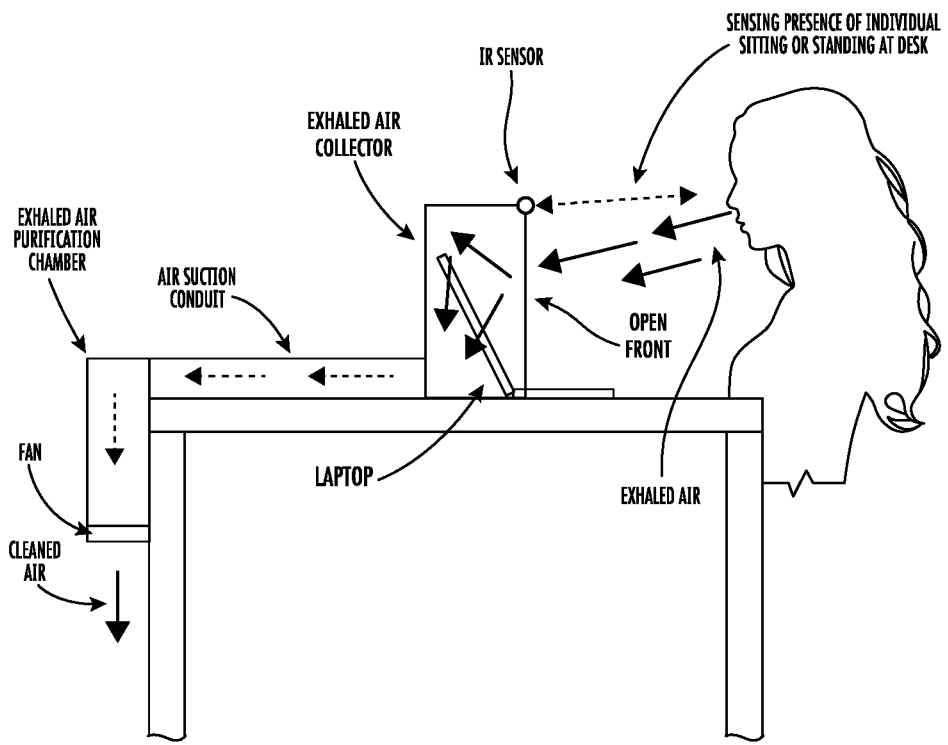
FIG. 6 is a side view drawing of a possible embodiment according to the present invention showing an air purification unit.
Figure 7:
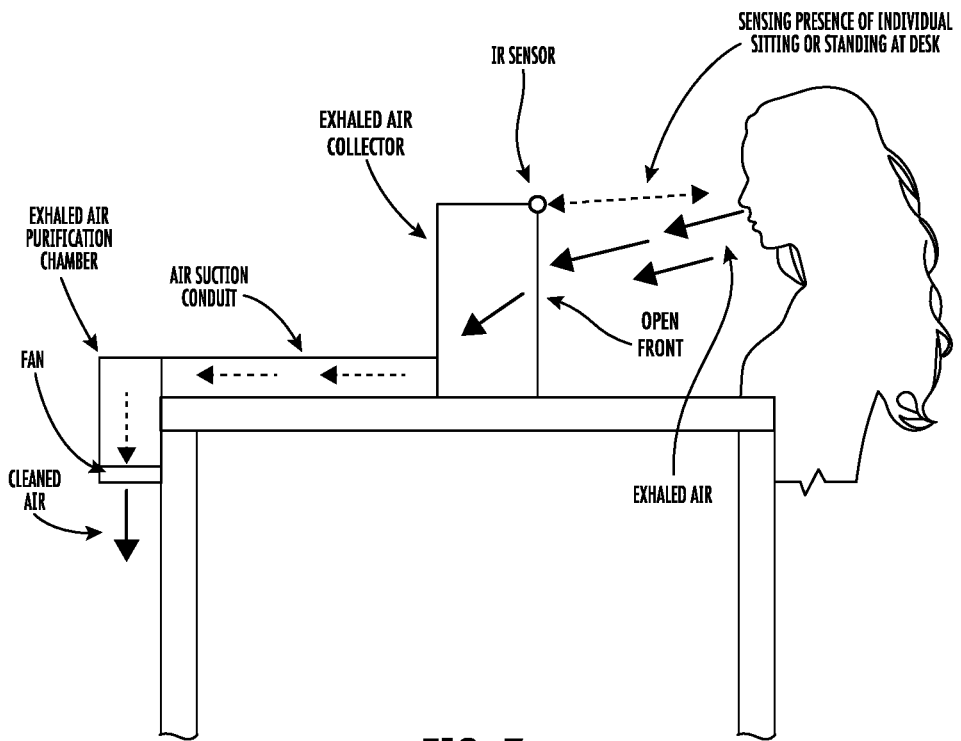
FIG. 7 is a side view drawing of a possible embodiment according to the present invention showing an air purification unit.
Figure 8:
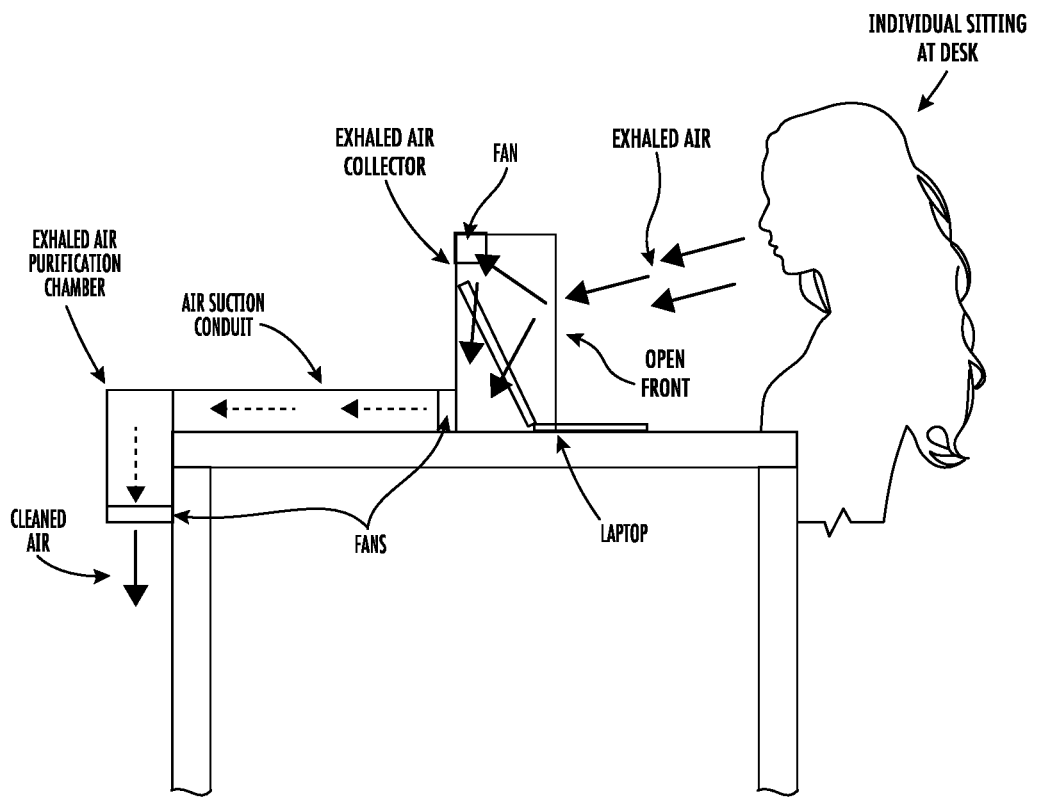
FIG. 8 is a side view drawing of a possible embodiment according to the present invention showing an air purification unit.

For example, in FIG. 6, an air purification unit embodiment is shown from the side, wherein the human's exhaled air is shown by arrows going into the exhaled air collector. In this side view, it is shown where the opening on the front, user-facing side of the exhaled air collector has an opening that allows for entry of the exhaled air and in this case placement of a laptop computer. The exhaled air travels to an air suction conduit connecting the exhaled air collector to the air purification chamber where it is cleaned and/or filtered and then the cleaned and/or filtered air leaves the air purification unit. In this embodiment a fan is used to help either or both suction air into the air purification chamber and send/exhaust cleaned and/or filtered air from the device and back into the environment from where it was collected. Also, in this embodiment a sensor is shown, such as an IR sensor, meant to sense the presence of a person sitting or standing at the desk or table. In aspects, when a person is sitting or standing in front of or near the unit the sensor will cause the unit to turn on. In aspects, when the person leaves the sensor will cause the unit to turn off. Similarly, in FIG. 7, an air purification unit embodiment is shown from the side, wherein the human's exhaled air is shown by arrows going into the exhaled air collector. In this side view, it is shown where the opening on the front, user-facing side of the exhaled air collector has an opening that allows for entry of the exhaled air and in this case, there is no laptop computer. The exhaled air travels to an air suction conduit connecting the exhaled air collector to the air purification chamber where it is cleaned and/or filtered and then the cleaned and/or filtered air leaves the air purification unit. In this embodiment a fan is used to help either or both suction air into the air purification chamber and send/exhaust cleaned and/or filtered air from the device and back into the environment from where it was collected. Also, in this embodiment a sensor is shown, such as an IR sensor, meant to sense the presence of a person sitting or standing at the desk or table. In aspects, when a person is sitting or standing in front of or near the unit the sensor will cause the unit to turn on. In aspects, when the person leaves the sensor will cause the unit to turn off. FIG. 8 shows an air purification unit embodiment from the side, wherein the human's exhaled air is shown by arrows going into the exhaled air collector. In this side view, it is shown where the opening on the front, user-facing side of the exhaled air collector has an opening that allows for entry of the exhaled air and in this case placement of a laptop computer. The exhaled air travels to an air suction conduit connecting the exhaled air collector to the air purification chamber where it is cleaned and/or filtered and then the cleaned and/or filtered air leaves the air purification unit. In this embodiment, two fans are used; one fan is used to suction air into the conduit, and a second fan is used to actively send/exhaust cleaned and/or filtered air from the device and back into the environment from where it was collected.

The air suction conduit can be adjustable in its length (shortened and/or lengthened). The exhaled air collector can comprise a fan. The exhaled air purification chamber can comprise a fan. The air suction conduit can comprise a fan. The exhaled air purification chamber can comprise or can be attached to an acoustic silencer or muffler. The exhaled air purification chamber can be partially or fully surrounded by an acoustic silencer or muffler. The exhaled air purification chamber can be partially or fully surrounded by a sound reducing material. Such materials can be, by way of example only, felt, cotton, foam, wood, or corrugated paper. The exhaled air collector can be made of by way of example only, plastic, fabric, and/or metal. The plastic can be that of a clear plastic. The exhaled air collector can be made of a flexible, semi-rigid, or rigid material. The air purification chamber can comprise one or more of, by way of example only, a HEPA Filter, a UV light, a germicidal light, a microbicidal agent, a microbicidal material, or a thermal heating element. The HEPA filter can comprise, by way of example only, HP-13, HP-14, HP-15, HP-16, or HP-17, and so on. In aspects, HEPA filters can remove particles from filtered air down to 0.3 microns having a MERV rating of 16. In an embodiment of the invention comprising multiple filters the air purification unit can clean air particles down to 0.1 microns. In another embodiment of the invention comprising multiple filters and UVC light the air purification unit can clean air down to 0.1 microns.

Figure 13:
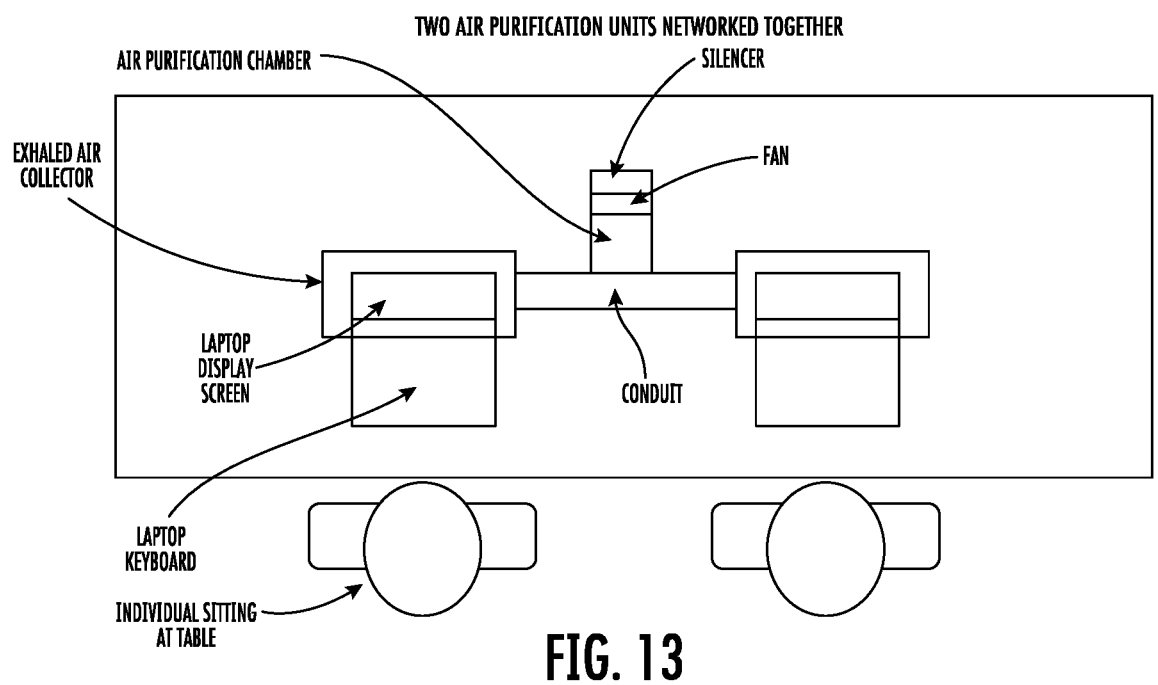
FIG. 13 is a top-looking-down view drawing of a possible embodiment according to the present invention showing an air purification unit.

In embodiments a first exhaled air collector and a second exhaled air collector can send collected exhaled air to a common exhaled air purification chamber that purifies the exhaled air received from both exhaled air collectors. For example, as shown in FIG. 13, two exhaled air collectors are shown connected via conduit to one air purification chamber. Two individuals are shown sitting at a table using laptop computers with display screen and keyboard. In this embodiment, a fan is used to blow/force/exhaust cleaned and/or filtered air from the air purification chamber back into the environment from which the exhaled air was collected. Also, in this embodiment a silencer or muffler is shown that would decrease sound created by the fan or other components of the unit.

In embodiments, an individual sitting or standing in front of an exhaled air collector can adjust the height of the exhaled air collector such that the individual's line of sight when looking straight ahead or at a distance is above the top edge of the exhaled air collector when using the exhaled air collector. An individual sitting or standing in front of an exhaled air collector can adjust, if needed, the height of the exhaled air collector such that the individual's line of sight is above the top edge of the exhaled air collector when using the exhaled air collector. In other embodiments, an individual sitting or standing in front of an exhaled air collector can adjust, if needed, the height of their chair, seat, bench, or that of the height of the table or desk to then ensure that the individual's line of sight is above that of the top edge of the exhaled air collector. In still other embodiments the upper front of the exhaled air collector can have an attached exhaled air guide. This guide can be adjusted up and down vertically so to adjust the angle of the guide to the desk or tabletop. The guide can also be adjusted in length so that an individual sitting in front of the guide can pull the guide closer to their face. The front edge of the guide from a vertical perspective after extending could be adjusted so to not block their line of sight.

Figure 14:
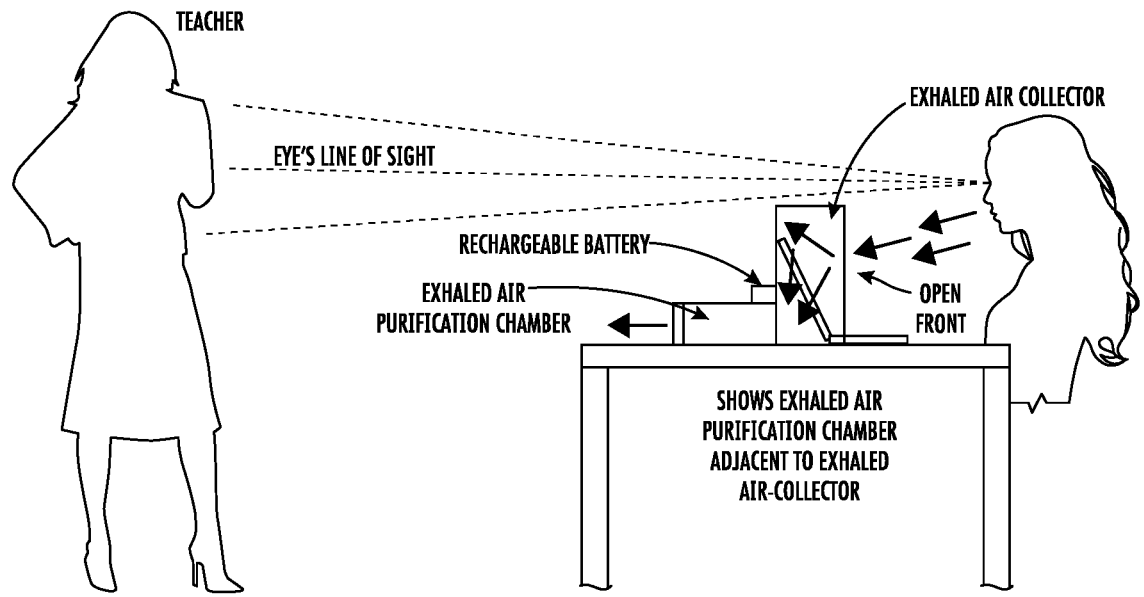
FIG. 14 is a side view drawing of a possible embodiment according to the present invention showing an air purification unit.
Figure 15:
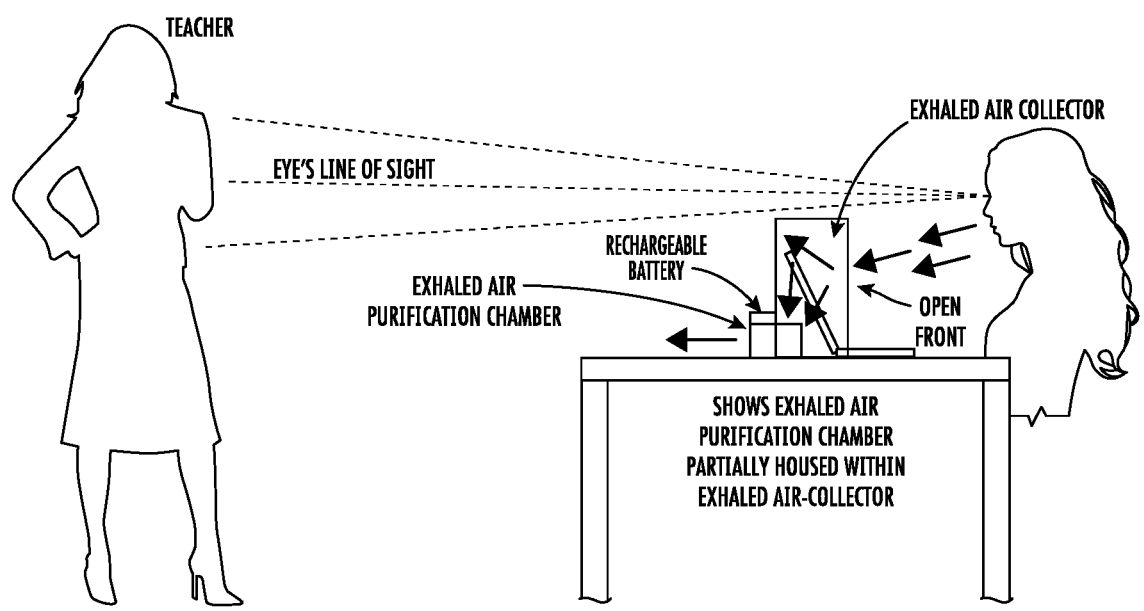
FIG. 15 is a side view drawing of a possible embodiment according to the present invention showing an air purification unit.
Figure 16:
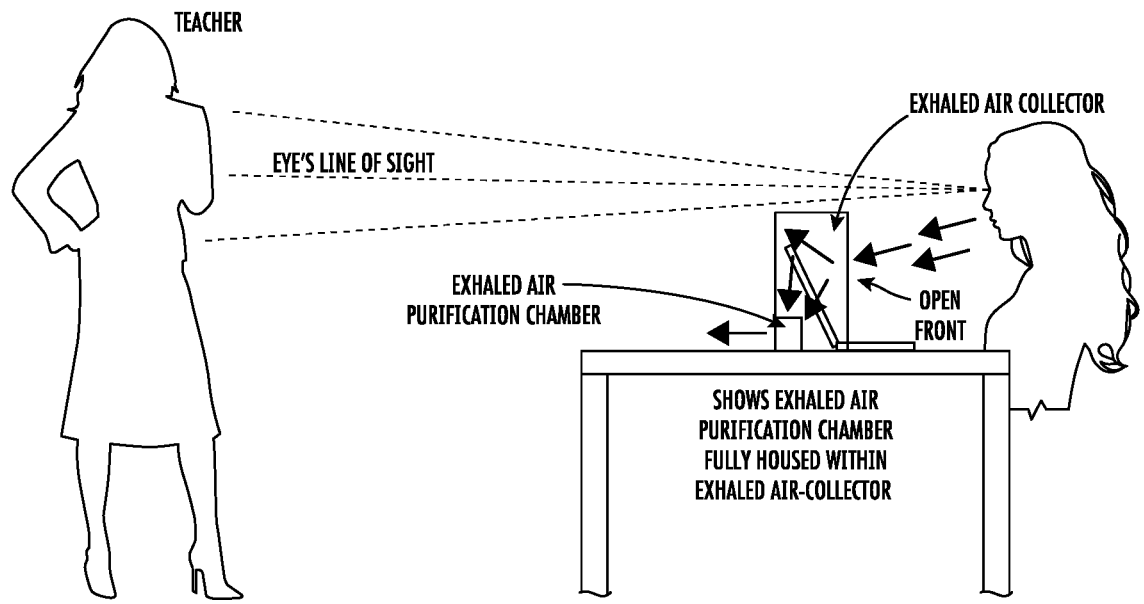
FIG. 16 is a side view drawing of a possible embodiment according to the present invention showing an air purification unit.
Figure 17:
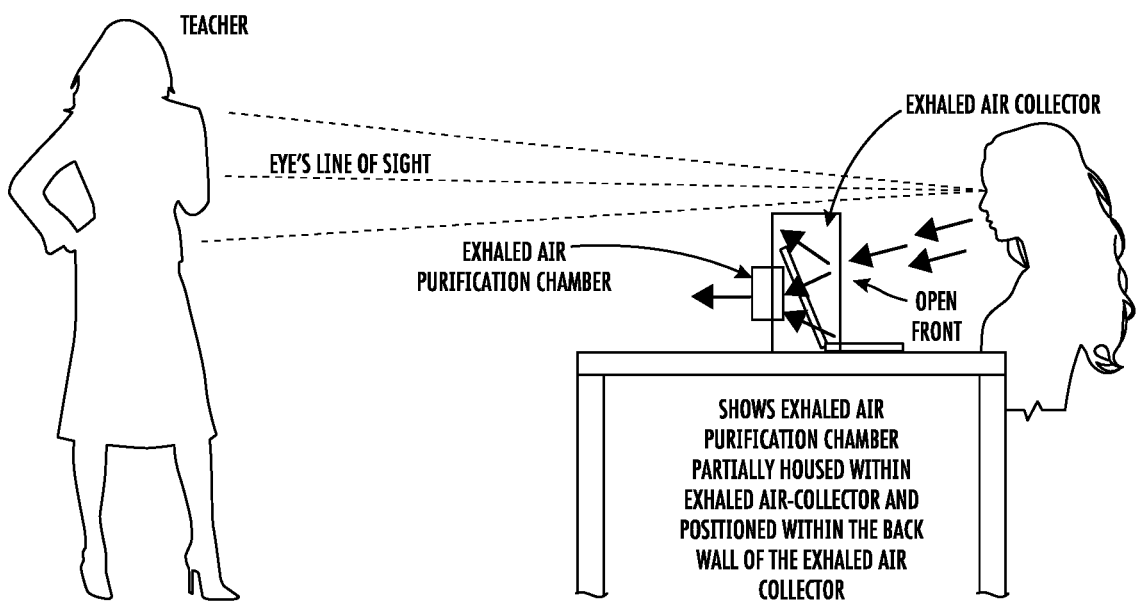
FIG. 17 is a side view drawing of a possible embodiment according to the present invention showing an air purification unit.

For example, in FIG. 14, an exhaled air collector with an open front is shown collecting exhaled air from an individual sitting or standing in front of the air purification unit. In this side view, it is shown where the opening on the front, user-facing side of the exhaled air collector has an opening that allows for entry of the exhaled air and in this case placement of a laptop computer. The exhaled air travels directly to an adjacent air purification chamber where cleaned and/or filtered air are then exhausted from the unit. In this embodiment, a rechargeable battery is used to power the unit. Also, in this Figure, it is shown how a user's line of sight is above the top of the exhaled air collector so, for example, the user can see a teacher, presenter, or performer, by way of example. Similarly in FIG. 15, an exhaled air collector with an open front is shown collecting exhaled air from an individual sitting or standing in front of the air purification unit. In this side view, it is shown where the opening on the front, user-facing side of the exhaled air collector has an opening that allows for entry of the exhaled air and in this case placement of a laptop computer. In this embodiment, the exhaled air purification chamber is located, housed, or contained partially within the exhaled air collector. The exhaled air is cleaned and/or filtered and then exhausted from the unit. In this embodiment, a rechargeable battery is used to power the unit. Also, in this Figure, it is shown how a user's line of sight is above the top of the exhaled air collector so, for example, the user can see a teacher, presenter, or performer, by way of example. Similarly in FIG. 16, an exhaled air collector with an open front is shown collecting exhaled air from an individual sitting or standing in front of the air purification unit. In this side view, it is shown where the opening on the front, user-facing side of the exhaled air collector has an opening that allows for entry of the exhaled air and in this case placement of a laptop computer. In this embodiment, the exhaled air purification chamber is located, housed, or contained completely within the exhaled air collector. (In this embodiment, the air purification chamber is positioned within or near a back wall of the exhaled air collector.) The exhaled air is cleaned and/or filtered and then exhausted from the unit. Also, in this Figure, it is shown how a user's line of sight is above the top of the exhaled air collector so, for example, the user can see a teacher, presenter, or performer, by way of example. Similarly in FIG. 17, an exhaled air collector with an open front is shown collecting exhaled air from an individual sitting or standing in front of the air purification unit. In this side view, it is shown where the opening on the front, user-facing side of the exhaled air collector has an opening that allows for entry of the exhaled air and in this case placement of a laptop computer. In this embodiment, the exhaled air purification chamber is located, housed, or contained partially within the exhaled air collector. The exhaled air is cleaned and/or filtered and then exhausted from the unit. (In this embodiment, the air purification chamber is positioned within or near a back wall of the exhaled air collector.) Also, in this Figure, it is shown how a user's line of sight is above the top of the exhaled air collector so, for example, the user can see a teacher, presenter, or performer, by way of example.

The exhaled air purification chamber can comprise one or more of the following: a filter, a HEPA filter, UVC light, Far UVC light, germicidal light, plasma, heat, or microbicidal materials, such as, by way of example only, copper, silver, zinc, copper ions, silver ions, silver nanoparticles, $TiO_2$ nanoparticles, ZnO nanoparticles, organic compounds, hybrids of organic/inorganic nanoparticles, alcohol, hydrogen peroxide, and/or iodine. As used herein cleaning/purifying can be meant to destroy a particulate and/or pathogen, and/or to filter and separate out airborne particulates and/or pathogens. Clean or purified air can be cleaned or purified by way of one or more of: a filter, a HEPA filter, UVC light, Far UVC light, germicidal light, plasma, heat, or microbicidal materials, such as, by way of example only, copper, silver, zinc, copper ions, silver ions, silver nanoparticles, $TiO_2$ nanoparticles, ZnO nanoparticles, organic compounds, hybrids of organic/inorganic nanoparticles, alcohol, hydrogen peroxide, and/or iodine.

A recessed exhaled air blocking surface can be that of the inside back vertical wall of an exhaled air collector. In certain embodiments a portion or all the recessed exhaled air blocking surface can be that of a video display screen. An exhaled air collector may or may not comprise an exhaled catch basin. An exhaled catch basin can be formed in the bottom of an air collector. An air suction intake can be an opening within the exhaled air catch basin that opens to either an attached exhaled air purification chamber or to an air suction conduit. When an exhaled catch basin is present, usually, but not always, the air suction intake is located within the exhaled air catch basin. The air suction intake can be the full size of the bottom of the exhaled air catch basin or smaller than the size of the bottom of the exhaled air catch basin.

An exhaled air collector can open directly to an air suction conduit. In this case the opening to the air suction conduit would be that of the air suction intake. In other embodiments the exhaled air collector houses part or all the exhaled air purification chamber. In embodiments the exhaled air collector can partially or fully house multiple air purification chambers. When the exhaled air collector houses part of an exhaled air purification chamber, the air intake portion of the exhaled air purification chamber is located partially or completely within the exhaled air collector and the air outtake (exit or exhaust) portion of the exhaled air purification chamber is located partially or completely outside of the exhaled air collector. When the exhaled air collector houses all an exhaled air purification chamber, the air intake portion of the exhaled air purification chamber is located within the exhaled air collector and the air outtake (exit or exhaust) portion of the exhaled air purification chamber exhausts clean air through an aperture in or on the exhaled air collector. In cases, the air outtake (exit or exhaust) can be located within an aperture of a wall of the exhaled air collector and in other cases can be connected to the aperture by way of a conduit.

In embodiments of the invention, an exhaled air collector can have its vertical and/or horizontal dimensions be adjustable. An exhaled air collector can be made of, by way of example only, plexiglass, acrylic, plastic, metal, glass, cloth, fabric, wood, ceramic, or rubber. In certain embodiments the exhaled air collector can be clear, semi-transparent, or transparent. In certain embodiments of the invention an air suction conduit can be adjustable in length. By adjustable in length, it is meant to mean expanded and/or contracted or lengthened and/or shortened. In aspects, the air suction conduit can be bent, shaped, or manipulated. An air suction conduit can be made of, by way of example only, rubber, plastic, foam, metal, or fabric. The air suction conduit can comprise foam/porous walls. In embodiments the air suction conduit can comprise an acoustic reducing or silencing material such as, by way of example only, foam or porous materials. These materials can be treated with or comprise microbicidal agents. In embodiments the air purification chamber can comprise an acoustic reducing or silencing material such as, by way of example only, foam or porous materials. These materials can be treated with or comprise microbicidal agents.

Figure 28:
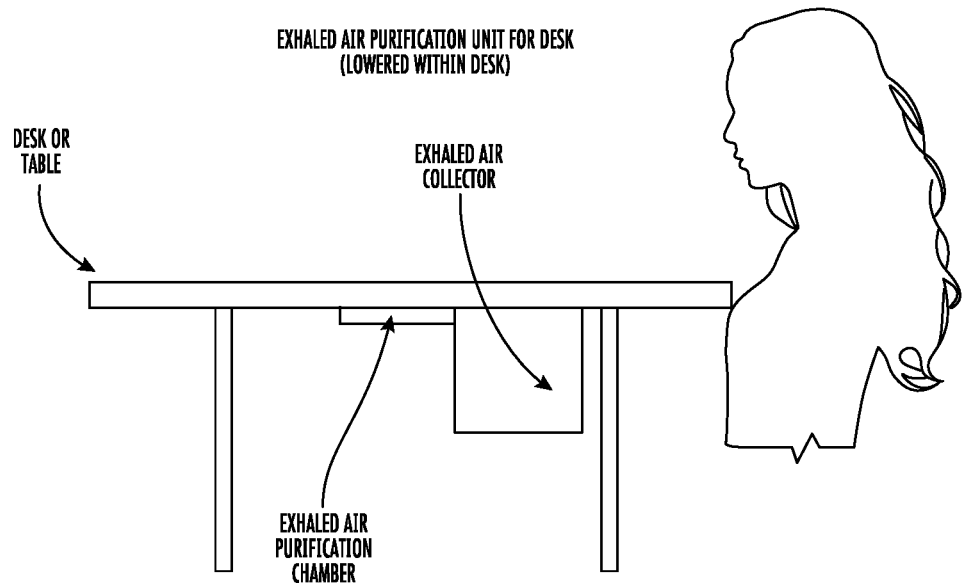
FIG. 28 is a side view drawing of a possible embodiment according to the present invention showing an air purification unit.
Figure 29:
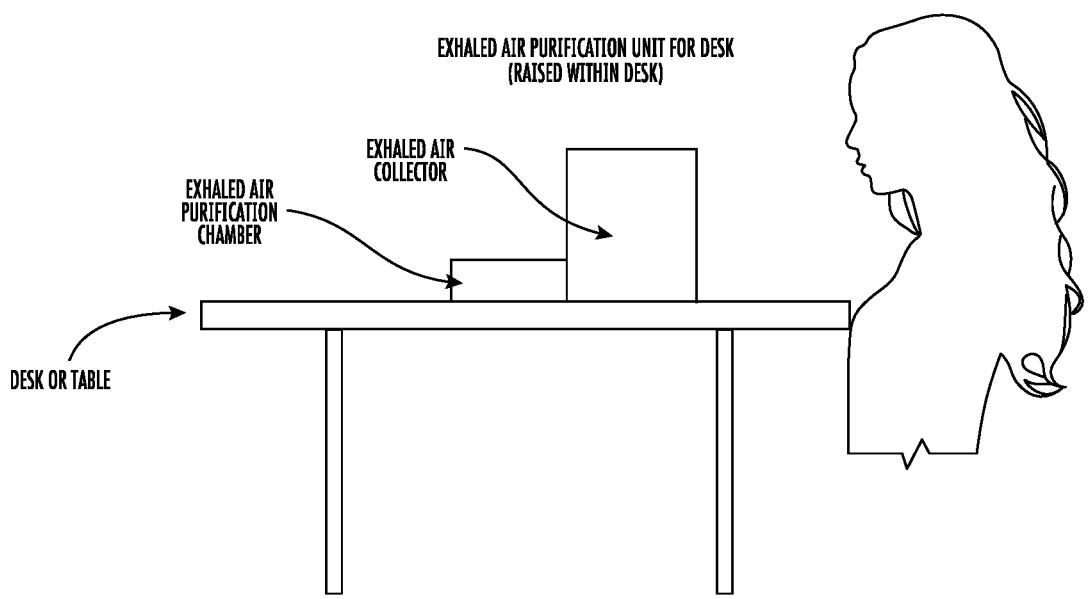
FIG. 29 is a side view drawing of a possible embodiment according to the present invention showing an air purification unit.

In embodiments of the invention, the desk or table can support an exhaled collector and/or an exhaled air purification chamber. In embodiments, the exhaled air collector, the exhaled air purification chamber, or an exhaled air purification unit, can be lowered into or within the top of the desk or table when not in use, and raised when in use, for example. FIG. 28 shows the exhaled air collector and air purification unit located under, lowered under, or stored under (completely or partially) a desk or table. FIG. 29 shows the exhaled air collector and air purification chamber raised within the desk or table.

Figure 11:
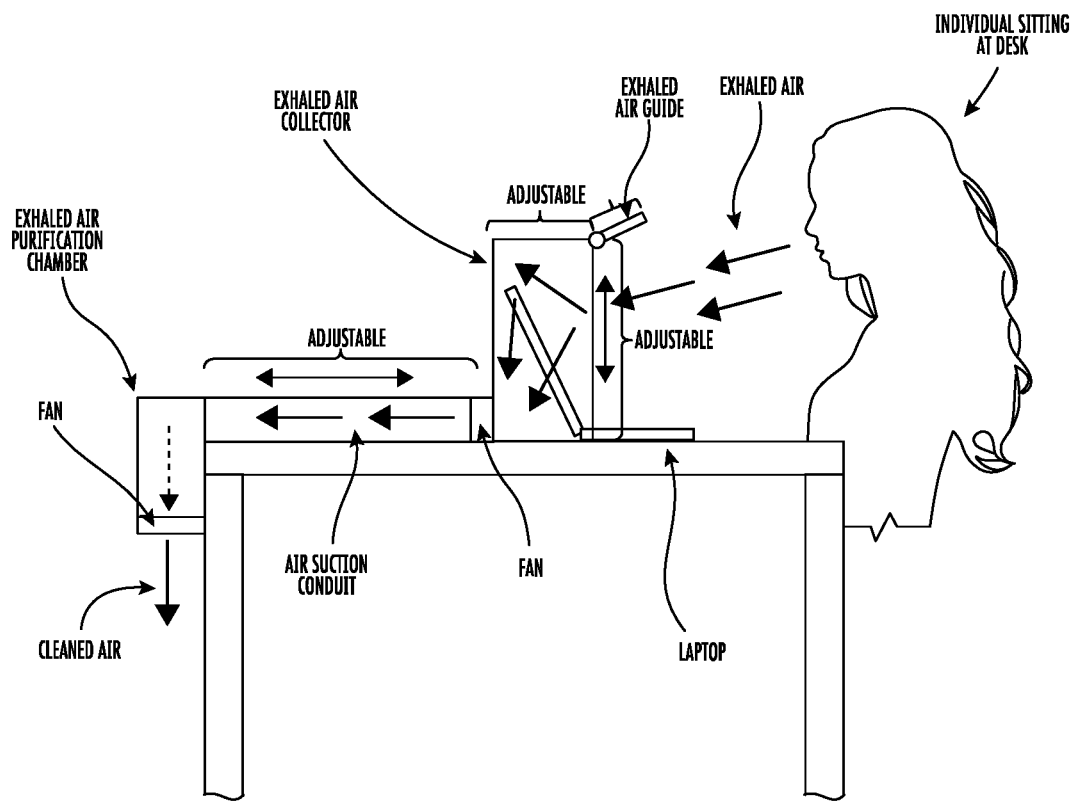
FIG. 11 is a side view drawing of a possible embodiment according to the present invention showing an air purification unit.
Figure 12:
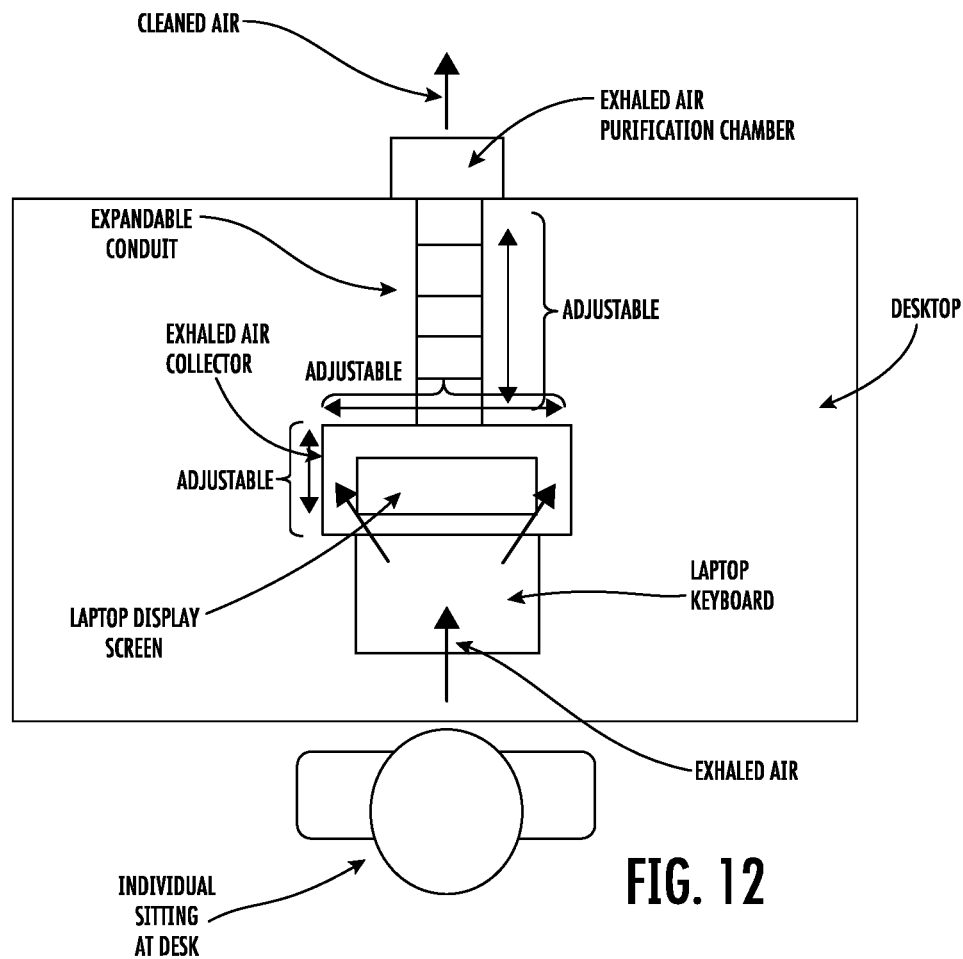
FIG. 12 is a top-looking-down view drawing of a possible embodiment according to the present invention showing an air purification unit.

For example, in FIG. 11, an air purification unit embodiment is shown from the side, wherein the human's exhaled air is shown by arrows going into the exhaled air collector. In this side view, it is shown where the opening on the front, user-facing side of the exhaled air collector has an opening that allows for entry of the exhaled air and in this case placement of a laptop computer. The exhaled air travels to an air suction conduit connecting the exhaled air collector to the air purification chamber where it is cleaned and/or filtered and then the cleaned and/or filtered air leaves the air purification unit. In this embodiment a fan is used to suction air into the conduit, and a fan is used in the exhaled air purification chamber to blow cleaned and/or filtered air back into the environment from the unit. In other words, in this embodiment, a second fan in the air purification chamber actively sends/exhausts/forces/blows cleaned and/or filtered air from the device and back into the environment from where it was collected. Also, in this embodiment it is shown that the air suction conduit is adjustable, for example in length. As shown in FIG. 11, the exhaled air collector is also adjustable; for example, the depth can be altered, the height can be altered, and the width can be altered. Further, the angle of the exhaled air guide can be adjusted. Similarly, in FIG. 12, an air purification unit embodiment is shown from the top looking down to the desktop, wherein the human's exhaled air is shown by arrows going into the exhaled air collector. In this top-down view, it is shown where the opening on the front, user-facing side of the exhaled air collector has an opening that allows for entry of the exhaled air and in this case placement of a laptop computer. The exhaled air travels to an air suction conduit connecting the exhaled air collector to the air purification chamber where it is cleaned and/or filtered and then the cleaned and/or filtered air leaves the air purification unit. Also, in this embodiment it is shown that the air suction conduit is adjustable, for example in length. As shown in FIG. 12, the exhaled air collector is also adjustable; for example, one or more of, the depth can be altered, the height can be altered, and the width can be altered.

Figure 33:
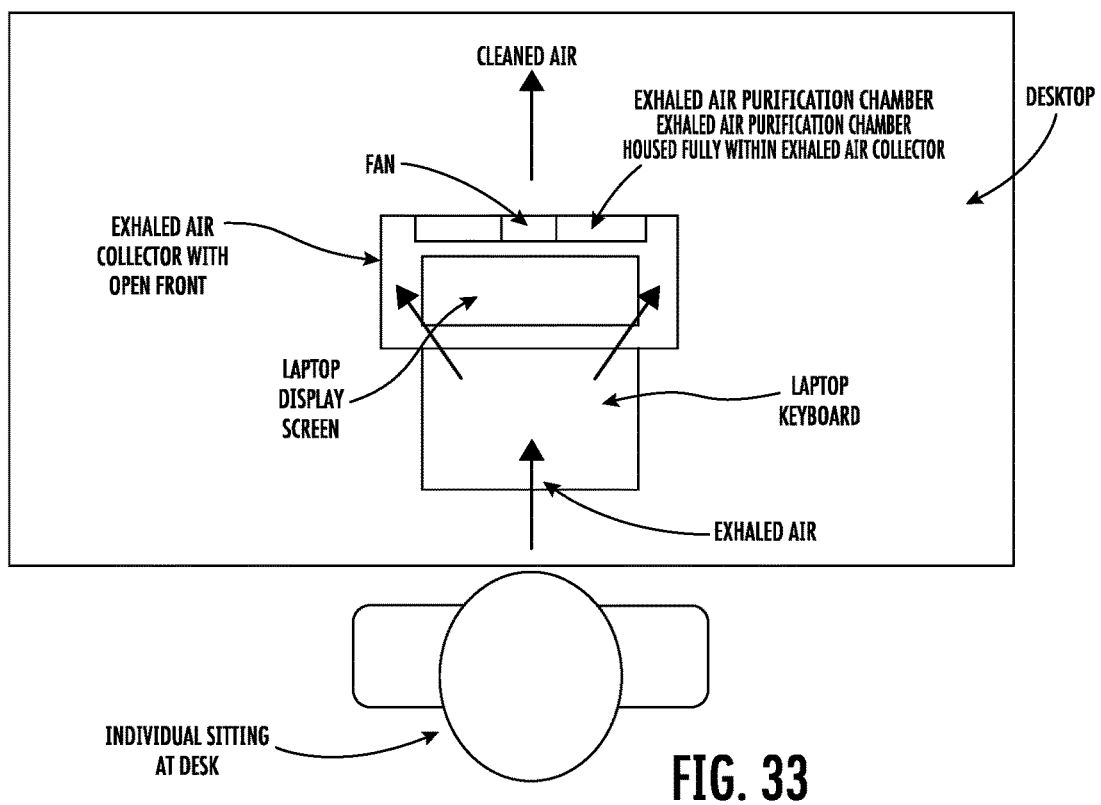
FIG. 33 is a top-looking-down view drawing of a possible embodiment according to the present invention showing an air purification unit.

Similarly, in FIG. 33, an air purification unit embodiment is shown from the top looking down to the desktop or tabletop, wherein the human's exhaled air is shown by arrows going into the exhaled air collector. In this top-down view, it is shown where the opening on the front, user-facing side of the exhaled air collector has an opening that allows for entry of the exhaled air and in this case placement of a laptop computer (e.g., a display screen and/or keyboard). The exhaled air in this embodiment is suctioned into the air purification chamber where it is cleaned and/or filtered and then the cleaned and/or filtered air leaves the air purification unit. In this embodiment the air purification chamber is shown located within the exhaled air collector (e.g., in a cavity of the exhaled air collector).

In embodiments of the present invention, an exhaled air purification unit captures, cleans, optionally filters, and exhausts cleaned and/or filtered exhaled air directly into the venue where the exhaled air purification unit is present. In embodiments of the present invention, an exhaled air purification unit captures, cleans, optionally filters, and moves cleaned and/or filtered exhaled air out of the venue by way of one or more conduits into the outside environment or a different environment. In embodiments of the present invention, an exhaled air purification unit captures, cleans, optionally filters, and moves the cleaned and/or filtered exhaled air by way of one or more conduits into the venue's HVAC system or air handling system.

In embodiments of the present invention, an exhaled air collector and/or exhaled air purification chamber captures, filters, and exhausts cleaned and/or filtered exhaled air directly into the venue where the exhaled air collector and/or exhaled air purification chamber is present. In embodiments of the present invention, an exhaled air collector and/or exhaled air purification chamber captures, filters, and moves cleaned and/or filtered exhaled air out of the venue by way of one or more conduits into the outside environment or a different embodiment. In embodiments of the present invention, an exhaled air collector and/or exhaled air purification chamber captures, filters, and moves the cleaned and/or filtered exhaled air by way of one or more conduits into the venue's HVAC system or air handling system. In embodiments of the invention, an exhaled air purification chamber only filters the air traveling through the exhaled air purification chamber. In embodiments of the invention, an exhaled air purification chamber only purifies the air traveling through the exhaled air purification chamber. In embodiments of the invention, an exhaled air purification chamber only purifies and filters the air traveling through the exhaled air purification chamber. The air that exits the air purification chamber can be up to 99.9% clean air.

In embodiments of the present invention, an exhaled air collector captures exhaled air, which is then moved to a remote exhaled air purification chamber where it is cleaned and/or filtered and then exhausted to an outdoor environment or different environment. Such an exhaled air purification system is that of an open looped system. In embodiments of the present invention disclosed herein, an exhaled air collector captures and moves exhaled air within one or more conduits to a remote exhaled air purification chamber where it is cleaned and/or filtered and then moved into the venue's HVAC or air handling system where it is then recirculated back into the venue from which it was captured. Such an exhaled air purification system is that of a closed looped system. In embodiments of the present invention disclosed herein, an exhaled air collector captures and moves exhaled air within one or more conduits into the venue's HVAC or air handling system where it is cleaned and/or filtered and then recirculated back into the venue from which it was captured. Such an exhaled air purification system is that of a closed looped system. In certain embodiments of the invention, an exhaled air collector connects to an air suction conduit where the non-cleaned and non-filtered exhaled air is moved therethrough and then moved into the venue's air flow that moves the exhaled air out of the venue. Such a venue can be, by way of example only, that of an aircraft. In certain embodiments of the invention, an exhaled air collector connects to an air suction conduit where the non-cleaned and non-filtered exhaled air is moved therethrough and then moved into the venue's air flow that moves the exhaled air into the venues HVAC or air handling system which then cleans and/or filters the exhaled air. Such a venue can be, by way of example only, that of a vehicle.

Further embodiments of the invention can be that of an exhaled air collector that comprises a fan or fans for moving air downward across the recessed exhaled air blocking surface of the exhaled air collector. Embodiments of the invention can be that of desk or table that comprises an exhaled air collector that is one of attached to, resting on top of, embedded in or within, or integral or shaped as a part of the desk or table. Embodiments of the invention can be that of a desk or table that receives an exhaled air purification unit. Embodiments of the invention can be that of a desk or table that is shaped to receive an exhaled air purification unit. Embodiments of the invention can be that of a desk or table that is specially shaped to attach to an exhaled air purification unit. Embodiments of the invention can be that of a desk or table that comprises a video display screen and whereby the video display screen is an exhaled air collector and/or an exhaled air blocking surface that deflects exhaled air into the exhaled air collector and/or an air suction conduit. An embodiment of the invention can be a desk or table that supports an exhaled air collector having an open front and recessed air blocking surface and comprises an aperture within its desktop or tabletop permitting a conduit to pass which connects to an exhaled air purification chamber located partially or fully within the desktop or tabletop or under the desktop or tabletop. An embodiment of the invention can be a desk or table that supports an exhaled air collector having an open front and comprises an aperture within its desktop or tabletop permitting a conduit to pass which connects to an exhaled air purification chamber located partially or fully within the desktop or tabletop or under the desktop or tabletop. Another embodiment of the invention is that of a chair, seat, bench, or sitting apparatus that has a back comprising an aperture and an attached exhaled air collector with an open front and recessed exhaled air blocking surface. Another embodiment of the invention is that of a chair, seat, bench, or sitting apparatus that has a back comprising a video display and an attached exhaled air collector with an open front and recessed exhaled air blocking surface. Another embodiment of the invention is that of a chair, seat, bench, or sitting apparatus that has a back comprising an internal conduit and an attached exhaled air collector with an open front and recessed exhaled air blocking surface.

In another embodiment, the exhaled air purification chamber is located within the exhaled air collector. In aspects, when the exhaled air purification chamber is located within the exhaled air collector, the exhaled air purification chamber connects to a conduit that carries the cleaned and/or filtered exhaled air out of or away from the air collector. In aspects, when the exhaled air purification chamber is located within the exhaled air collector, the exhaled air purification chamber is placed near an aperture within a wall or floor of the exhaled air collector that permits the cleaned and/or filtered exhaled air out of the air collector, and/or forces (e.g., via fan) the cleaned and/or filtered exhaled air out of the air collector. In embodiments there is a fan located on an upper inside surface within the exhaled air collector that moves exhaled air downwards towards the exhaled air purification chamber. In embodiments the exhaled air purification chamber is positioned within the exhaled air collector in one of the following placements: close to, adjacent to, or attached to the lower inside back portion of the exhaled air collector. In embodiments, the exhaled air purification chamber is in the lower back corner of the exhaled air collector. In embodiments a portion of the exhaled air purification chamber is within the back wall of the exhaled air collector. In embodiments the exhaled air purification chamber is attached to the floor of the exhaled air collector. In embodiments the exhaled air purification chamber is attached to the inside back wall of the exhaled air collector. In embodiments the exhaled air purification chamber is not attached to but is sitting next to the inside back wall of the exhaled air collector. In embodiments an exhaled air purification chamber can be positioned near or within a portion of one or more of: a wall, a top, a bottom, and/or a back of the exhaled air collector. In embodiments an exhaled air purification chamber can be located within or under a desktop or tabletop and connected to an exhaled air collector that is resting on the desktop or tabletop. In embodiments an exhaled air purification chamber can be one of: located within a chair, seat, bench, or sitting apparatus, attached to a chair, seat, bench, or sitting apparatus, or distance separated and located behind a chair, seat, bench, or sitting apparatus, while being connected to an exhaled air collector. In still other embodiments a portion of the air purification chamber fits through an aperture in the exhaled air collector where a portion of the exhaled air purification chamber pulls air into the exhaled air purification chamber and a portion of the exhaled air purification chamber moves air out of the exhaled purification chamber into the venue, room, or environment. In this case the portion within the exhaled air collector comprises exhaled air intakes and the portion outside the exhaled air collector comprises air outlets for exhausting cleaned air. In still other embodiments the air purification chamber can fit within the exhaled air collector where a portion of the exhaled air purification chamber pulls air into the exhaled air purification chamber and a portion of the exhaled air purification chamber moves air out of the exhaled purification chamber into the venue, room, or environment.

Figure 9:
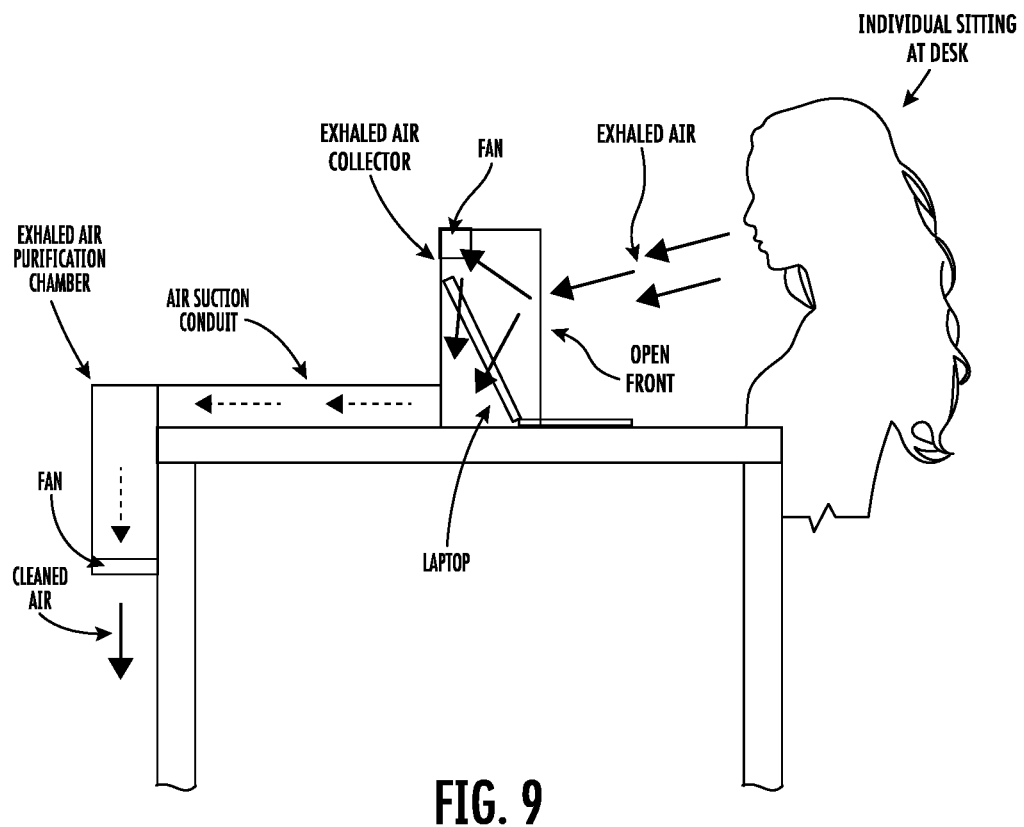
FIG. 9 is a side view drawing of a possible embodiment according to the present invention showing an air purification unit.

For example, in FIG. 9, an air purification unit embodiment is shown from the side, wherein the human's exhaled air is shown by arrows going into the exhaled air collector. In this side view, it is shown where the opening on the front, user-facing side of the exhaled air collector has an opening that allows for entry of the exhaled air and in this case placement of a laptop computer. The exhaled air travels to an air suction conduit connecting the exhaled air collector to the air purification chamber where it is cleaned and/or filtered and then the cleaned and/or filtered air leaves the air purification unit. In this embodiment a fan is located in or on the exhaled air collector to move, force, or blow exhaled air downward and towards the air suction conduit. In this embodiment, a second fan in the air purification chamber actively sends/exhausts/forces/blows cleaned and/or filtered air from the device and back into the environment from where it was collected.

In embodiments the exhaled air purification chamber is attached by a conduit to an exhaust fan that is attached to the back or side wall of the air collector. In embodiments the exhaled air purification chamber comprises two fans; one that moves non-cleaned and/or non-filtered exhaled air into the exhaled air purification chamber, and one that moves cleaned and/or filtered exhaled air out of the exhaled air purification chamber. In embodiments the exhaled air purification chamber comprises two fans; one that moves non-cleaned and/or non-filtered exhaled air downward towards the exhaled air purification chamber, and one that moves cleaned and/or filtered exhaled air out of the exhaled air purification chamber. In embodiments the exhaled air purification chamber comprises a fan that is strong enough to pull air from the exhaled air collector into the exhaled air purification chamber and then out of the exhaled air purification chamber into the room, venue, or environment.

In an embodiment, there can be an aperture within or on the back of the exhaled air collector that permits air that is cleaned by the exhaled air purification chamber to exit. In an embodiment there is an aperture within a wall, back, top, or bottom of the exhaled air collector that permits air that is cleaned by the exhaled air purification chamber to exit. In cases, there is a fan operably connected to the aperture that moves the clean air from the exhaled air purification chamber out of the exhaled air collector. In embodiments a fan within the exhaled air purification chamber moves the air through the aperture in the back of the exhaled air collector. In embodiments the aperture within the exhaled air collector has a fan directly or indirectly attached and the exhaled air purification chamber comprises a fan. In embodiments the aperture in the exhaled air collector can be that of the air suction intake. In other embodiments the air suction intake can be one or more openings on the air intake side of the air purification chamber. This is the case when the air intake side of the air purification chamber is located within the exhaled air collector or within one of a wall, a floor, a top, or a back of the exhaled air collector. In embodiments the exhaled air purification chamber is integrated into the exhaled air collector, such that it is embedded within the back wall of the exhaled air collector. In embodiments the exhaled air purification chamber is integrated into the exhaled air collector, such that it makes up part of the back wall of the exhaled air collector. In these two embodiments air cleaned by the exhaled air purification chamber is moved from the exhaled air purification chamber directly into the room or venue environment where the exhaled air collector is located.

In aspects, the invention herein is an exhaled air purification unit, wherein the exhaled air purification unit comprises an exhaled air collector and an exhaled air purification chamber, wherein the exhaled air collector houses part or all of the exhaled air purification chamber, wherein the exhaled air purification chamber comprises an air suction intake, wherein the exhaled air collector collects non-cleaned, non-filtered exhaled air from a human, wherein the exhaled purification chamber filters, cleans, and/or purifies exhaled air and releases the filtered, cleaned, and/or purified exhaled air outside of the exhaled air purification unit. The air suction intake cam be devoid of a fan. The air suction intake can comprise a fan. The exhaled air collector can collect exhaled air of someone who is sitting or standing in front of or around a desk or a table. The exhaled air collector can collect exhaled air of someone who is sitting or standing behind or around a chair or seat back that is in front of the individual. The exhaled air collector can allow for a part or all of a laptop or desktop computer to be inserted or located therein. The exhaled air collector can be devoid of a computer. The exhaled air collector can be directly adjacent and connected to an exhaled air purification chamber. The exhaled air collector can be connected to an exhaled air purification chamber by way of a conduit. The exhaled air collector can be adjustable in one or more of its dimensions, such as vertical, horizontal, and/or depth. The exhaled air purification chamber can be in the back lower inside portion of the exhaled air collector. The air suction conduit can be adjustable in its length. The air suction conduit can comprise a fan. The exhaled air collector can comprise a fan. The exhaled air purification chamber can comprise a fan. The exhaled air purification chamber can comprise, be attached to, or be surrounded by an acoustic silencer or muffler. The exhaled air collector can be made of clear plastic. The exhaled air collector can be made of a fabric or flexible material. The exhaled air collector can comprise an exhaled air guide on its front top surface. The exhaled air guide can be adjustable in length and/or with the guide's angle relative to a table or desktop. The exhaled air purification chamber can comprise one or more of, by way of example only, a HEPA Filter, a UV light, a germicidal light, and/or a microbiocidal agent or material. One or more exhaled air collectors can send collected exhaled air to an exhaled air purification chamber, and wherein the exhaled purification chamber cleans and/or filters the exhaled air received from the exhaled air collector. An exhaled air collector can be of a height so that the line of sight of an individual sitting or standing in front of the exhaled air collector is above the top edge of the exhaled air collector when using the exhaled air collector.

Figure 10:
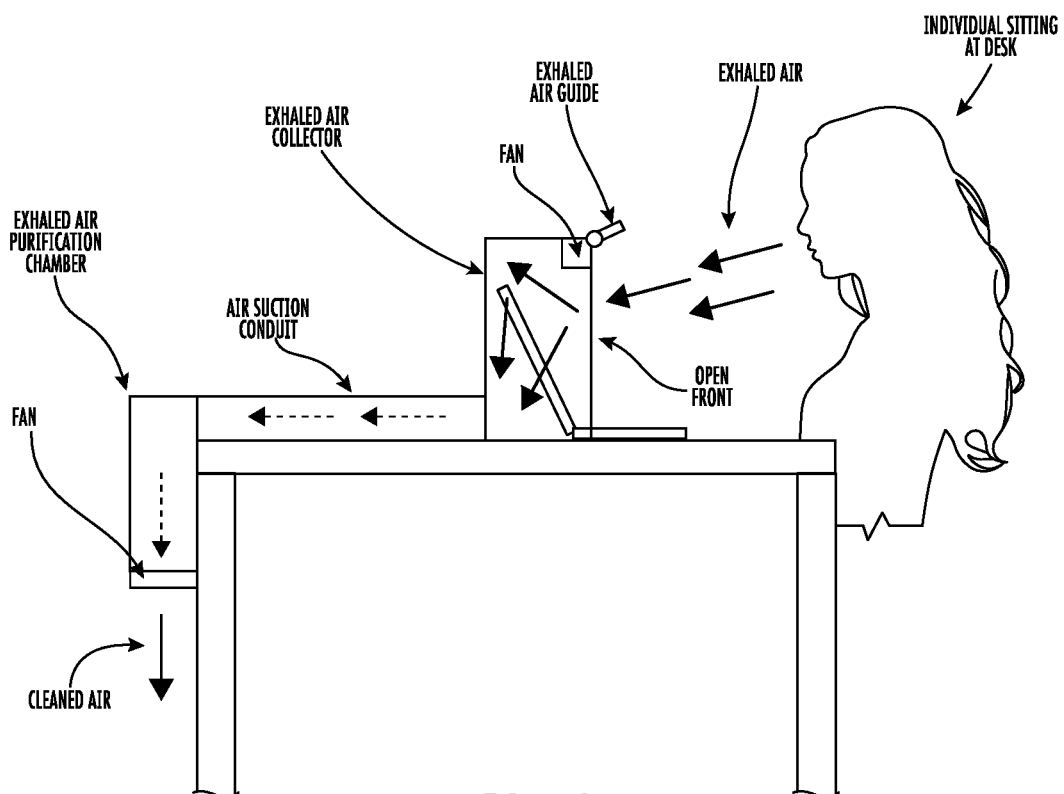
FIG. 10 is a side view drawing of a possible embodiment according to the present invention showing an air purification unit.

For example, in FIG. 10, an air purification unit embodiment is shown from the side, wherein the human's exhaled air is shown by arrows going into the exhaled air collector. In this side view, it is shown where the opening on the front, user-facing side of the exhaled air collector has an opening that allows for entry of the exhaled air and in this case placement of a laptop computer. The exhaled air travels to an air suction conduit connecting the exhaled air collector to the air purification chamber where it is cleaned and/or filtered and then the cleaned and/or filtered air leaves the air purification unit. In this embodiment a fan is located in or on the exhaled air collector to move, force, or blow exhaled air downward and towards the air suction conduit. In this embodiment, a second fan in the air purification chamber actively sends/exhausts/forces/blows cleaned and/or filtered air from the device and back into the environment from where it was collected. Also, in this embodiment an exhaled air guide is shown as described herein.

The exhaled air collector can be capable of capturing 50% or more of exhaled air of an adult or child of average height and weight sitting or standing at the desk or table that supports the exhaled air purification unit (or system) and/or to which the exhaled air purification unit (or system) is located. The exhaled air purification unit can be designed to accommodate a minimum volume of an adult's exhaled air per minute which is, in cases, around 6 liters per minute. The exhaled air purification chamber can have the capability to clean and/or purify a minimum of 0.21188 cubic feet per minute, which equates to the speed and quantity of an average adult's exhaled air. Thus, in aspects, the exhaled air purification unit can clean and/or purify up to 100% of the exhaled air of an individual (adult or child) sitting or standing in front of or around a desk or table that comprises an exhaled air purification unit or system or on which an exhaled air purification unit or system is resting or is located.

In cases of human breathing, following an exhaled breath of air there is a 3 to 5 second pause of the exhaled air stream while the individual who was exhaling air now inhales air. Said another way, after each exhaled air breath in cases there is a 3 to 5 second pause in the exhaled air stream. In aspects of the current invention, this exhaled air stream pause, along with gravity, and in some cases downward air flow, assists in moving the exhaled air into the exhaled air collector and/or the optional air catch basin and through the air suction intake. The exhaled air collection section and the exhaled air purification chamber can have the capability/capacity to collect, clean, optionally filter, and/or purify, in cases, a minimum of 0.21188 cubic feet per minute of air. The exhaled air collection section (the exhaled air collector) can collect, in aspects, a minimum of 0.2 liters of exhaled air within a 6 second interval of time. The exhaled air purification chamber, in cases, can clean a minimum of 0.2 liters of air within a 6 second interval of time. In cases, the exhaled air collector can collect 20 liters or more of exhaled air per minute. In cases, the exhaled air purification chamber can clean 20 liters or more of exhaled air per minute. A fan or fans may be used to move air into and/or through the exhaled air purification unit. Such fan or fans can operate at 5 CFM or greater. A fan or fans used to move air into and/or through an air suction intake can operate at 5 CFM or greater. A fan or fans used to move air through an air suction conduit or conduits to a remote exhaled air purification chamber can operate up to 100 CFM or greater. The exhaled air purification chamber can operate at 3 CADR or greater. In aspects, when the CFM is 5 or greater the air purification can have a decibel level of 60 or less. In aspects, when the CADR of the air purification unit is 20 or more, the air purification unit can have a decibel level of 60 or less. The exhaled air purification chamber can operate at 10 CADR or greater. The exhaled air purification unit can operate at 3 CADR or greater. The exhaled air purification unit can operate at 10 CADR or greater. In certain venues an exhaled air purification chamber can operate at a noise level of 50 DB or less. In certain other venues an exhaled air purification chamber can operate at a noise level of 60 DB or less, and so on. In embodiments an exhaled air purification unit can operate at 3 CADR or greater with a noise level of 50 DB or less. In embodiments an exhaled air purification unit can operate at 20 CADR or greater with a noise level of 50 DB or less. In embodiments the exhaled air purification chamber can operate at 3 CADR or greater with a noise level of 50 DB or less. The noise level can be reduced by way of adding a noise silencer or muffler partially around the exhaled air purification unit. The muffler can comprise one or more apertures to allow for cleaned air to exit.

Given the environment or venue, by way of example only, of a school or workplace, in embodiments an air silencer or air muffler can be connected to or associated with a fan. In embodiments an air silencer or air muffler can be connected to or associated with an exhaled air purification chamber. In embodiments, noise silencing material can be, by way of example only, felt, cotton, foam, wood, or corrugated paper that surrounds a portion of the exhaled air purification chamber and/or a muffler can be placed over a portion.

The exhaled air collector can comprise a recessed exhaled air blocking surface. This exhaled air blocking surface can be that of the inside back surface of the back of the exhaled air collector. In embodiments the recessed exhaled air blocking surface can be comprised partially of an electronic display. In embodiments the recessed exhaled air blocking surface can be comprised of the front surface of an electronic display. In embodiments the exhaled air collector is devoid of a recessed exhaled air blocking surface. In these embodiments that are devoid of a recessed exhaled air blocking surface, the surface of the exhaled air purification chamber that comprises air intakes can fill the back of the exhaled air collector, while the surface of the exhaled air purification chamber that comprises air outlets faces away from the exhaled air collector, by way of example only. The exhaled air collector can optionally comprise an exhaled air catch basin. All or a portion of the air suction intake can be located below the exhaled air blocking surface where the exhaled air is first deflected off the exhaled air blocking surface and moved towards the air suction intake. All or a portion of the air suction intake can be located within a lower portion of the exhaled air blocking surface. An air suction intake can be located within the back, the walls, or the bottom of the exhaled air collector. The air suction intake can be covered with or comprise a grill, screen, grate, filter.

In embodiments the exhaled air purification chamber can be supported by the back wall of the exhaled air collector. In aspects of this embodiment, the air intake of the exhaled air purification chamber can be located within the exhaled air collector and the air outtake or air outlet of the exhaled air purification chamber can be located within the back wall of the exhaled air collector or external to the back wall of the exhaled air collector. In aspects, a portion of the exhaled air purification chamber is located perpendicular to the floor of the exhaled air collector, and that portion of the exhaled air purification chamber that is located perpendicular to the floor and/or is located parallel to the back wall can also become that of a recessed exhaled air blocking surface along with that of the inside surface of the back wall of the exhaled air collector.

In embodiments the exhaled air purification chamber can be supported by a wall of the exhaled air collector. In this embodiment the air intake of the exhaled air purification chamber can be located within the exhaled air collector and the air outtake or air outlet of the exhaled air purification chamber can be located within a wall of the exhaled air collector or external to a wall of the exhaled air collector.

In embodiments the exhaled air collector can be devoid of a recessed exhaled air blocking surface and can open in its back to that of an exhaled air purification chamber that can be of the entire size of the back of the exhaled air collector. In this case the back of the air collector can comprise the front of the exhaled air purification chamber. The exhaled air purification chamber can comprise air intakes on the side that are common with the exhaled air collector which suction or move captured exhaled air into the air purification chamber and air outlets on the side that are common with the venue environment can move one or more of cleaned, filtered, and/or purified air into the venue environment.

In embodiments the exhaled air collector can have a horizontal width of 12 inches or greater, by way of example. In embodiments the exhaled air collector can have a vertical height of 8 inches or greater, by way of example. In embodiments the exhaled air collector can have a depth of 1.5 inches or greater, by way of example. An exhaled air collector for a desk or tabletop can be 12 inches wide or more×8 inches high or more×8 inches deep or more, in aspects. An exhaled air purification unit for a desk or tabletop can be 12 inches wide or more×8 inches high or more×8 inches deep or more, in aspects. An exhaled air collector for a desk or tabletop can be a minimum of 8 inches wide×8 inches high×8 inches deep, in aspects. An exhaled air purification unit for a desk or tabletop can be a minimum of 8 inches wide×8 inches high×8 inches deep, in aspects. The recessed exhaled air blocking surface can have a horizontal dimension for a theater seat that is greater than 6 inches, in aspects. The recessed exhaled air blocking surface can have a horizontal dimension of 10 inches or more, in aspects. The recessed exhaled air blocking surface can be surrounded on two or more sides by walls. In embodiments the exhaled air purification chamber can be inserted within or located within the exhaled air blocking surface. The vertical dimension of the recessed area can be greater than 6 inches, in aspects. The recessed depth can be 0.25 inches or greater, in aspects. The recessed depth can be 1 inch or greater for a theater seat and/or a vehicle seat, in aspects. The recessed depth can be 6 inches or greater for use on a desktop or tabletop, in aspects. The recessed depth can range between 0.25 inches and 24 inches, in aspects. The recessed exhaled air blocking surface can form at its bottom an exhaled air catch basin to which exhaled air flows into prior to being removed by the air suction intake. The air suction intake can be located within or near the bottom of the air catch basin. The optional exhaled air catch basin can be part of the exhaled air collector. The optional exhaled air catch basin can be an extension of the exhaled air collector.

Figure 18:
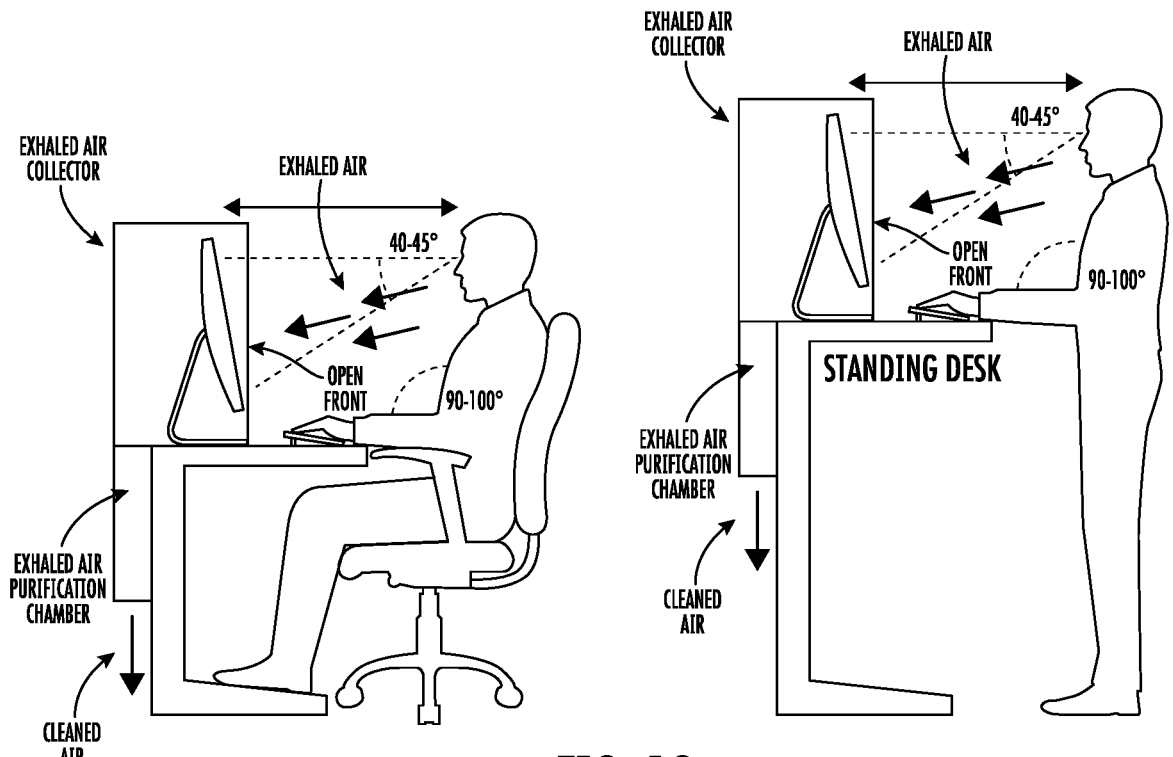
FIG. 18 is a side view drawing of a possible embodiment according to the present invention showing an air purification unit.

FIG. 18 shows two examples of an exhaled air collector with an open front collecting exhaled air from an individual sitting or standing in front of the air purification unit. In this side view, it is shown where the opening on the front, user-facing side of the exhaled air collector has an opening that allows for entry of the exhaled air and in this case placement of a all or a portion of a monitor, display screen, or desktop computer within the opening and area/cavity of the exhaled air collector. The exhaled air is cleaned and/or filtered by the air purification chamber and then exhausted from the unit. In aspects, an individual can be sitting around 15 inches to 36 inches from the front of the exhaled air collector and the exhaled air can be breathed towards the air collector at an angle 10 degrees to 45 degrees, by way of example only.

In embodiments, an exhaled air purification unit can be located within the conduit in the back of a seat or chair that is in front of a different seat or chair. In other embodiments the exhaled air purification unit can be attached to the back of a seat or chair that is in front of a different seat or chair. In other embodiments the exhaled air purification unit can be integrated into the back of a seat or chair that is in front of a different seat or chair. In embodiments the conduit can be a tunnel like opening within the seat or chair and can be surrounded by that of the seat or chair material. In still other embodiments the exhaled air purification unit can be supported by a member that is distance separated but located behind a seat or chair that is in front of a different seat or chair.

An optional exhaled air catch basin can be attached to the exhaled air collector. Depending upon the design of an exhaled air collector, an exhaled air catch basin may or may not be utilized. The exhaled air blocking surface can be located within 45 degrees of being perpendicular to the floor or ground. The exhaled air catch basin can have an air suction intake within the recessed air blocking surface. The exhaled air catch basin can have an air suction intake within the lower wall of the air catch basin. The exhaled air catch basin can have an air suction intake within the bottom of the air catch basin. The exhaled air catch basin can have an air suction intake within a wall of the catch basin. The exhaled air catch basin can be covered with a grate or screen covering. The grate or screen covering can comprise one or more of Copper (Cu+), Copper (Cu++), Silver, Zinc, Gold, TiO2 metal, or plastic comprising a microbicidal agent. The exhaled air catch basin can be uncovered. The exhaled air catch basin can have a lip-like wall on its front side. With the addition of the lip-like wall on its front side, the exhaled air catch basin can have four vertical walls, a bottom, and an open top. The exhaled air collector can comprise a bottom. The exhaled air collector can be devoid of a bottom and utilize the desktop or tabletop as its bottom. The exhaled air collector can have an open front, top, two walls and a back. The exhaled air collector can have an open front, top, floor, two walls and a back. The exhaled air collector can have a front lip wall horizontally across its top front. The exhaled air collector can comprise an aperture in its back. The exhaled air collector can comprise an aperture in one of its side walls.

In embodiments, the front side of the exhaled air collector facing the individual who is standing or sitting in front of the desk or table is open and not covered. When it is covered it can be covered with a grate or screen that comprises a microbicidal material or agent. The grate or screen covering can comprise one or more of Copper (Cu+), Copper (Cu++), Silver, Zinc, Gold, TiO2 metal, or plastic comprising a microbicidal agent.

The exhaled air purification unit can comprise a sensor capable of determining if someone is sitting or standing in front of the air purification unit. The sensor can be, by way of example only, an infra-red sensor, thermal sensor, photosensor, visual sensor, or motion detector. In aspects, the exhaled air purification unit can turn on automatically when someone is sitting or standing in front of the exhaled air purification unit. In aspects, the air purification unit can turn off automatically when someone sitting or standing in front of the air purification unit leaves. The exhaled air purification unit's inner and/or outer surface can be made of a microbicidal material. The exhaled air purification unit's inner and/or outer surface can comprise a microbicidal agent. The exhaled air purification chamber can comprise a surface that is microbicidal. The air purification chamber's inner surface can be reflective. The reflective material can be, by way of example only, a reflective PTFE plastic material, a reflective polytetrafluoroethylene material, or a reflective Teflon plastic material. The exhaled air purification chamber can comprise a fan or fans. The exhaled air purification chamber can comprise an ozone detector and an ozone alter mechanism.

A fan comprising part of the exhaled air purification unit can be attached to an acoustic reducing material. The exhaled air purification unit can comprise an acoustic reducing material. The air suction conduit can comprise an acoustic reducing material. The air suction conduit can be insulated. The exhaled air purification chamber can comprise an acoustic reducing material. An acoustic reducing material can be, by way of example only, felt, cotton, foam, wood, or corrugated paper. The exhaled air purification chamber can be surrounded by an acoustic reducing material. The air purification chamber can be surrounded by a muffler. The muffler can have one or more apertures to allow cleaned air to exit.

The exhaled air purification unit can comprise a fan located at the inside top of the exhaled air collector. The air purification unit can comprise a fan located at the top of the recessed exhaled air blocking surface and/or below the recessed exhaled air blocking surface. The exhaled air purification unit can comprise a fan located at the bottom of the recessed exhaled air blocking surface and/or below the recessed exhaled air blocking surface. The exhaled air purification unit can be devoid of a fan. An exhaled air purification chamber that is adjacent to the exhaled air purification unit can comprise a fan at one or more of a front section, a middle section, or a rear section. The exhaled air collector can comprise a fan attached to its inside top surface. The exhaled air collector can comprise a fan attached to its inside bottom surface. The exhaled air collector can comprise a fan attached to its inside back surface. The inside back surface of the exhaled air collector can be that of the recessed air blocking surface. The exhaled air collector can comprise a fan located at the top of the recessed exhaled air blocking surface or located above the recessed exhaled air blocking surface. The exhaled air collector can comprise a fan located at the bottom of the recessed exhaled air blocking surface or located below the recessed exhaled air blocking surface. The exhaled air collector can comprise a fan located at the back of the exhaled air blocking surface. An exhaled air purification unit can comprise a fan located within an air suction intake. The exhaled air collector can be devoid of a fan. An exhaled air purification chamber that is adjacent to an exhaled air collector can comprise a fan. An exhaled air purification chamber that is adjacent to the exhaled air collector can comprise a fan at the junction of where the exhaled air purification chamber and the exhaled air purification collector share a common opening or aperture. An exhaled air purification chamber that is integrated into the exhaled air purification unit can comprise a fan at its top. An exhaled air purification chamber that is integrated into the air purification unit can comprise a fan at its bottom. An exhaled air purification chamber that is integrated into the air purification unit can comprise a fan at its back. An exhaled air purification chamber that is housed fully or partially within an exhaled air collector can comprise a fan. The exhaled air purification unit can work in conjunction with overhead downward air flow of the venue in which it resides. The exhaled air purification unit can work without downward air flow of the venue in which it resides.

In embodiments the venue's downward airflow from above can be utilized to help move an individual's exhaled air towards and/or into an exhaled air collector. The exhaled air collector can have an open front. The downward air can be that of directional air flow that is from an air jet or fan that is adjustable up to 360 degrees and/or is rotational around the X, Y, and Z axes. The downward air flow can also be that of an air curtain that is located above the exhaled air collector. The exhaled air collector can be one or more of the following: attached to a seat back, formed in a seat back, integrated onto a seat back, distanced separated from a seat back but positioned behind the seat back, supported by a tabletop, supported by a desktop, or supported by a ledge.

In embodiments wherein the exhaled air purification system comprises a plurality of exhaled air collectors that connect to one or more remote air purification chambers, the one or more remote exhaled air purification chambers can connect to the venue's HVAC or air handling system. In still other embodiments, two or more exhaled air collectors can connect to a remote exhaled air purification chamber or more than one air purification chamber without connecting to the venue's HVAC or air handling system.

An exhaled air purification unit can be supported by, attached to, or integrated into, a desk or table. The exhaled air purification chamber can utilize UV light. UV light used in an exhaled air purification chamber can be that within the range of 100 to 400 nanometers. In embodiments the UV light is that of a UVC light having a wavelength within the range of 100 to 280 nanometers. The UVC light can have a wavelength within the range of 222-265 nanometers. The UVC light can have a wavelength of 255+/−10 nanometers. The UV light can also include far UVC light having a wavelength of or around 222 nanometers+/−3 nanometers. Such an exhaled air purification chamber can be part of an exhaled air purification unit or can be part of an exhaled air purification system.

Figure 19:
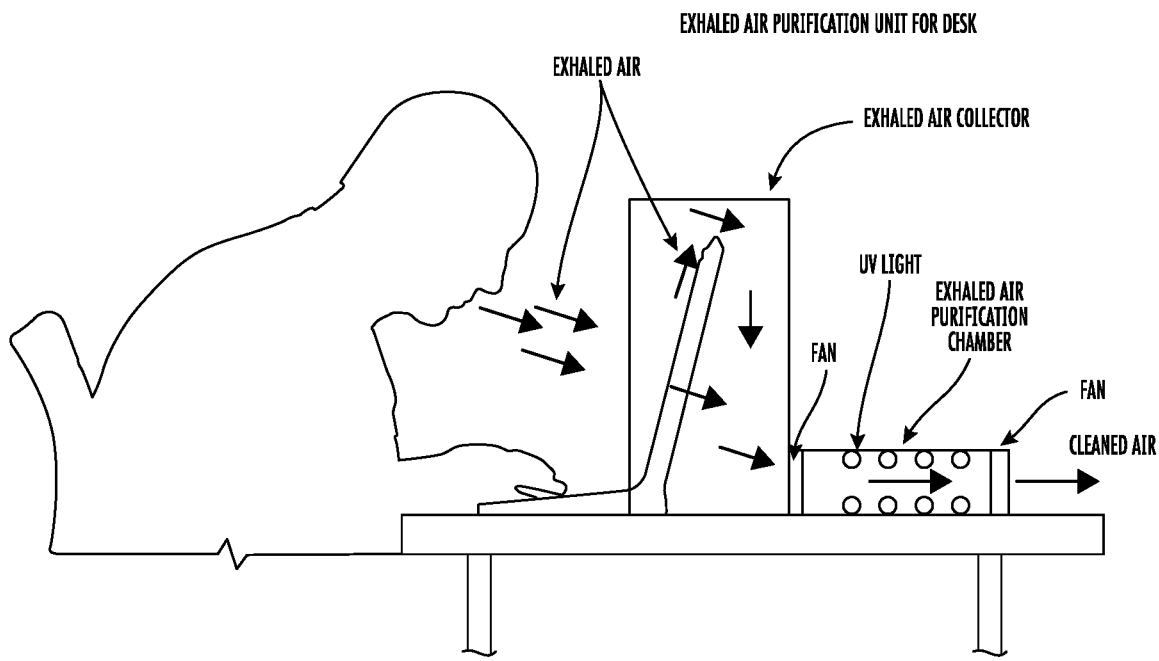
FIG. 19 is a side view drawing of a possible embodiment according to the present invention showing an air purification unit.
Figure 20:
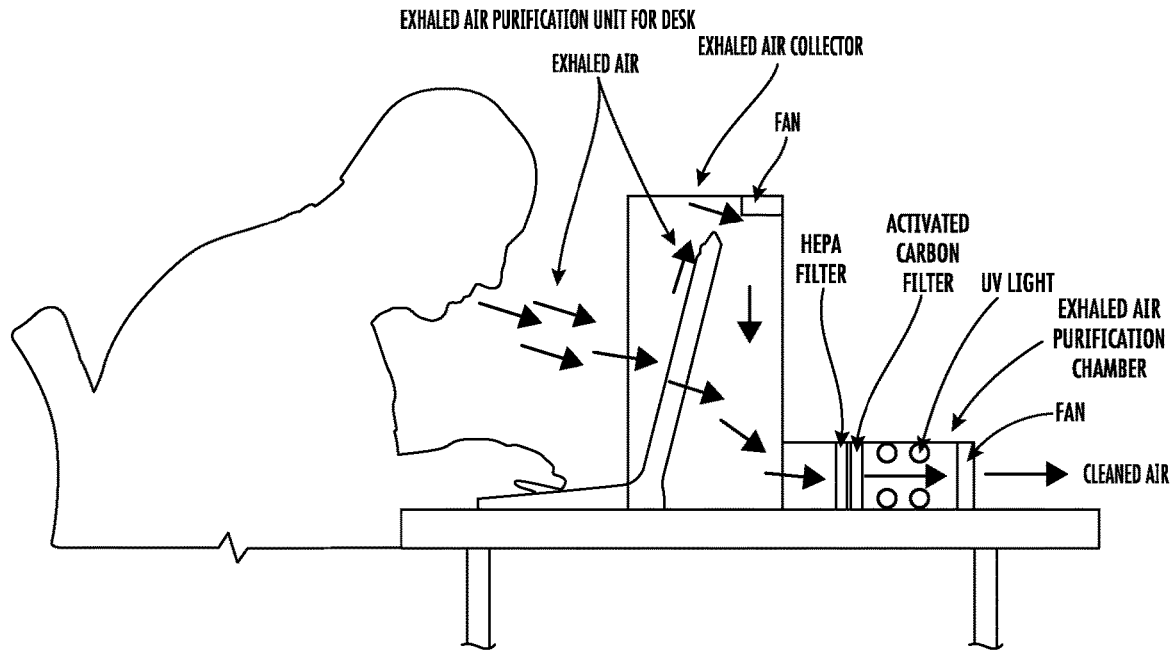
FIG. 20 is a side view drawing of a possible embodiment according to the present invention showing an air purification unit.
Figure 21:
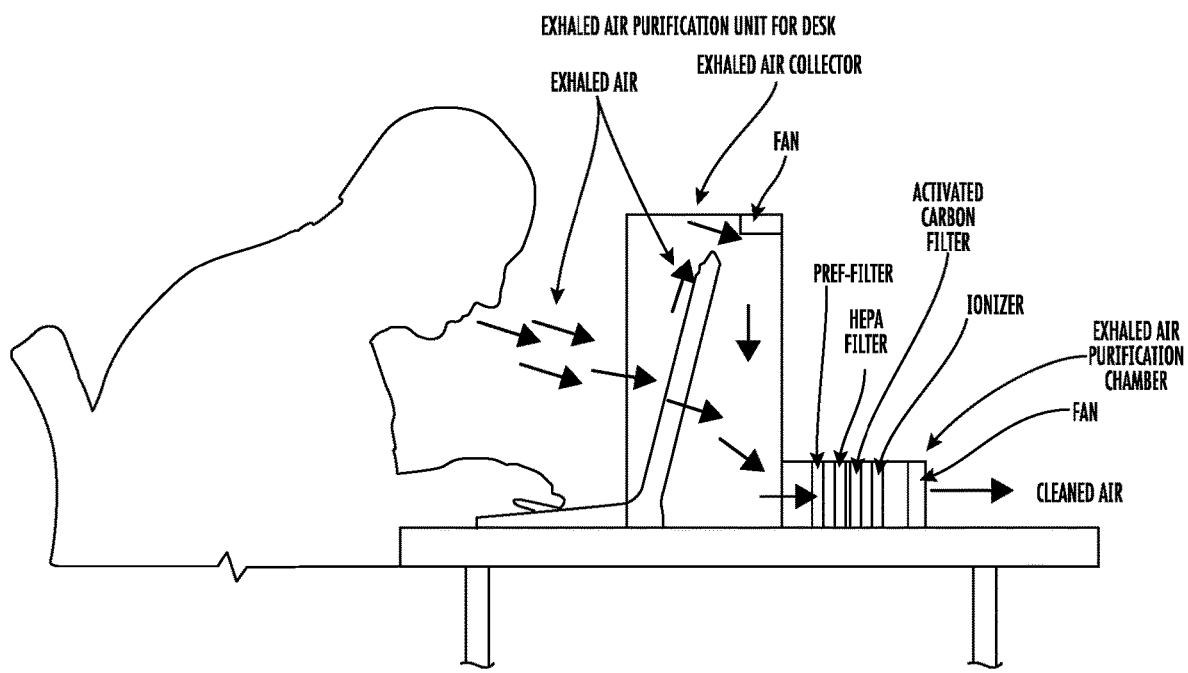
FIG. 21 is a side view drawing of a possible embodiment according to the present invention showing an air purification unit.
Figure 22:
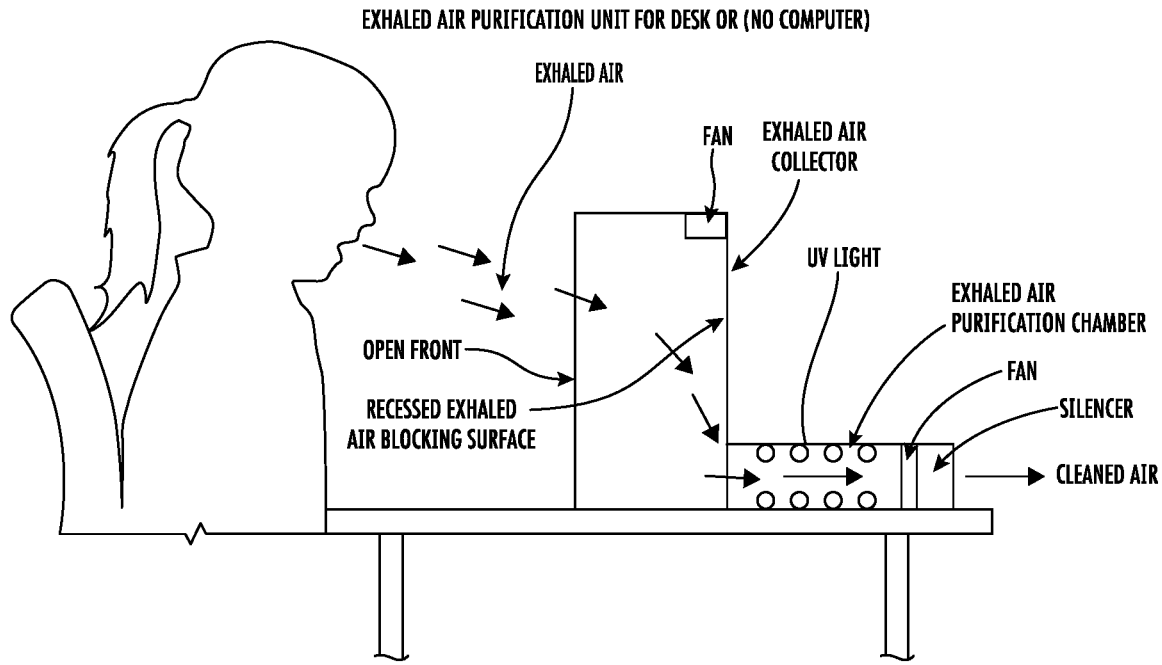
FIG. 22 is a side view drawing of a possible embodiment according to the present invention showing an air purification unit.
Figure 23:
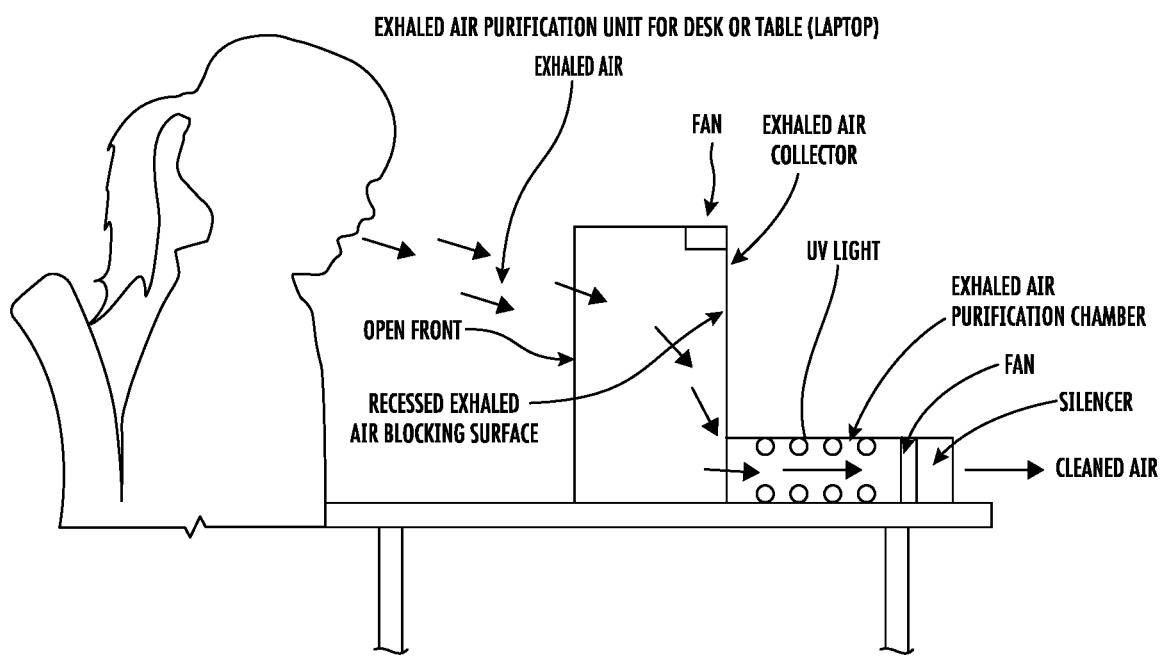
FIG. 23 is a side view drawing of a possible embodiment according to the present invention showing an air purification unit.
Figure 24:
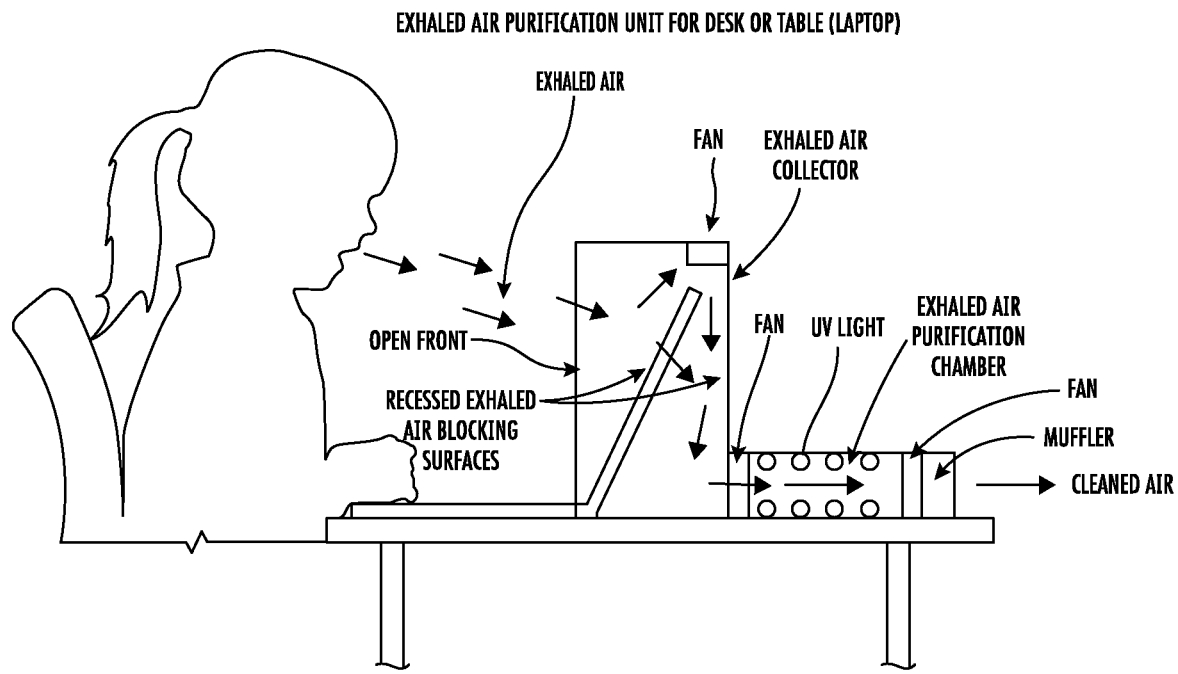
FIG. 24 is a side view drawing of a possible embodiment according to the present invention showing an air purification unit.
Figure 25:
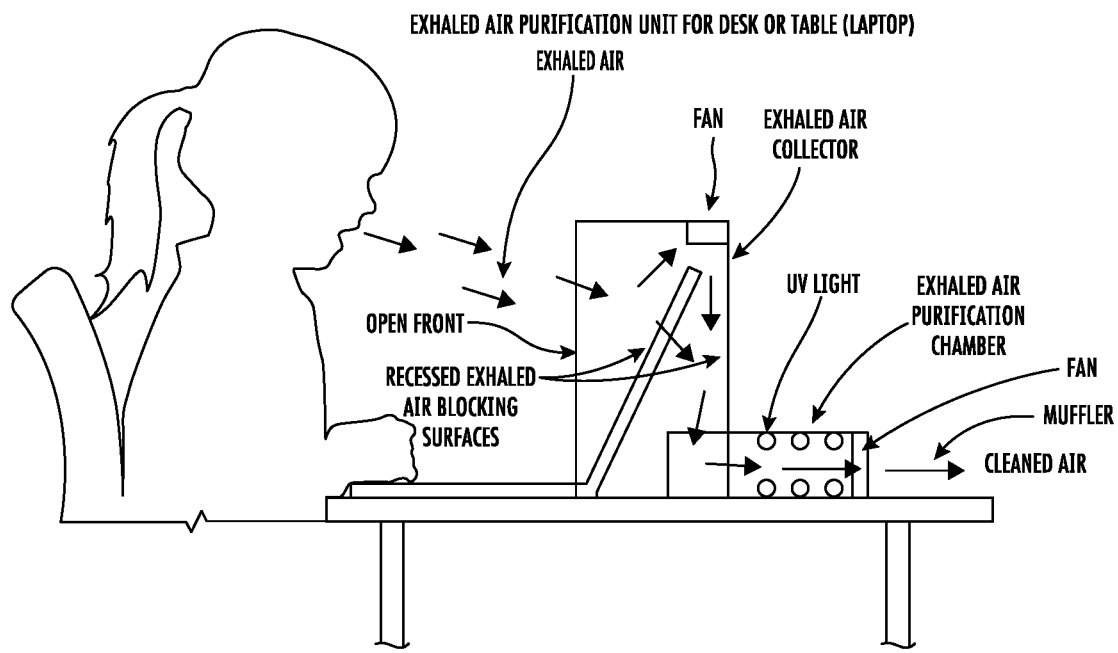
FIG. 25 is a side view drawing of a possible embodiment according to the present invention showing an air purification unit.
Figure 31:
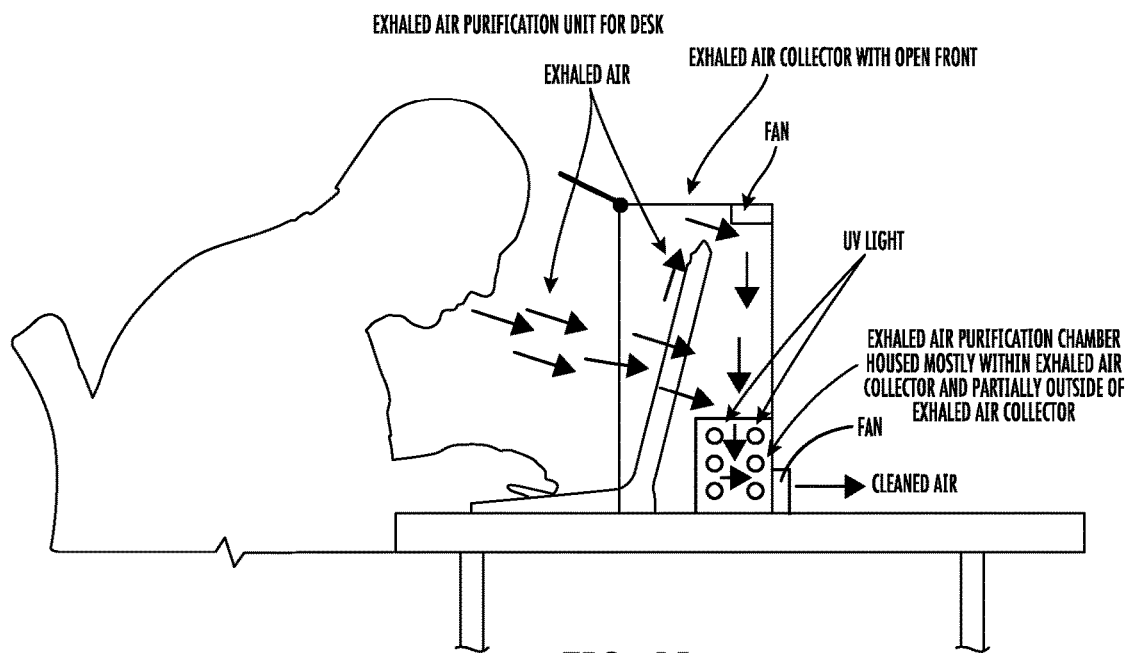
FIG. 31 is a side view drawing of a possible embodiment according to the present invention showing an air purification unit.
Figure 32:
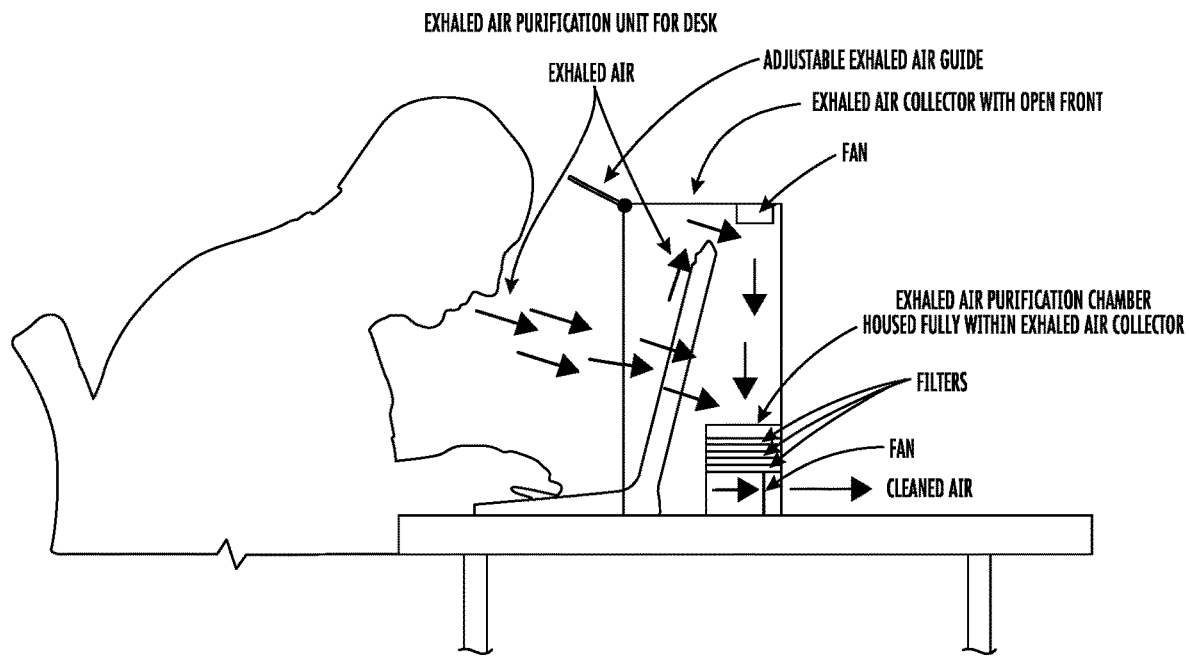
FIG. 32 is a side view drawing of a possible embodiment according to the present invention showing an air purification unit.

For example, in FIG. 19, an air purification unit embodiment is shown from the side, wherein the human's exhaled air is shown by arrows going into the exhaled air collector. In this side view, it is shown where the opening on the front, user-facing side of the exhaled air collector has an opening that allows for entry of the exhaled air and in this case placement of a laptop computer. In this embodiment, the exhaled air travels to an adjacent air purification chamber and it enters by way of fan suction. In this example the exhaled air is sterilized/purified/cleaned by way of a germicidal UV light, as described herein, and the sterilized/purified/cleaned air leaves or is exhausted from the air purification unit. In this embodiment, a second fan in the air purification chamber actively sends/exhausts/forces/blows the sterilized/purified/cleaned air from the device and back into the environment from where it was collected. Similarly in FIG. 20, an air purification unit embodiment is shown from the side, wherein the human's exhaled air is shown by arrows going into the exhaled air collector. In this side view, it is shown where the opening on the front, user-facing side of the exhaled air collector has an opening that allows for entry of the exhaled air and in this case placement of a laptop computer. In this embodiment, the exhaled air travels to an adjacent air purification chamber. In this example the exhaled air is filtered in the air purification chamber by a filter (e.g., prefilter, HEPA filter) and optionally a carbon activated filter. In this embodiment the air is also sterilized/purified/cleaned by way of a germicidal UV light, as described herein, and the filtered and sterilized/purified/cleaned air leaves or is exhausted from the air purification unit. In this embodiment, a fan in the air purification chamber actively sends/exhausts/forces/blows the filtered and sterilized/purified/cleaned air from the device and back into the environment from where it was collected. Also, in this embodiment the exhaled air collector comprises a fan that provides downward air flow to direct exhaled air towards the bottom of the air collector so that it may enter into the air purification chamber. Similarly, FIG. 21 shows an air purification unit embodiment is shown from the side, wherein the human's exhaled air is shown by arrows going into the exhaled air collector. In this side view, it is shown where the opening on the front, user-facing side of the exhaled air collector has an opening that allows for entry of the exhaled air and in this case placement of a laptop computer. In this embodiment, the exhaled air travels to an adjacent air purification chamber. In this example the exhaled air is filtered in the air purification chamber by a pre-filter, a filter (e.g., HEPA filter), and optionally a carbon activated filter. In this embodiment the air is also sterilized/purified/cleaned by way of a germicidal UV light, as described herein. Also, in this embodiment the air is treated by an ionizer. The filtered, sterilized/purified/cleaned, and ionized treated air leaves or is exhausted from the air purification unit. In this embodiment, a fan in the air purification chamber actively sends/exhausts/forces/blows the filtered and sterilized/purified/cleaned air from the device and back into the environment from where it was collected. Also, in this embodiment the exhaled air collector comprises a fan that provides downward air flow to direct exhaled air towards the bottom of the air collector so that it may enter the air purification chamber. In FIG. 22, an air purification unit embodiment is shown from the side, wherein the human's exhaled air is shown by arrows going into the exhaled air collector. In this side view, it is shown where the opening on the front, user-facing side of the exhaled air collector has an opening that allows for entry of the exhaled air (in this case, there is no computer). In this embodiment, the exhaled air travels to an adjacent air purification chamber and the air is blown downwards towards the air purification chamber by a fan. In this example the exhaled air is sterilized/purified/cleaned by way of a germicidal UV light, as described herein, and the sterilized/purified/cleaned air leaves or is exhausted from the air purification unit. In this embodiment, a fan in the air purification chamber actively sends/exhausts/forces/blows the sterilized/purified/cleaned air from the device and back into the environment from where it was collected. In FIG. 23, an air purification unit embodiment is shown from the side, wherein the human's exhaled air is shown by arrows going into the exhaled air collector. In this side view, it is shown where the opening on the front, user-facing side of the exhaled air collector has an opening that allows for entry of the exhaled air and in this case a laptop computer can be partially or fully fit within the exhaled air collector while in use. In this embodiment, the exhaled air travels to an adjacent air purification chamber and the air is blown downwards towards the air purification chamber by a fan. In this example the exhaled air is sterilized/purified/cleaned by way of a germicidal UV light, as described herein, and the sterilized/purified/cleaned air leaves or is exhausted from the air purification unit. In this embodiment, a fan in the air purification chamber actively sends/exhausts/forces/blows the sterilized/purified/cleaned air from the device and back into the environment from where it was collected. In FIG. 24, an air purification unit embodiment is shown from the side, wherein the human's exhaled air is shown by arrows going into the exhaled air collector. In this side view, it is shown where the opening on the front, user-facing side of the exhaled air collector has an opening that allows for entry of the exhaled air and in this case a laptop computer can be partially or fully fit within the exhaled air collector while in use. In this embodiment, the exhaled air travels to an adjacent air purification chamber and the air is blown downwards to the air purification chamber by a fan in, on, or near the exhaled air collector and then suctioned into the air purification unit by another fan in, on, or near the air purification chamber. (FIG. 25 is similar to FIG. 24 but without an air suction fan between the exhaled air collector and air purification chamber.) In this example the exhaled air is sterilized/purified/cleaned by way of a germicidal UV light, as described herein, and the sterilized/purified/cleaned air leaves or is exhausted from the air purification unit. In this embodiment, another fan in the air purification chamber actively sends/exhausts/forces/blows the sterilized/purified/cleaned air from the device and back into the environment from where it was collected. Also, in this embodiment a sound/acoustic silencer or muffler is shown to decrease noise created by the unit which may be distracting to the user or others in the area. FIG. 31 shows an air purification unit embodiment from the side, wherein the human's exhaled air is shown by arrows going into the exhaled air collector. In this side view, it is shown where the opening on the front, user-facing side of the exhaled air collector has an opening that allows for entry of the exhaled air and in this case placement of a laptop computer. In this embodiment, the exhaled air travels to an air purification chamber located within the exhaled air collector (e.g., a cavity within the exhaled air collector). In this example the exhaled air is sterilized/purified/cleaned by way of a germicidal UV light, as described herein, and the sterilized/purified/cleaned air leaves or is exhausted from the air purification unit. In this embodiment, a fan in the air purification chamber actively sends/exhausts/forces/blows the sterilized/purified/cleaned air from the device and back into the environment from where it was collected. Further, this embodiment shows the exhaled air collector comprising a fan blowing air downwards to the bottom of the exhaled air collector and into the air purification chamber. Similarly, FIG. 32 shows an air purification unit embodiment from the side, wherein the human's exhaled air is shown by arrows going into the exhaled air collector. In this side view, it is shown where the opening on the front, user-facing side of the exhaled air collector has an opening that allows for entry of the exhaled air and in this case placement of a laptop computer. In this embodiment, the exhaled air travels to an air purification chamber located within the exhaled air collector (e.g., a cavity within the exhaled air collector). In this example the exhaled air is filtered by one or more filters and sterilized/purified/cleaned by way of a germicidal UV light, as described herein, and the filtered and sterilized/purified/cleaned air leaves or is exhausted from the air purification unit. In this embodiment, a fan in the air purification chamber actively sends/exhausts/forces/blows the sterilized/purified/cleaned air from the device and back into the environment from where it was collected. Further, this embodiment shows the exhaled air collector comprising a fan blowing air downwards to the bottom of the exhaled air collector and into the air purification chamber. An adjustable exhaled air guide is also shown, as described herein.

The exhaled air purification unit, exhaled air collector, recessed air blocking surface if present, optional exhaled air catch basin, and/or air suction conduit, can comprise a microbicidal material, such as, by way of example only, copper, silver, zinc, copper ions, silver ions, silver nanoparticles, TiO2 nanoparticles, ZnO nanoparticles, organic compounds, and/or hybrids of organic/inorganic nanoparticles. The exhaled air collector can be comprised of a microbicidal material, such as, by way of example only, copper, silver, zinc, copper ions, silver ions, silver nanoparticles, TiO2 nanoparticles, ZnO nanoparticles, organic compounds, and/or hybrids of organic/inorganic nanoparticles. The exhaled air purification unit can be covered with and/or comprise a microbicidal material, such as, by way of example only, copper, silver, zinc, copper ions, silver ions, silver nanoparticles, TiO2 nanoparticles, ZnO nanoparticles, organic compounds, and/or hybrids of organic/inorganic nanoparticles. The exhaled air blocking surface and/or the air catch basin can comprise a microbiocidal material, such as, by way of example only, copper, silver, zinc, copper ions, silver ions, silver nanoparticles, TiO2 nanoparticles, ZnO nanoparticles, organic compounds, and/or hybrids of organic/inorganic nanoparticles. The air suction intake can comprise a microbicidal material, such as, by way of example only, copper, silver, zinc, copper ions, silver ions, silver nanoparticles, TiO2 nanoparticles, ZnO nanoparticles, organic compounds, and/or hybrids of organic/inorganic nanoparticles. The exhaled air purification chamber can comprise of a microbicidal material, such as, by way of example only, copper, silver, zinc, copper ions, silver ions, silver nanoparticles, TiO2 nanoparticles, ZnO nanoparticles, organic compounds, and/or hybrids of organic/inorganic nanoparticles. The air suction conduit can comprise a microbicidal material, such as, by way of example only, copper, silver, zinc, copper ions, silver ions, silver nanoparticles, TiO2 nanoparticles, ZnO nanoparticles, organic compounds, and/or hybrids of organic/inorganic nanoparticles. The air purification chamber can be comprised of a microbicidal material, such as, by way of example only, copper, silver, zinc, copper ions, silver ions, silver nanoparticles, TiO2 nanoparticles, ZnO nanoparticles, organic compounds, and/or hybrids of organic/inorganic nanoparticles. The interior of the exhaled air purification unit or an exhaled air purification chamber can comprise an electrostatic surface, such to attract pathogens and/or particulates to its surface.

The exhaled air purification chamber can comprise one or more of the following: a filter, a HEPA filter, UVC light, Far UVC light, germicidal light, plasma, heat, or microbicidal materials, such as, by way of example only, copper, silver, zinc, copper ions, silver ions, silver nanoparticles, TiO2 nanoparticles, ZnO nanoparticles, organic compounds, hybrids of organic/inorganic nanoparticles, alcohol, hydrogen peroxide, and/or iodine. The air suction intake can be comprised of a microbicidal material, such as, by way of example only, copper, silver, zinc, copper ions, silver ions, silver nanoparticles, TiO2 nanoparticles, ZnO nanoparticles, organic compounds, and/or hybrids of organic/inorganic nanoparticles. The air suction intake can have a cover and the cover can be comprised of a microbicidal material, such as, by way of example only, copper, silver, zinc, copper ions, silver ions, silver nanoparticles, TiO2 nanoparticles, ZnO nanoparticles, organic compounds, and/or hybrids of organic/inorganic nanoparticles.

In aspects, UV and/or germicidal bulbs used within the exhaled air purification chamber can provide appropriate or sufficient radiation to inactivate or destroy pathogens or a targeted pathogen. The level of radiation required is, in aspects, dependent upon the time in which the pathogen is exposed while moving through the exhaled air purification chamber. The exhaled air purification chamber and/or exhaled air purification unit can comprise a UV sensor or sensors capable of measuring a level of UV radiation. The UV sensor or sensors can monitor the level of UV radiation within the exhaled air purification chamber and provide an alert or information via, by way of example only, a light, flashing light, alarm, noise, visual cue, or sending an electronic message should the level of UV radiation of a UV bulb fall below that of a preset threshold, by way of example only, below 50% of the manufacturer's specification of the UV radiation level.

In aspects, each exhaled air purification unit can utilize sensor-based self-diagnostics, as well as communicate either wired or wirelessly to a remote computer, such as a laptop, desktop, cell phone, iPad, etc. that can identify if/when certain parts, such as, by way of example only, a filter, fan, light, battery, or sensor, need to be replaced, or if ozone is found above a preset threshold. In embodiments, the exhaled air purification unit can be removable (and replaceable) from a chair or seat to which it is attached or integrated. In embodiments, the exhaled air purification unit can also be removable and attachable (and replaceable). In embodiments, the exhaled air purification unit can be releasably attachable to a desk or table, such that it can be attached to a desk or table and can be removed from the desk or table. The video display screen that can be attached to or integrated within the exhaled air purification unit can be associated with an audio-video system that is connectable to the internet. Such a video display system can stream video and audio or can play stored and recorded video and audio. The video display screen can be in front of the exhaled air blocking surface. The front of the video display screen can be part, or all, of the exhaled air blocking surface. The video display screen can be located above an exhaled air catch basin. The video display screen can be part of an exhaled air purification unit. The video-audio system can be part of the exhaled air purification unit. The video-audio system can be supported by the exhaled air purification unit. In embodiments the video display screen can be part or all the recessed exhaled air blocking surface of the exhaled air collector.

In aspects, an exhaled air purification unit can comprise a sensor that can sense the presence or absence of an individual that is within 3 feet of the front of the exhaled air purification unit, by way of example. In aspects, an exhaled air purification unit can comprise a sensor that can sense the presence or absence of an individual that is within 3 feet of the front of the exhaled air collector, by way of example. The sensor can be one or more of an infrared ("IR") sensor, motion detector, photosensor, or vision system sensor. The sensor can turn the exhaled air purification unit on when an individual is sitting or standing within a set distance of the air purification unit and the sensor can turn the exhaled air purification unit off when the individual is no longer present. By way of example only, the sensor can determine, in aspects, if someone is sitting or standing at the desk or table supporting the exhaled air purification unit. An IR sensor can sense if an individual sitting or standing at the desk or table supporting an exhaled air purification unit has a body temperature above a certain threshold. By way of example only, if the IR sensor senses a temperature of, by way of example only, 98° F. or above, it can cause a speed of a fan or fans within or attached to one or more of the exhaled air purification unit, exhaled air collector, air suction intake, air suction conduit, and/or exhaled air purification chamber, to increase in velocity or cubic feet per minute. In addition, the IR sensor can cause the fan or fans of the exhaled air purification unit(s), air collector(s), and/or conduit(s) in or attached to the seats (or on a table or desk) to the right and/or left of the seat, table, desk, or work area directly in front to go to a higher CFM (cubic feet per minute of air flow). Thus, in certain embodiments, a fan or fans located within or attached to the exhaled air purification unit can operate at two or more different CFMs. Accordingly, in embodiments, a fan or fans located within or attached to the exhaled air collector can operate at two or more different CFMs. In embodiments a fan or fans located within or attached to the exhaled air purification chamber can operate at two or more different CFMs. In embodiments, a fan or fans located within or attached to a section or part of an exhaled air purification system or unit can operate at two or more different CFMs.

A networked exhaled air purification system that comprises a plurality of networked exhaled air collectors and/or exhaled air purification units that connect to one or more remote exhaled air purification chambers can comprise a sensor capable of determining if an individual is within 3 feet of the front of the exhaled air collector or exhaled air purification unit. A sensor, by way of example only, can be an IR sensor, which can determine, in aspects, a) if someone is sitting or standing in front of the exhaled air purification unit, and/or b) if an individual sitting or standing in front of the exhaled air purification unit has a body temperature above a certain threshold. By way of example only, if the IR sensor senses a threshold of a temperature of 98° F. or above it can cause speed of a fan within or attached to the exhaled air purification unit, and optionally fans associated with exhaled air purification units to the right and/or left and or in front or behind the sensed air purification unit to go to a higher CFM. Thus, in certain embodiments, the fan or fans located within or attached to the exhaled air purification unit can operate at two or more different CFMs.

In certain embodiments of the invention, the exhaled air purification unit can comprise a carbon dioxide ("$CO_2$") sensor. The exhaled air collector can comprise a $CO_2$ sensor. The exhaled air purification chamber can comprise a $CO_2$ sensor. The exhaled air purification system can comprise a $CO_2$ sensor. A higher $CO_2$ level can indicate a lack of good or sufficient air circulation within an indoor venue. Depending upon the level of $CO_2$ measured, the $CO_2$ sensor can cause a fan's CFM to increase or decrease in CFM. The exhaled air purification unit, air purification chamber, and/or air purification system can comprise an ozone sensor and cause an alarm, alert, or notification if ozone is present and/or if the level of ozone exceeds a preset threshold.

In embodiments, an air purification unit can include an acoustic sensor located, for example, within, on, or attached to, for example, an exhaled air collector. In aspects, the acoustic sensor can detect a sound, such as a cough, sneeze, voice, etc., and the air purification unit can in turn activate or change a speed of a fan in, on, or attached to the air purification unit. For example, if the sensor detects a sound, it can cause the air purification unit to increase a fan speed for, in aspects, a predetermined set amount of time. By way of example, after a set period of time (e.g., 30 seconds) after a cough or sneeze is detected, the fan speed can automatically return to its originally set speed prior to the sneeze or cough or turn off. In aspects, in the event of sensing a cough or sneeze, the air purification unit can increase a fan speed to cause the air purification unit to collect an increased amount of exhaled air. In aspects, a cough or sneeze may cause, by way of example only, a fan speed of 30 CFM to increase to 55 CFM, or a fan speed of 40 CFM to increase to 60 CFM or from 40 CFM to 100+ CFM. In aspects, a cough or sneeze may, by way of example only, cause a fan speed to increase by increments of 1 CFM, 2 CFM, 3 CFM, 4 CFM, 5 CFM, more than 5 CFM and so on.

In embodiments, non-cleaned, non-filtered exhaled air from the exhaled air collector can be moved into an exhaled air diagnostic device or analyzer or screener prior to being cleaned by the exhaled air purification chamber. In embodiments, a portion of the non-cleaned, non-filtered exhaled air from the exhaled air collector can be moved into the exhaled air diagnostic device or analyzer or screener prior to being cleaned by the exhaled air purification chamber. The exhaled air diagnostic device or analyzer can be integrated into the exhaled air purification unit or separate from but housed within the air purification unit. The exhaled air diagnostic device or analyzer can be used for screening purposes. The movement can be by way of air suction or fan(s) pushing the exhaled air, or a combination of both. The exhaled air diagnostic device or analyzer or screener can comprise a plurality of sensors. These sensors can be, by way of example only, chemical sensor(s), nano-sensor(s), electrochemical sensor(s), gas sensor(s), and/or thermal sensor(s). The sensors can be used to analyze/screen/test for abnormal chemical concentrations of molecules or compounds found within the collected non-cleaned and/or non-filtered exhaled air of an individual. By way of example only, it is known that one's exhaled breath analysis can indicate the possible presence (or propensity) of the following conditions or health abnormalities: diabetes, multiple sclerosis, Parkinson disease, Alzheimer's, tuberculosis, chronic kidney disease, cancer of (lung, colon, breast, prostrate), asthma, stomach ulcers, COVID, bad breath, liver pathogenesis, and/or alcoholism. The analysis can be limited in scope for the presence, by way of example only, of one or more of nicotine, cigarette smoke, marijuana smoke, alcohol, or an additive drug or pharmaceutical. The exhaled air diagnostic device or analyzer or screener can comprise a communication module. Such a communication module can have the option to provide the individual whose exhaled air has been or is to be analyzed to approve or disapprove of having his or her exhaled air analyzed. Such a communication module can have the option to block any communication of the analysis of the individual's exhaled air. Such a communication module can have the option to approve the communication of the analysis of the individual's exhaled air. The communication module can provide wired or wireless communication to the individual whose exhaled air is being analyzed and/or to a third party. Software can provide for the ability to list those individuals who should be sent the exhaled air analysis. Such software can be shown on a video display screen prompting the individual to answer certain questions and optionally approve or disapprove of having his or her breath analyzed. Such communication can be that of an analysis of the individual's breath or an alert concerning a condition that was potentially identified to which the individual or the individual's doctor should be made aware of. The exhaled air diagnostic device or analyzer or screener can communicate wirelessly to a mobile device of the individual. Such a mobile device can be, by way of example only, a cell phone, tablet computer, laptop computer, smart watch, or other electronic device. The exhaled air diagnostic device or analyzer or screener can communicate to a video display screen located on or in the back of a seat, or on a tabletop or a desktop. The exhaled air diagnostic device or analyzer or screener can communicate to a video display screen within or as part of an exhaled air collector. The exhaled air diagnostic device or analyzer or screener can comprise its own video display screen. In embodiments, the exhaled air diagnostic device or analyzer or screener can be independent of the exhaled air purification unit or system. In embodiments, the exhaled air diagnostic device or analyzer or screener can be located on, in, or separated from but in front of a back of a seat, chair, or bench within a multi-seated indoor venue. In certain embodiments the exhaled air collector can be that of a combination of a video display screen and its surrounding frame or housing. In this embodiment the air suction conduit can be an arm that secures or supports the video display screen. The video display screen can be part, or all, of the recessed exhaled air blocking surface. The exhaled air can be that of non-cleaned and/or non-filtered exhaled air. AI (artificial intelligence) and/or Machine Learning can be utilized to improve the analysis of the exhaled air and/or improve the screening and/or diagnosis accuracy. The exhaled air of an individual can be analyzed or screened, for example, while an individual is sitting or standing near an air purification unit or system or an exhaled air collector. The exhaled air of an individual can be analyzed or screened, for example, while an individual is sitting or standing near an air purification unit or system or an exhaled air collector. The exhaled air of an individual can be analyzed or screened, for example, while an individual is sitting or standing near an air purification unit or system or an exhaled air collector such as, by way of example only, one of, while sitting or standing at a desk or table, being transported in a vehicle, sitting in a classroom, sitting in a vehicle, or sitting in a theater, by way of example. In embodiments of the invention the individual's exhaled air can be subjected to microbe screening. In embodiments of the invention, the individual's exhaled air can be subjected to microbe diagnosis and/or its existence. In embodiments of the invention, an individual's exhaled air can be subjected to viral diagnosis and/or its existence. In embodiments of the invention, an individual's exhaled air can be subjected to germ diagnosis and/or its existence. In embodiments of the invention, the individual's exhaled air can be subjected to coronavirus diagnosis and/or its existence. In embodiments of the invention, an individual's exhaled air can be subjected to microbe diagnosis and/or its existence. In embodiments of the invention, an individual's exhaled air can be subjected to viral diagnosis and/or its existence. In embodiments of the invention, an individual's exhaled air can be subjected to germ diagnosis and/or its existence. In an embodiment of the invention the individual's exhaled air can be subjected to an analysis for substance abuse or chemical agents such as, by way of example only, nicotine, alcohol, marijuana, or opioids. Downward air flow from above the individual's seat can be used to assist in moving the individual's air into an exhaled air collector located in the back, top, or side of the seat in front of the passenger or attendee. The individual's exhaled air can be subjected to a microchip. The individual's exhaled air can be subjected to a gas sensor. The individual's exhaled air can be subjected to an electrochemical sensor. The individual's exhaled air can be subjected to a thermal sensor. The individual's exhaled air can be subjected to a spectrometer. The individual's exhaled air can be subjected to THz spectroscopy. The microchip, after being exposed to the individual's exhaled air, can be subjected to a spectrometer. A spectrometer can be part of the exhaled air purification system or exhaled air purification unit. A THz spectroscopy can be part of the exhaled air purification system or exhaled air purification unit. A computer device can be part of the exhaled air purification system or exhaled air purification unit. A communication device can be part of the air exhaled air purification system or exhaled air purification unit. In embodiments, an exhaled air purification system or exhaled air purification unit using diagnostics can inform an infected individual if they are infected with a virus or germ. In embodiments the exhaled air purification unit or system can inform the captain of a vehicle that an infected passenger is traveling on their vehicle. In embodiments the exhaled air purification system or the exhaled air purification unit using diagnostics can inform the owner of the vehicle that an infected passenger is traveling on their vehicle. In embodiments the exhaled air purification system or the exhaled air purification unit using diagnostics can inform an owner, driver, pilot, and/or attendant of the vehicle that an infected passenger is traveling on their vehicle. In embodiments the exhaled air purification system or the exhaled air purification unit using diagnostics can inform an owner, driver, pilot, and/or attendant of the vehicle that an infected passenger is traveling on their vehicle, and in which seat the infected passenger is sitting. The same can occur within a multi-seated theater in which an attendee is sitting, however in this case, by way of example only, theater management or a security guard may be informed. The same can occur within a school or university in which the individual is sitting, however in this case, the school administrator, school nurse, teacher or professor could be informed.

Figure 35:
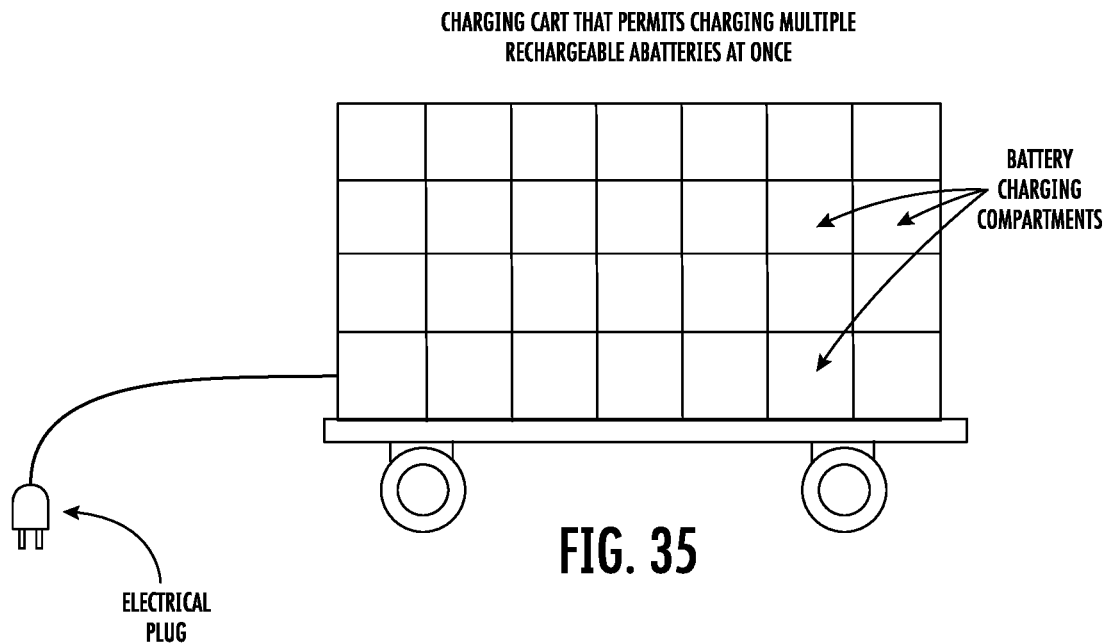
FIG. 35 is a drawing of a possible embodiment according to the present invention showing a charging cart that permits for charging multiple batteries at once.

The exhaled air purification chamber and exhaled air collector (when a fan is present with the exhaled air collector) can utilize alternating current as its power source when it is available. The exhaled air purification chamber and exhaled air collector (when a fan is present with the exhaled air collector) can utilize a rechargeable battery or a solid-state battery for its power source. In an embodiment a charge station or charge platform can provide for charging up to 100 batteries at one time. The charge platform can be on wheels and can be moved around. (See, e.g., FIG. 35 showing a charging cart that permits charging multiple batteries at once, including an electrical plug, wheels, and battery charging compartments, in embodiments.)

Figure 36:
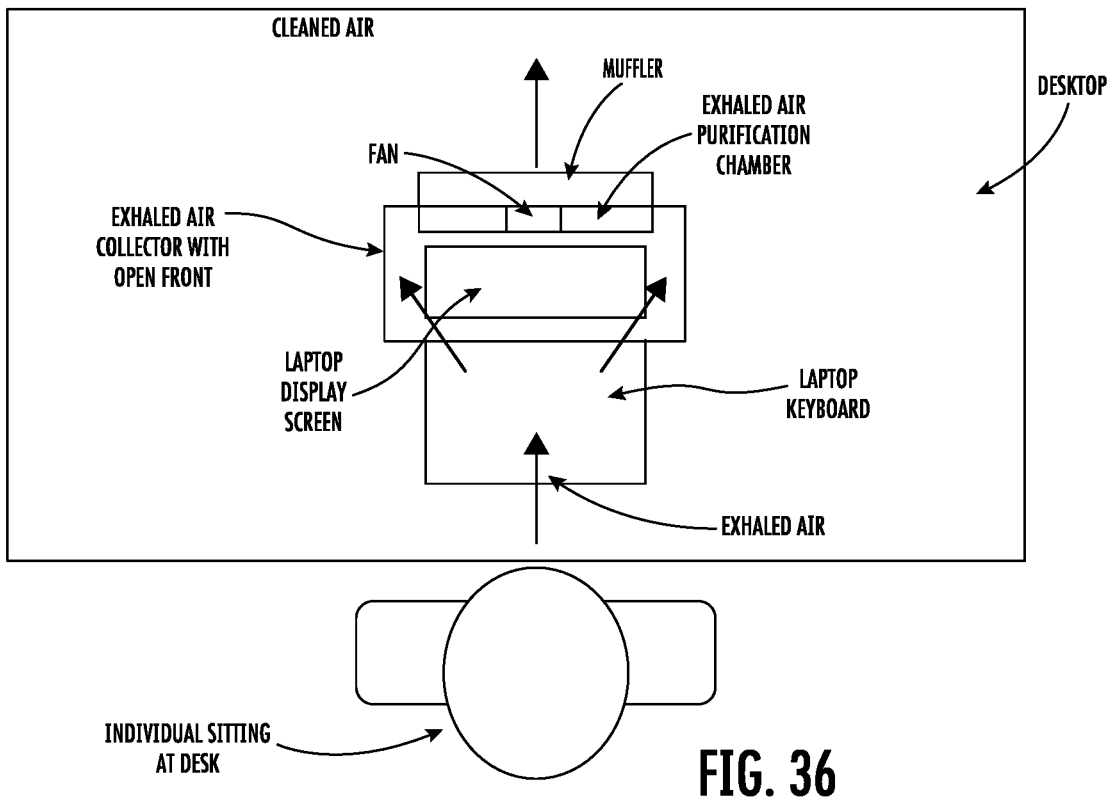
FIG. 36 is a top-looking-down view drawing of a possible embodiment according to the present invention showing an air purification unit.
Figure 37:
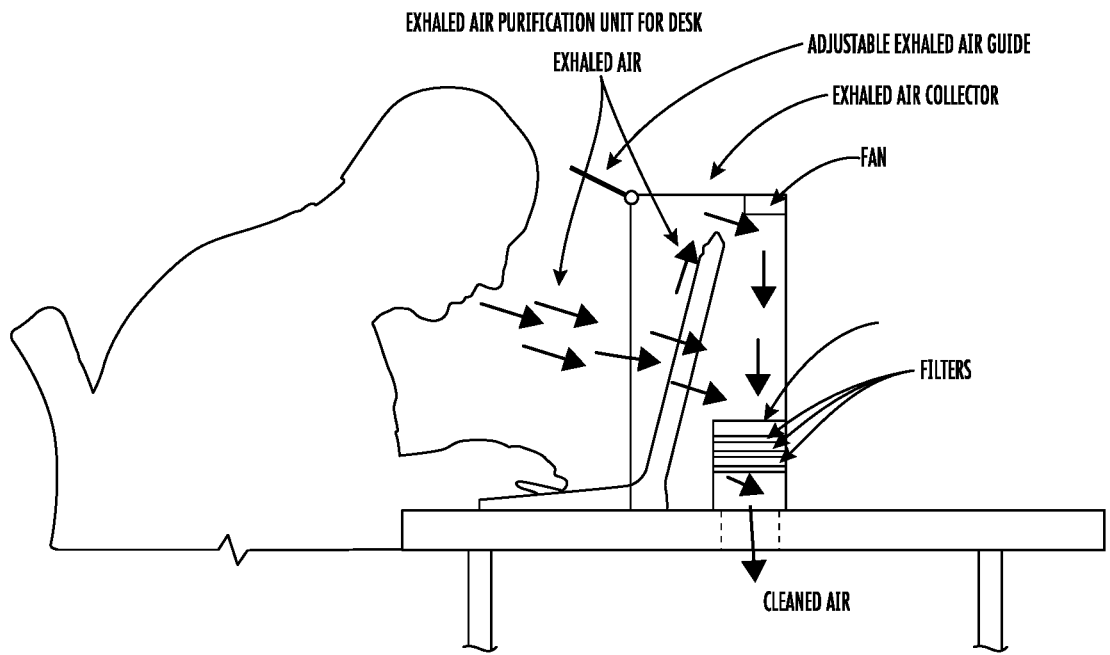
FIG. 37 is a side view drawing of a possible embodiment according to the present invention showing an air purification unit.
Figure 38:
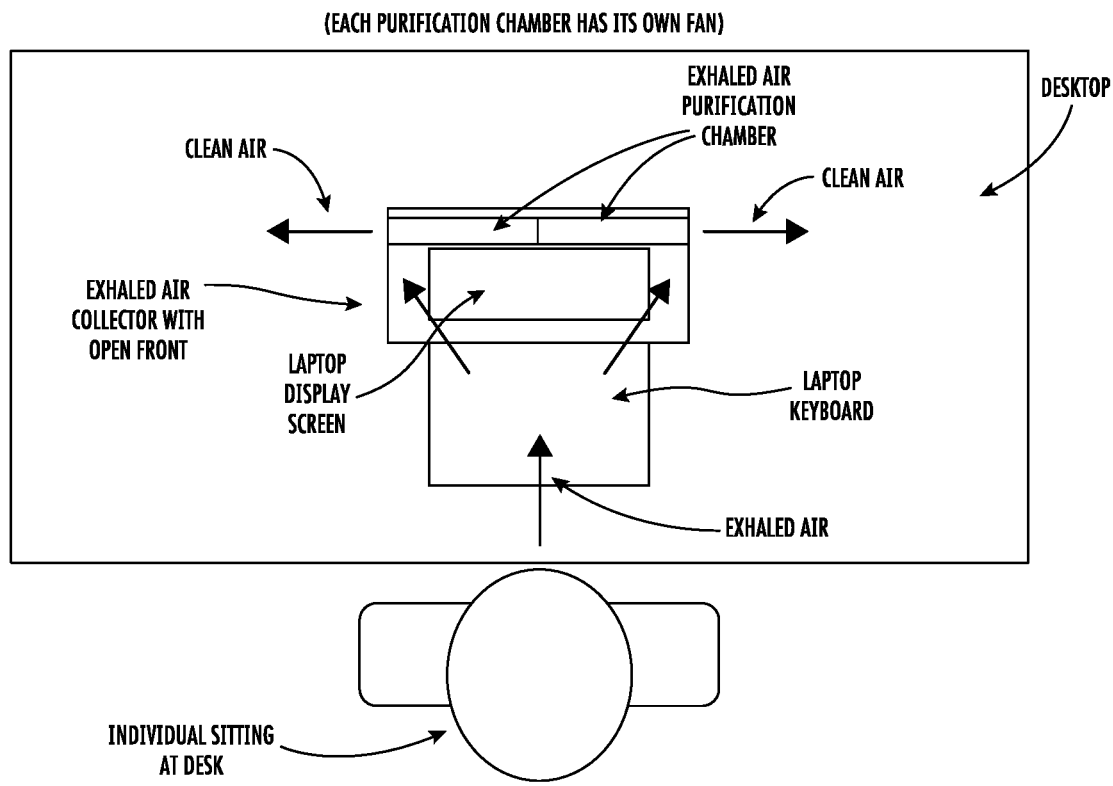
FIG. 38 is a top-looking-down view drawing of a possible embodiment according to the present invention showing an air purification unit.
Figure 39:
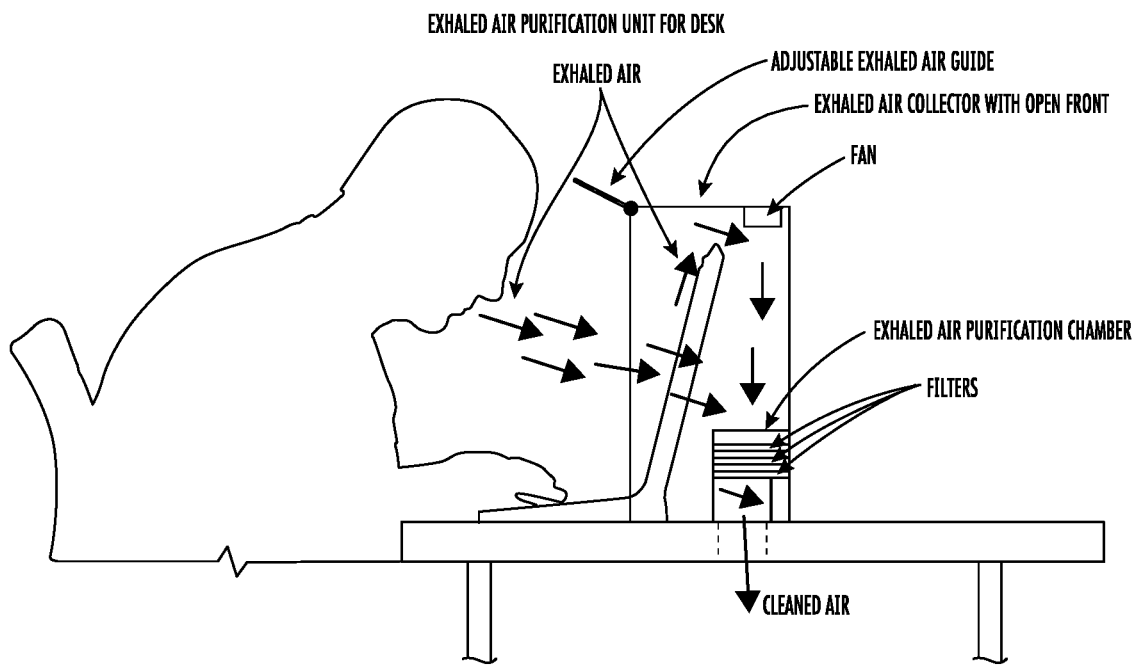
FIG. 39 is a side view drawing of a possible embodiment according to the present invention showing an air purification unit.

FIG. 36 shows a top-down view of a person in front of and using the air purification unit. In this case exhaled air is shown going to the exhaled air collector and then to the air purification chamber by an air suction fan. The air purification chamber cleans the air and it is exhausted back into the environment. In this aspect the air purification unit is resting on a desktop or tabletop. In this case a laptop computer is position partly inside the air collector (e.g., the screen is in the air collector and the keyboard is outside of the air collector). The air collector comprises an open front. In this embodiment, a muffler or component is associated with the air purification chamber to reduce noise emitted by using the air purification unit. FIG. 37 shows an air purification unit embodiment from the side, wherein the human's exhaled air is shown by arrows going into the exhaled air collector. In this side view, it is shown where the opening on the front, user-facing side of the exhaled air collector has an opening that allows for entry of the exhaled air and in this case placement of a laptop computer. In this embodiment, the exhaled air travels to an air purification chamber located within the exhaled air collector (e.g., a cavity within the exhaled air collector). In this example the exhaled air is filtered by one or more filters, and the cleaned air leaves or is exhausted from the air purification unit. Further, this embodiment shows the exhaled air collector comprising a fan blowing air downwards to the bottom of the exhaled air collector and into the air purification chamber. An adjustable exhaled air guide is also shown, as described herein. Finally, in this embodiment, dotted lines shown going through the desk or table indicate a conduit that extends through an aperture, hole, or opening that allows cleaned air to move downward through the desk or table and towards the floor and back into the environment from which the air was collected. FIGS. 38 and 39 are like FIGS. 36 and 37, but in addition to the items listed above shown in FIG. 36, the system uses two air purification chambers and in aspects each air purification chamber has its own fan(s) for suction and/or exhaust. In this case, cleaned air can be shown exiting the air purification chambers on the side of the air purification unit. Like FIG. 37, FIG. 39 shows the same elements but in this case the air purification chamber(s) has its own fan for suction and/or exhaust. If for exhaust, it facilitates cleaned air being exhausted through a conduit that extends through an aperture, hole, or opening that allows cleaned air to move downward through the desk or table and towards the floor and back into the environment from which the air was collected.

The invention herein includes, in part, several Aspects:

Aspect 1: An air treating device comprising an exhaled air collector and an exhaled air purification chamber, wherein the exhaled air collector comprises at least a top, a bottom, one or more sides, a back, and a partially or completely open front, wherein all or a portion of one or more of the top, the bottom, the one or more sides, the back, and the partially or completely open front comprise an air suction intake, wherein all or a portion of one or more of the top, the bottom, the one or more sides, the back, and the partially or completely open front optionally comprise an exhaled air blocking surface, wherein the partially or completely open front of the exhaled air collector is located closer to a face of a person whose exhaled air is being collected by the exhaled air collector than the exhaled air purification chamber, and wherein an air collecting and air treating operation of the air treating device is dependent upon:

a combination of an exhaled air flow trajectory and a velocity of exhaled air flow from the person whose exhaled air is being collected by the exhaled air collector; and an air suction force of the air suction intake.

Aspect 2: The air treating device of Aspect 1, wherein the partially or completely open front of the exhaled air collector is located within 3 inches to 6 feet of the person whose exhaled air is being collected by the exhaled air collector.

Aspect 3: The air treating device of Aspect 1, wherein the exhaled air collector further comprises one or more exhaled air guide, wherein the one or more exhaled air guide is optionally adjustable.

Aspect 4: The air treating device of Aspect 1, wherein the exhaled air collector collects exhaled air of two or more people located in front of the exhaled air collector.

Aspect 5: The air treating device of Aspect 1, wherein two or more exhaled air collectors are connected to the same air exhaled air purification chamber.

Aspect 6: The air treating device of Aspect 1, wherein two or more exhaled air collectors are connected to or share the same exhaled air suction intake.

Aspect 7: The air treating device of Aspect 1, wherein the exhaled air collector is connected to the exhaled air purification chamber by a conduit.

Aspect 8: The air treating device of Aspect 1, wherein the exhaled air collector, the exhaled air purification chamber, or both, are portable.

Aspect 9: The air treating device of Aspect 1, wherein each of a plurality of the exhaled air collectors include at least one air suction intake.

Aspect 10: The air treating device of Aspect 1, wherein the air treating device comprises an exhaled air collector comprising a partially or completely open front, and wherein the partially or completely open front allows for an individual to manipulate an object contained partially or fully within the exhaled air collector.

Aspect 11: An air treating device comprising:
one or more exhaled air collectors comprising a partially or completely open front; and one or more exhaled air purification chambers;
wherein the one or more exhaled air collectors are located on a desktop or tabletop, wherein the one or more exhaled air collectors comprise one or more air suction intakes, optionally one or more air suction conduits, or both, wherein the one or more exhaled air collectors are connected to the one or more air purification chambers, wherein the one or more air purification chambers are located on the desktop or tabletop, beside the desktop or tabletop, under the desktop or tabletop, or distance separated from the desktop or tabletop.

Aspect 12: The air treating device according to one of the above Aspects, wherein an operation of the air treating device is dependent upon:
a combination of an exhaled air flow trajectory and a velocity of exhaled air flow from a person whose exhaled air is being collected by the one or more exhaled air collectors; and an air suction force of the one or more air suction intakes.

Aspect 13: The air treating device according to one of the above Aspects, wherein the partially or completely open front of the one or more exhaled air collectors are located within 3 inches to 6 feet of a person whose exhaled air is being collected by the one or more exhaled air collectors.

Aspect 14: The air treating device according to one of the above Aspects, wherein the partially or completely open front of the one or more exhaled air collectors are located within 12 inches to 6 feet of a person whose exhaled air is being collected by the one or more exhaled air collectors.

Aspect 15: The air treating device according to one of the above Aspects, wherein the one or more exhaled air collectors further comprise one or more exhaled air guide, wherein the one or more exhaled air guide is optionally adjustable.

Aspect 16: The air treating device according to one of the above Aspects, wherein the one or more exhaled air collectors collect exhaled air of two or more people located in front of the one or more exhaled air collectors.

Aspect 17: The air treating device according to one of the above Aspects, wherein more than one of the one or more exhaled air collectors are connected to the same one or more exhaled air purification chambers.

Aspect 18: The air treating device according to one of the above Aspects, wherein more than one of the one or more exhaled air collectors are connected to the same one or more air suction intakes.

Aspect 19: The air treating device according to one of the above Aspects, wherein more than one of the one or more exhaled air collectors are connected to or share the same one or more air suction conduits.

Aspect 20: The air treating device according to one of the above Aspects, wherein the one or more exhaled air collectors, the one or more air purification chambers, or both, are portable.

Aspect 21: The air treating device according to one of the above Aspects, wherein each of a plurality of the one or more exhaled air collectors include at least one air suction intake.

Aspect 22: The air treating device of Aspect 1, wherein each of a plurality of the one or more exhaled air collectors include at least one air suction intake, and wherein each of the at least one air suction intake leads to the same one or more exhaled air purification chambers.

Aspect 23: A portable backpack, briefcase, purse, wallet, suitcase, or other luggage, which is capable of being used as an exhaled air collector, wherein the portable backpack, briefcase, purse, wallet, suitcase, or other luggage further comprises an exhaled air purification chamber.

Aspect 24: A portable backpack, briefcase, purse, wallet, suitcase, or other luggage, which is capable of being used as an exhaled air collector, wherein the portable backpack, briefcase, purse, wallet, suitcase, or other luggage further comprises a member that connects the exhaled air collector to an exhaled air purification chamber, an air suction intake, an air suction conduit, or a combination thereof.

The invention herein includes, in part, several Aspects:

Aspect 1A: An exhaled air purification device comprising an exhaled air collector and an exhaled air purification chamber, wherein the exhaled air purification chamber is one or more of attached to, adjacent to, or connected by a conduit to the exhaled air collector, or wherein the exhaled air purification chamber is located completely or partially within the exhaled air collector, and wherein the exhaled air collector comprises an open front.

Aspect 2A: The exhaled air purification device of Aspect 1, wherein the exhaled air collector comprises a recessed exhaled air blocking surface.

Aspect 3A. The exhaled air purification device of Aspect 1, wherein the exhaled air collector or an exhaled air collector's back, top, bottom, or side completely or partially surrounds a front section of the exhaled air purification chamber, wherein the front section of the exhaled air purification chamber comprises an air intake.

Aspect 4A. The exhaled air purification device of Aspect 1, wherein the exhaled air collector actively or passively collects exhaled air of a human sitting or standing in front of or near the exhaled air collector.

Aspect 5A. The exhaled air purification device of Aspect 1, wherein the exhaled air collector can have all or part of a laptop computer, a desktop computer, a holographic system, a projection system, an electronic display, or a visual display inserted or located within the exhaled air collector.

Aspect 6A. The exhaled air purification device of Aspect 1, wherein the exhaled air collector's height, width, and/or depth is adjustable.

Aspect 7A. The exhaled air purification device of Aspect 1, further comprising an air suction conduit operably connecting the exhaled air collector to a remote air purification chamber.

Aspect 8A. The exhaled air purification device of Aspect 1, wherein the exhaled air collector comprises one or more fans.

Aspect 9A. The exhaled air purification device of Aspect 1, wherein the exhaled air purification device further comprises a sensor, wherein the sensor causes the exhaled air purification device to turn on when an individual is within 3 feet of the exhaled air purification device and turn off when a human is not within 3 feet of the exhaled air purification device.

Aspect 10A. The exhaled air purification device of Aspect 9, wherein the sensor is one or more of a motion sensor, a thermal sensor, an infrared (IR) sensor, a photosensor, or a visual sensor.

Aspect 11A. The exhaled air purification device of Aspect 1, wherein the exhaled air purification chamber comprises, is attached to, and/or is partially surrounded by an acoustic silencer or muffler.

Aspect 12A. The exhaled air purification device of Aspect 1, wherein the exhaled air collector is made of a clear or a semi-clear material.

Aspect 13A. The exhaled air purification device of Aspect 1, wherein the exhaled air collector is made of fabric, paper, metal, plastic, glass, wood, rubber, or a combination thereof.

Aspect 14A. The exhaled air purification device of Aspect 1, wherein the exhaled air collector is made of a flexible material.

Aspect 15A. The exhaled air purification device of Aspect 1, wherein the air purification chamber comprises one or more of a pre-filter, a filter, a HEPA filter, a carbon filter, an ionizer, a UV light, a UVC light, a germicidal light, a plasma generator, a microbicidal agent, a microbicidal material, and ultrasonic generator, or a thermal heating element or member.

Aspect 16A. The exhaled air purification device of Aspect 1, wherein a first exhaled air collector and a second exhaled air collector move collected exhaled air to one or more exhaled air purification chambers, and wherein the one or more exhaled purification chambers purify, clean, sterilize, and/or filter the exhaled air received from the first exhaled air collector and the second exhaled air collector.

Aspect 17A. The exhaled air purification device of Aspect 1, wherein one or more physical dimensions of the exhaled air purification device are adjustable.

Aspect 18A. An exhaled air purification device of Aspect 1, wherein the exhaled air collector contains a first section of the exhaled air purification chamber, wherein the first section of the exhaled air purification comprises an exhaled air intake, wherein a second section of the exhaled air purification chamber is located outside of the exhaled air collector, and wherein the second section comprises an air outlet that exhausts cleaned air.

Aspect 19A. The exhaled air purification device of Aspect 1, further comprising an exhaled air analyzer.

Aspect 20A. The exhaled air purification device of Aspect 19, wherein the exhaled air analyzer detects one or more of an illness, a disease, or a health abnormality or pathology.

Aspect 21A. The exhaled air purification device of Aspect 19, wherein the exhaled air analyzer detects a presence of one or more of alcohol, nicotine, marijuana, an opioid, or an addictive pharmaceutical.

Aspect 22A. The exhaled air purification device of Aspect 1, wherein the exhaled air purification device is capable of processing 0.21188 cubic feet per minute or more of air.

Aspect 23A. The exhaled air purification device of Aspect 1, wherein the air purification chamber has a clean air delivery rate (CADR) of 3 CADR or more and a noise level of 50 decibels or less.

Aspect 24A. The exhaled air purification device of Aspect 1, wherein the exhaled air purification device is one or more of attached to a back of a sitting apparatus, integrated within a back of a sitting apparatus, supported by a support member that is distance separated from a back of a sitting apparatus, located within a conduit within a back of a sitting apparatus, or positioned on a desktop or a tabletop.

Aspect 25A. The exhaled air purification device of Aspect 1, wherein the exhaled air collector comprises an adjustable exhaled air guide.

Aspect 26A. The exhaled air purification device of Aspect 1, further comprising one or more of a $CO_2$ sensor, an Ozone sensor, or a UV sensor, and wherein the exhaled air purification device can communicate an alert.

Aspect 27A. The exhaled air purification device of Aspect 1, wherein the exhaled air purification chamber or a portion thereof is located on top of, within, or below a desktop or tabletop.

Aspect 28A. The exhaled air purification device of Aspect 1, wherein the exhaled air purification chamber is one or more of located within, attached to, below, or distance removed from a chair, seat, bench, or sitting apparatus.

Aspect 29A. The exhaled air purification device of Aspect 1, wherein a front section of the air purification chamber comprises an air intake, and wherein the front section of the air purification chamber makes up part or all of a back wall of the exhaled air collector.

Aspect 30A. The exhaled air purification device of Aspect 1, wherein one or more of the exhaled air collector, the exhaled air purification chamber, or an optional conduit, comprises a microbicidal agent or material.

The invention herein includes, in part, several Aspects:

Aspect 1B: An air treating device comprising an exhaled air collector, an exhaled air purification chamber, and an air suction intake, wherein the exhaled air collector comprises an open front or a partially open front, wherein the open front or the partially open front of the exhaled air collector is located closer to a face of a person whose exhaled air is being collected by the exhaled air collector than the exhaled air purification chamber, wherein the face of the person whose exhaled air is being collected is within a distance of 1 foot to 6 feet of the open front or the partially open front of the exhaled air collector, and wherein a volume of exhaled air collected by the air treating device is dependent upon:

a combination of an exhaled air flow trajectory and a velocity of exhaled air flow from the person whose exhaled air is being collected by the exhaled air collector; and an air suction force of the air suction intake.

Aspect 2B: The air treating device of Aspect 1B, wherein the open front or the partially open front of the exhaled air collector is located within 3 inches to 6 feet of the person whose exhaled air is being collected by the exhaled air collector.

Aspect 3B: The air treating device of Aspect 1B, wherein the open front or the partially open front of the exhaled air collector is located within 1 foot to 3 feet of the person whose exhaled air is being collected by the exhaled air collector.

Aspect 4B: The air treating device of Aspect 1B, wherein the exhaled air collector further comprises one or more exhaled air guide, wherein the one or more exhaled air guide is optionally adjustable.

Aspect 5B: The air treating device of Aspect 1B, wherein the exhaled air collector collects exhaled air of one person or a plurality of people located in front of the exhaled air collector.

Aspect 6B: The air treating device of Aspect 1B, wherein two or more exhaled air collectors are connected to the same air exhaled air purification chamber.

Aspect 7B: The air treating device of Aspect 1B, wherein two or more exhaled air collectors are connected to or share the same air suction intake.

Aspect 8B: The air treating device of Aspect 1B, wherein the exhaled air collector is connected to the exhaled air purification chamber by a conduit.

Aspect 9B: The air treating device of Aspect 1B, wherein the exhaled air collector, the exhaled air purification chamber, or both, are portable.

Aspect 10B: The air treating device of Aspect 1B, wherein each of a plurality of the exhaled air collectors include at least one air suction intake.

Aspect 11B: The air treating device of Aspect 1B, wherein the open front or the partially open front of the exhaled air collector allows for an individual to manipulate an object contained partially or fully within the exhaled air collector.

Aspect 12B: An air treating device comprising:

one or more exhaled air collectors comprising a partially or completely open front; and one or more exhaled air purification chambers;

wherein the one or more exhaled air collectors are located on a desktop or tabletop;

wherein the one or more exhaled air collectors comprise one or more air suction intakes;

wherein the one or more air suction intakes are optionally connected to one or more air suction conduits;

wherein the one or more exhaled air collectors partially or completely surround part or all of one or more air purification chambers, wherein the one or more exhaled air collectors are connected or attached to one or more air purification chambers, or both; and wherein the one or more air purification chambers are located on the desktop or tabletop, beside the desktop or tabletop, under the desktop or tabletop, or distance separated from the desktop or tabletop.

Aspect 13B: The air treating device of Aspect 12B, wherein an operation of the air treating device is dependent upon:

a combination of an exhaled air flow trajectory and a velocity of exhaled air flow from a person whose exhaled air is being collected by the one or more exhaled air collectors; and an air suction force of the one or more air suction intakes.

Aspect 14B: The air treating device of Aspect 12B, wherein the partially or completely open front of the one or more exhaled air collectors are located within 3 inches to 6 feet of a person whose exhaled air is being collected by the one or more exhaled air collectors.

Aspect 15B: The air treating device of Aspect 12B, wherein the partially or completely open front of the one or more exhaled air collectors are located within 12 inches to 6 feet of a person whose exhaled air is being collected by the one or more exhaled air collectors.

Aspect 16B: The air treating device of Aspect 12B, wherein the one or more exhaled air collectors further comprise one or more exhaled air guide, wherein the one or more exhaled air guide is optionally adjustable.

Aspect 17B: The air treating device of Aspect 12B, wherein the one or more exhaled air collectors collect exhaled air of two or more people located in front of the one or more exhaled air collectors.

Aspect 18B: The air treating device of Aspect 12B, wherein more than one of the one or more exhaled air collectors are connected to the same one or more exhaled air purification chambers.

Aspect 19B: The air treating device of Aspect 12B, wherein more than one of the one or more exhaled air collectors are connected to the same one or more air suction intakes.

Aspect 20B: The air treating device of Aspect 12B, wherein more than one of the one or more exhaled air collectors are connected to or share the same one or more air suction conduits.

Aspect 21B: The air treating device of Aspect 12B, wherein the one or more exhaled air collectors, the one or more air purification chambers, or both, are portable.

Aspect 22B: The air treating device of Aspect 12B, wherein each of a plurality of the one or more exhaled air collectors include at least one air suction intake.

Aspect 23B: The air treating device of Aspect 1B, wherein a plurality of exhaled air collectors each include at least one air suction intake, and wherein each of the at least one air suction intake leads to the same one or more exhaled air purification chambers.

Aspect 24B: An exhaled air collector, wherein the exhaled air collector comprises an open front or a partially open front, wherein the exhaled air collector is located within 1 foot to 6 feet of a person whose exhaled air is being collected, wherein a volume of exhaled air collected depends upon a combination of:

an exhaled air flow trajectory and a velocity of exhaled air flow from the person whose exhaled air is being collected by the exhaled air collector; and an air suction force of an air suction intake.

Aspect 25B: The exhaled air collector of Aspect 24B, wherein the exhaled air collector is one of a portable backpack, briefcase, purse, wallet, suitcase, or other luggage, wherein the portable backpack, briefcase, purse, wallet, suitcase, or other luggage further comprises an exhaled air purification chamber.

Aspect 26B: The exhaled air collector of Aspect 24B, wherein the exhaled air collector is one of a portable backpack, briefcase, purse, wallet, suitcase, or other luggage, wherein the portable backpack, briefcase, purse, wallet, suitcase, or other luggage further comprises a member that connects the exhaled air collector to an exhaled air purification chamber, an air suction intake, an air suction conduit, or a combination thereof.

Aspect 27B: The exhaled air collector of Aspect 24B, wherein the exhaled air collector is flexible.

Aspect 28B: The exhaled air collector of Aspect 24B, wherein the exhaled air collector is transparent or semi-transparent.

Aspect 29B: The exhaled air collector of Aspect 24B, wherein the exhaled air collector is supported by a desktop, tabletop, desk, table, chair, seat, bench, chair back, seat back, bench back, or a combination thereof, or wherein the exhaled air collector is located behind and distance separated from a chair back, seat back, or bench back.

One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. An air treating device comprising:
    an exhaled air collector, wherein the exhaled air collector comprises a partially or completely open front and a recessed exhaled air blocking surface, and (a) wherein a surface area of the exhaled air blocking surface can be increased or decreased by adjusting a top of the exhaled air collector up or down, (b) wherein the exhaled air collector comprises an adjustable exhaled air guide located at the top of the exhaled air collector to direct exhaled air of a user into the exhaled air collector, or (c) wherein the surface area of the exhaled air blocking surface can be increased or decreased by adjusting a top of the exhaled air collector up or down and the exhaled air collector comprises an adjustable exhaled air guide located at the top of the exhaled air collector to direct the exhaled air of the user into the exhaled air collector or; and
    an exhaled air purification chamber;
    wherein the exhaled air collector further comprises an air suction intake that suctions the exhaled air of the user downwards and either directly to the exhaled air purification chamber or through a conduit to the exhaled air purification chamber; and
    wherein the air suction intake is at least one of located at a bottom of the exhaled air collector and facing upwards and located within the exhaled air collector and entirely in a lower half of the recessed exhaled air blocking surface.

2. The air treating device of claim 1, wherein an operation of the air treating device is dependent upon:
    a combination of an exhaled air flow trajectory and a velocity of exhaled air flow from the user whose exhaled air is being collected by the exhaled air collector; and
    an air suction force of the air suction intake.

3. The air treating device of claim 1, wherein the partially or completely open front of the exhaled air collector is located within 3 inches to 6 feet of the user whose exhaled air is being collected by the exhaled air collector.

4. The air treating device of claim 1, wherein the partially or completely open front of the exhaled air collector is located within 12 inches to 6 feet of the user whose exhaled air is being collected by the exhaled air collector.

5. The air treating device of claim 1, wherein the exhaled air collector collects exhaled air of two or more users located in front of the exhaled air collector.

6. The air treating device of claim 1, wherein at least two exhaled air collectors are connected to the exhaled air purification chamber.

7. The air treating device of claim 1, wherein at least two exhaled air collectors are connected to or share the same conduit.

8. The air treating device of claim 1, wherein the exhaled air collector, the exhaled air purification chamber, or both, are portable.

9. The air treating device of claim 1, wherein the exhaled air collector includes at least two air suction intakes.

10. The air treating device of claim 1, further comprising at least one additional exhaled air collector, wherein each of the additional exhaled air collectors include at least one air suction intake, and wherein each of the at least one air suction intakes leads to the exhaled air purification chamber.

11. The air treating device of claim 1, wherein the exhaled air collector is sized to house a display screen of at least one of a monitor, a computer monitor, a laptop computer, a tablet computer, a phone, and a television.

12. The air treating device of claim 1, wherein the air treating device comprises at least two exhaled air purification chambers.

\* \* \* \* \*